(12) United States Patent
Okabe et al.

(10) Patent No.: US 10,684,742 B2
(45) Date of Patent: Jun. 16, 2020

(54) MEDICAL SUPPORT APPARATUS, METHOD AND SYSTEM FOR MEDICAL CARE

(71) Applicant: FUJIFILM Corporation, Tokyo (JP)

(72) Inventors: Yuki Okabe, Tokyo (JP); Yasuyo Nenoki, Tokyo (JP); Yasunori Ohta, Tokyo (JP); Hiroshi Hiramatsu, Tokyo (JP); Tsuyoshi Hirakawa, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 1027 days.

(21) Appl. No.: 15/010,695

(22) Filed: Jan. 29, 2016

(65) Prior Publication Data

US 2016/0224195 A1  Aug. 4, 2016

(30) Foreign Application Priority Data

Jan. 30, 2015 (JP) .................. 2015-017943
Jan. 30, 2015 (JP) .................. 2015-017944

(51) Int. Cl.
*G06F 3/0482* (2013.01)
*G06F 3/0485* (2013.01)
*G16H 10/20* (2018.01)

(52) U.S. Cl.
CPC ......... *G06F 3/0482* (2013.01); *G06F 3/0485* (2013.01); *G16H 10/20* (2018.01)

(58) Field of Classification Search
CPC .................................................. G06F 3/0485
See application file for complete search history.

(56) References Cited

U.S. PATENT DOCUMENTS 5,499,334 A * 3/1996 Staab .................. G06F 3/0481
                                                        715/778
5,568,603 A * 10/1996 Chen .................. G06F 3/04845
                                                        715/784
(Continued)

FOREIGN PATENT DOCUMENTS

CN        1542634 A     11/2004
CN      102763108 A     10/2012
(Continued)

OTHER PUBLICATIONS

Harvey, "Excel 2010 All-in-One for Dummies," 2010, Wiley Publishing, Inc.*

(Continued)

*Primary Examiner* — Ryan Barrett
(74) *Attorney, Agent, or Firm* — Sughrue Mion, PLLC

(57) ABSTRACT

In a medical support system, a patient list or work list is displayed on a display panel of a client terminal apparatus. An information item number window area and a patient number window area are contained in the patient list. The information item number window area displays a number of items in an undisplayed portion outside an active display area. The patient number window area displays a number of datasets of personal information of patient bodies (number of patient bodies) in the undisplayed portion. A display form of the number window areas is translucent and in achromatic gray, in a tapered triangular shape to point a location of the undisplayed portion. Numbers are indicated in the number window areas. Thus, the patient list can be viewed by a medical professional with good visual perceptibility.

9 Claims, 48 Drawing Sheets

(56) References Cited

U.S. PATENT DOCUMENTS

| | | | | | |
|---|---|---|---|---|---|
| 5,689,708 | A | * | 11/1997 | Regnier | G06F 9/468 709/229 |
| 5,841,435 | A | * | 11/1998 | Dauerer | G06F 3/0481 715/775 |
| 5,933,141 | A | * | 8/1999 | Smith | G06F 3/0481 715/768 |
| 7,117,433 | B1 | * | 10/2006 | Glaser | G06F 16/958 715/205 |
| 7,426,701 | B2 | * | 9/2008 | Strausbaugh | G06Q 10/10 715/835 |
| 2002/0186252 | A1 | * | 12/2002 | Himmel | G06F 3/04855 715/787 |
| 2003/0071849 | A1 | * | 4/2003 | Ferri | G06F 3/0483 715/777 |
| 2004/0025179 | A1 | * | 2/2004 | Russ | H04N 5/44543 725/46 |
| 2004/0174398 | A1 | * | 9/2004 | Luke | G06F 3/0481 715/856 |
| 2004/0267595 | A1 | * | 12/2004 | Woodings | G06Q 10/06 705/7.14 |
| 2005/0003870 | A1 | | 1/2005 | Nakano et al. | |
| 2005/0091604 | A1 | * | 4/2005 | Davis | G06F 3/0482 715/772 |
| 2005/0204387 | A1 | * | 9/2005 | Knudson | G06F 3/0482 725/52 |
| 2006/0190837 | A1 | * | 8/2006 | Jarczyk | G06F 3/0481 715/778 |
| 2007/0247462 | A1 | * | 10/2007 | Bell | G06T 11/20 345/440 |
| 2008/0313540 | A1 | * | 12/2008 | Dirks | G06F 3/04815 715/710 |
| 2009/0169060 | A1 | * | 7/2009 | Faenger | G09B 29/007 382/113 |
| 2009/0282359 | A1 | * | 11/2009 | Saul | G06F 3/0481 715/784 |
| 2010/0146434 | A1 | * | 6/2010 | Blinnikka | G06F 40/18 715/785 |
| 2011/0078624 | A1 | * | 3/2011 | Missig | G06F 3/0483 715/802 |
| 2013/0086506 | A1 | * | 4/2013 | Molander | G06F 3/048 715/777 |
| 2013/0086507 | A1 | * | 4/2013 | Poston | G06F 3/0483 715/777 |
| 2013/0111353 | A1 | | 5/2013 | Ueda | |
| 2013/0271469 | A1 | * | 10/2013 | Moore | G06T 11/206 345/440.1 |
| 2015/0012843 | A1 | * | 1/2015 | Ouyang | H04L 65/403 715/753 |
| 2018/0165254 | A1 | * | 6/2018 | Talati | G06F 40/106 |

FOREIGN PATENT DOCUMENTS

| | | |
|---|---|---|
| JP | 2001-042854 A | 2/2001 |
| JP | 2006-338521 A | 12/2006 |
| JP | 2011038792 A | 2/2011 |

OTHER PUBLICATIONS

Communication drafted Dec. 20, 2017, from Japanese Patent Office in counterpart application No. 2015-017944.
Decision of Refusal and Decision to Decline the Amendment from the Japanese Patent Office in counterpart application No. 2015-017943, dated Dec. 4, 2018.
Notification of Reasons for Refusal dated Dec. 12, 2018 from the Japanese Patent Office in application No. 2018-106161.
Communication drafted Mar. 30, 2018 from the Japanese Patent Office in counterpart Japanese application No. 2015-017943.
First Office Action, issued in CN 201610066245.3, dated Mar. 31, 2020, 35 pages in English and Chinese.

* cited by examiner

F I G. 4
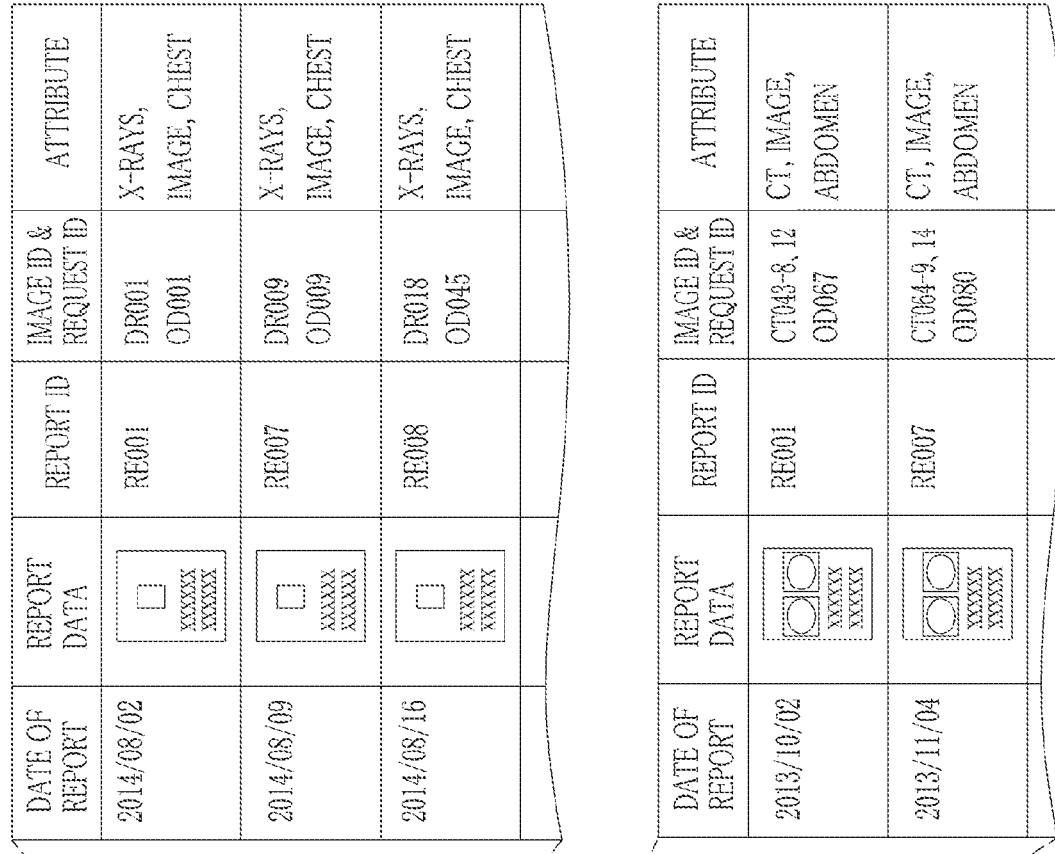
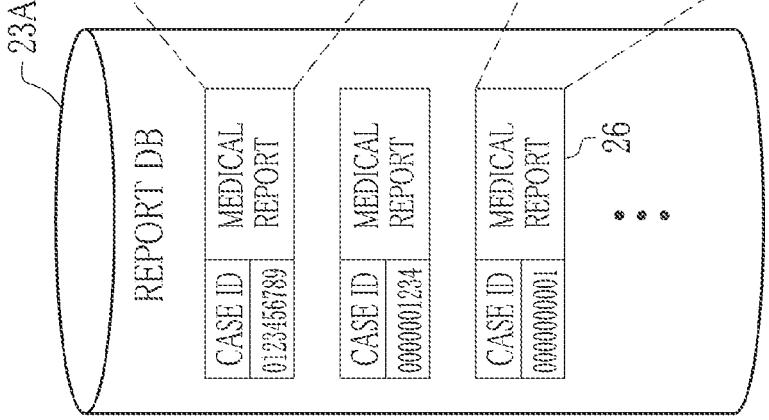

FIG. 6
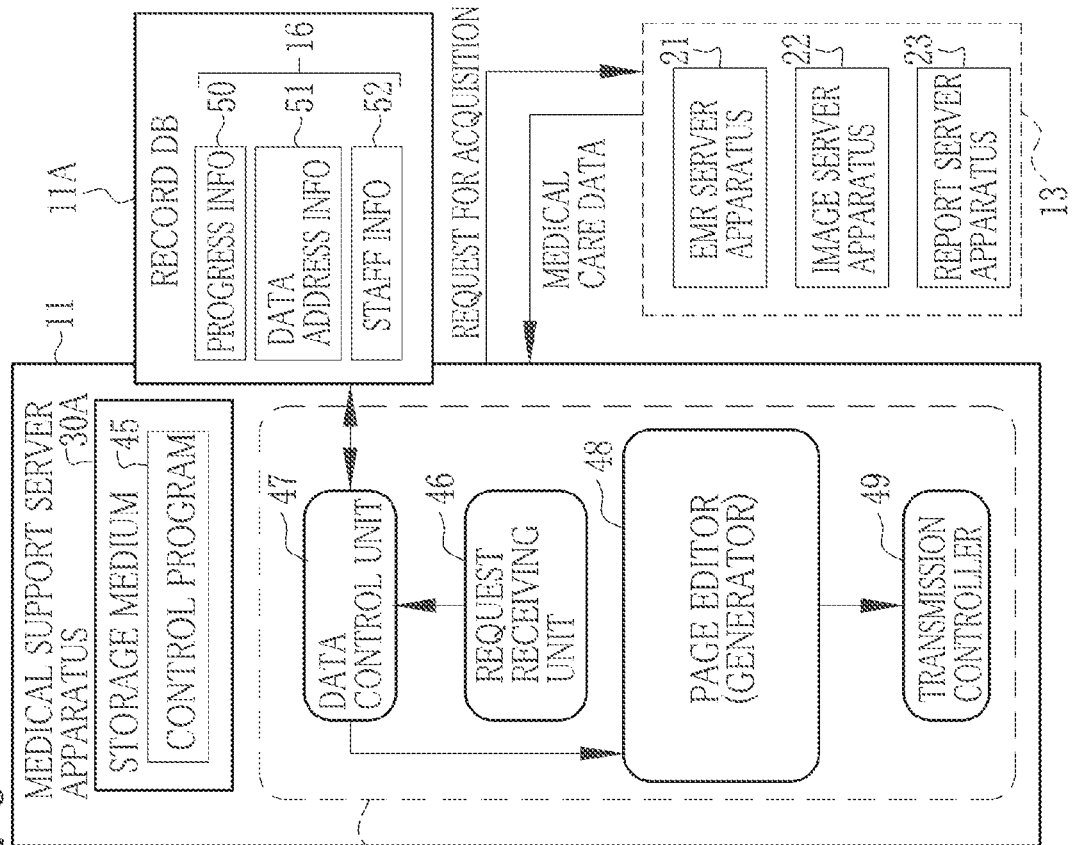
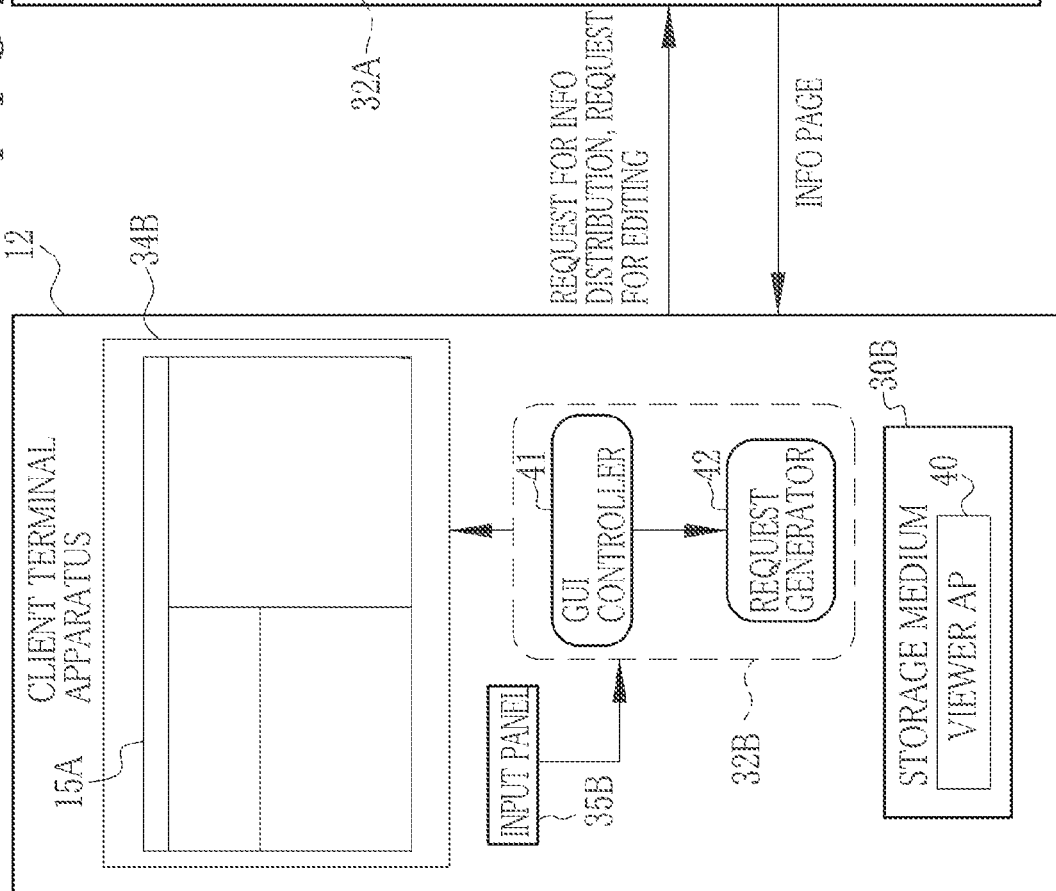

| FOR DOCTOR | | | | | INFO ITEMS OF CLINICAL PROCESS | | | | | |
|---|---|---|---|---|---|---|---|---|---|---|
| CASE ID | PATIENT TYPE | PROFES- SIONAL ID | SYMPTOM NAME | SCHEDULING OF HOSPITALIZATION | DIAGNOSTIC TEST | REQUEST FOR ANESTHESIA | PREOPERATIVE SUMMARY | REQUEST FOR SURGERY | CONSENT TO ANESTHESIA | CONSENT TO SURGERY |
| 012345678 | SURGERY- SCHEDULED PATIENT | D001 D005 D018 D050 | 01/23 Gastric Cancer D001 | 01/23 09:30 1/25 - 1/30 Room 405: Single | 01/24 DR: Non-tested US: D050 Unconfirmed D001, D005, D018 Confirmed ES: Confirmed | 01/23 General D005 | 01/23 Confirmed D001 | 01/23 1/28 14:30~ D001 | 01/23 1/25 D005 | 01/23 1/23 D001 |
| 001003210 | SURGERY- SCHEDULED PATIENT | D002 D005 D007 D039 | 01/23 Infiltrating Carcinoma D002 | 01/23 09:30 1/25 - 1/31 Room 505: Single | 01/24 CT, EC: Non-tested DR, ES, HM: Confirmed US: D007 Unconfirmed D002, D005, D039 Confirmed BC: Confirmed | 01/23 General D005 | 01/20 Interrupted Due to Liver Metastasis... D002 | 01/23 1/27 16:30~ D002 | 01/23 Waiting for Signature D002 | Not Completed |
| 003025478 | SURGERY- SCHEDULED PATIENT | D003 D005 D027 D042 | 01/24 Appendicitis D003 | 01/24 1/27 - 2/10 Room 503: 4 Beds | 01/24 CT: Non-tested HM, US: Confirmed | 01/24 Local D005 | 01/25 Confirmed D003 | 01/24 1/29 13:30~ D003 | | 01/24 1/24 D003 |

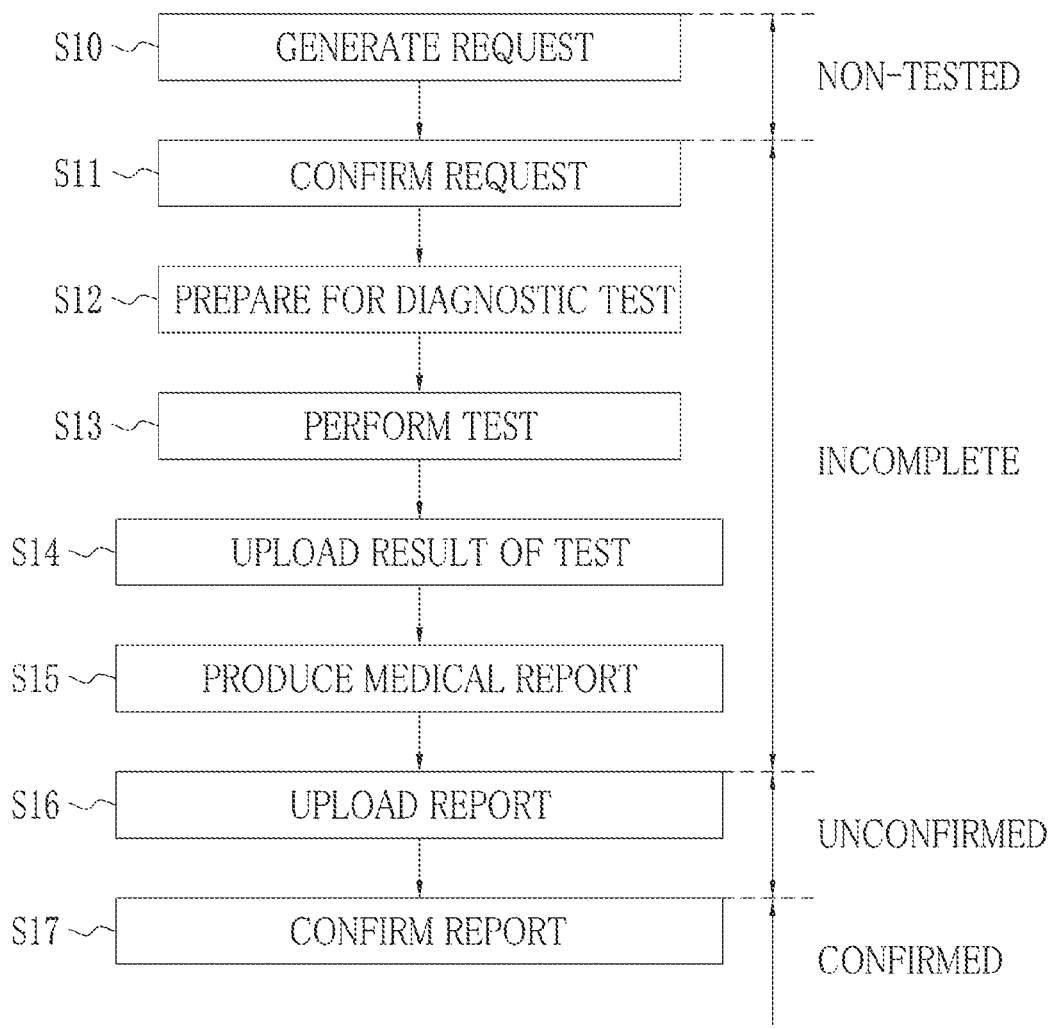

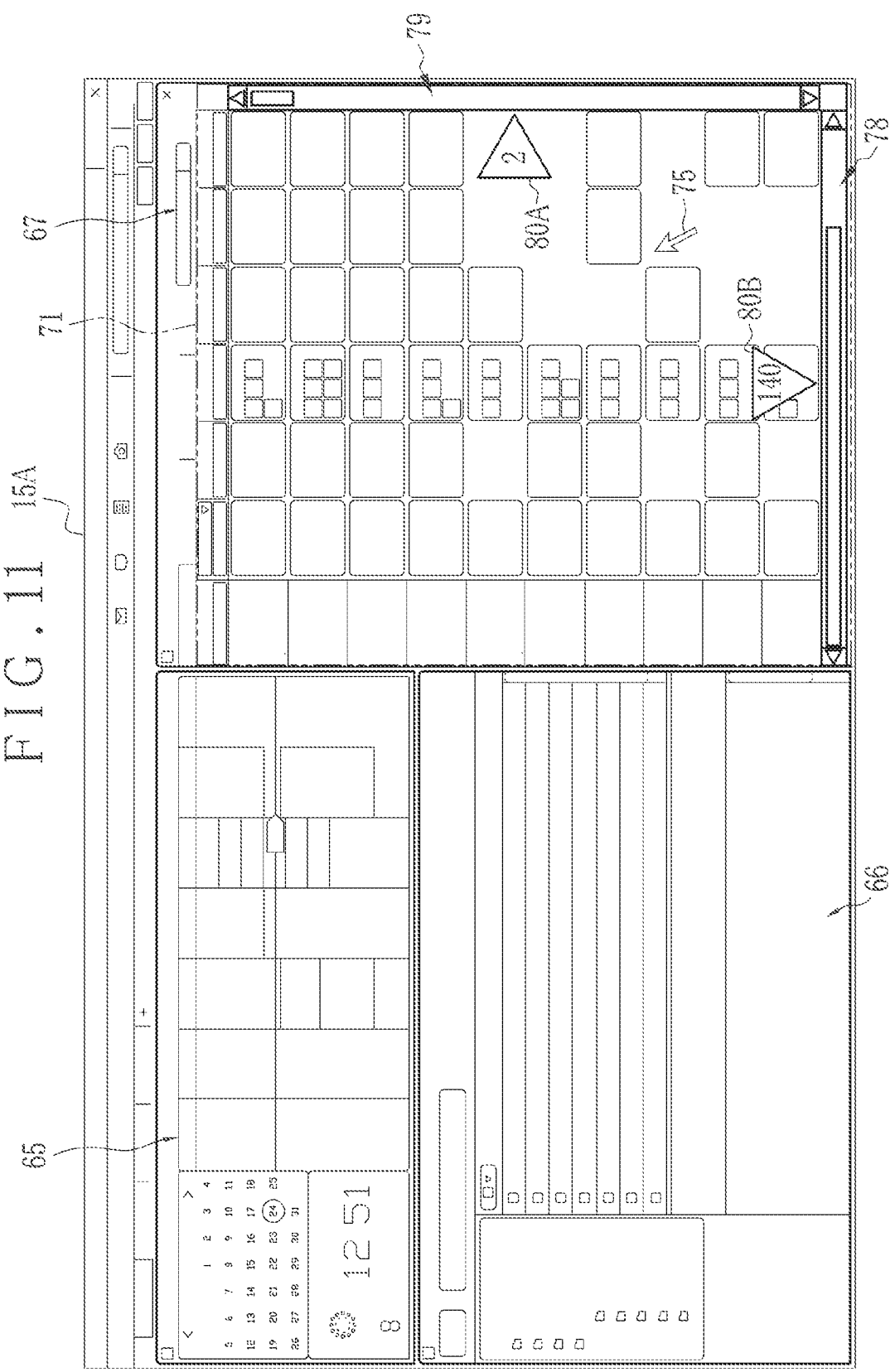

F I G . 15B
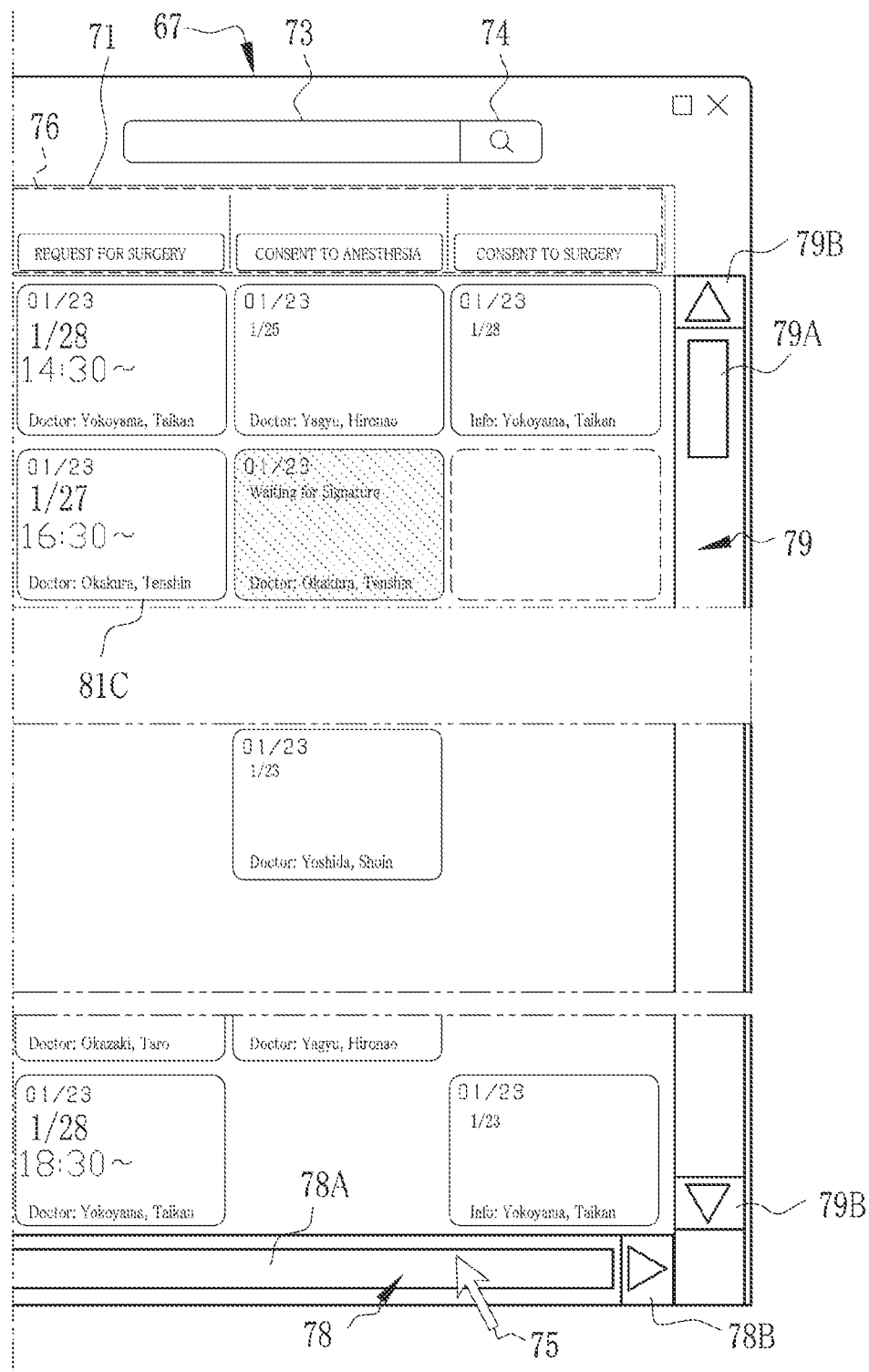

F I G. 16

| PATIENT TYPE | PROFESSIONAL TYPE | INFO ITEMS |
|---|---|---|
| SURGERY-SCHEDULED PATIENT | DOCTOR | Symptom name, scheduling of hospitalization, diagnostic test, request for anesthesia, preoperative summary, request for surgery, consent to anesthesia & consent to surgery |
| | TECHNICIAN | Symptom name, scheduling of hospitalization, diagnostic test, request for anesthesia, preoperative summary & request for surgery |
| | NURSE | Symptom name, scheduling of hospitalization, diagnostic test, request for anesthesia, preoperative summary, request for surgery, consent to anesthesia & consent to surgery |
| | DIETICIAN | |
| OUT-PATIENT | DOCTOR | Symptom name, diagnostic test & patient referral |
| | TECHNICIAN | Symptom name, diagnostic test & patient referral |
| | NURSE | Symptom name, diagnostic test & patient referral |
| | DIETICIAN | |
| IN-PATIENT | DOCTOR | Symptom name, meal, scheduling of hospitalization, diagnostic test, request for surgery, patient care plan, anti-bedsore plan, nutrition plan, follow-up plan & post-discharge summary |
| | TECHNICIAN | Symptom name, scheduling of hospitalization, diagnostic test & request for surgery |
| | NURSE | Symptom name, meal, scheduling of hospitalization, diagnostic test, request for surgery, patient care plan, anti-bedsore plan, nutrition plan & follow-up plan |
| | DIETICIAN | Symptom name, meal, scheduling of hospitalization, diagnostic test, request for surgery, patient care plan, nutrition plan & follow-up plan |

FIG. 17A

| | SURGERY-SCHEDULED PATIENT | OUT-PATIENT | IN-PATIENT | | REQUEST FOR SURGERY |
|---|---|---|---|---|---|
| | PATIENT | SCHEDULING FOR HOSPITALIZATION ▽ | SYMPTOM NAME | DIAGNOSTIC TEST | |
| 1 | ○ ▽ M Age 73<br>1941/02/15<br>Akada, Goro<br>0123456789 | 01/23 09:30<br>1/25 –<br>1/31<br>Room 405: Single | 01/23<br>Gastric Cancer<br>Doctor: Yokoyama, Taikan | 01/24<br>DR US HM<br>ES<br>82 | 01/23<br>1/28<br>14:30~<br>Doctor: Yokoyama, Taikan |
| 2 | ○ ▽ M Age 19<br>1995/02/03<br>Iwamoto, Kenji<br>0000003210 | 01/23 09:30<br>1/25 –<br>1/31<br>Room 505: Single | 01/23<br>Infiltrating Carcinoma<br>Doctor: Okakura, Tenshin | 01/24<br>CT DR US<br>HM EC ES ···<br>82 | 01/23<br>1/27<br>16:30~<br>Doctor: Okakura, Tenshin |
| 3 | ○ △ F Age 34<br>1930/12/05<br>Kugayama, Saeko<br>0000254798 | 01/24<br>1/27 –<br>2/10<br>Room 505: 4 Beds | 01/24<br>Appendicitis<br>Doctor: Tobita, Shuzan | 01/24<br>CT HM US<br>82 | 01/24<br>1/29<br>13:30~<br>Doctor: Tobita, Shuzan |

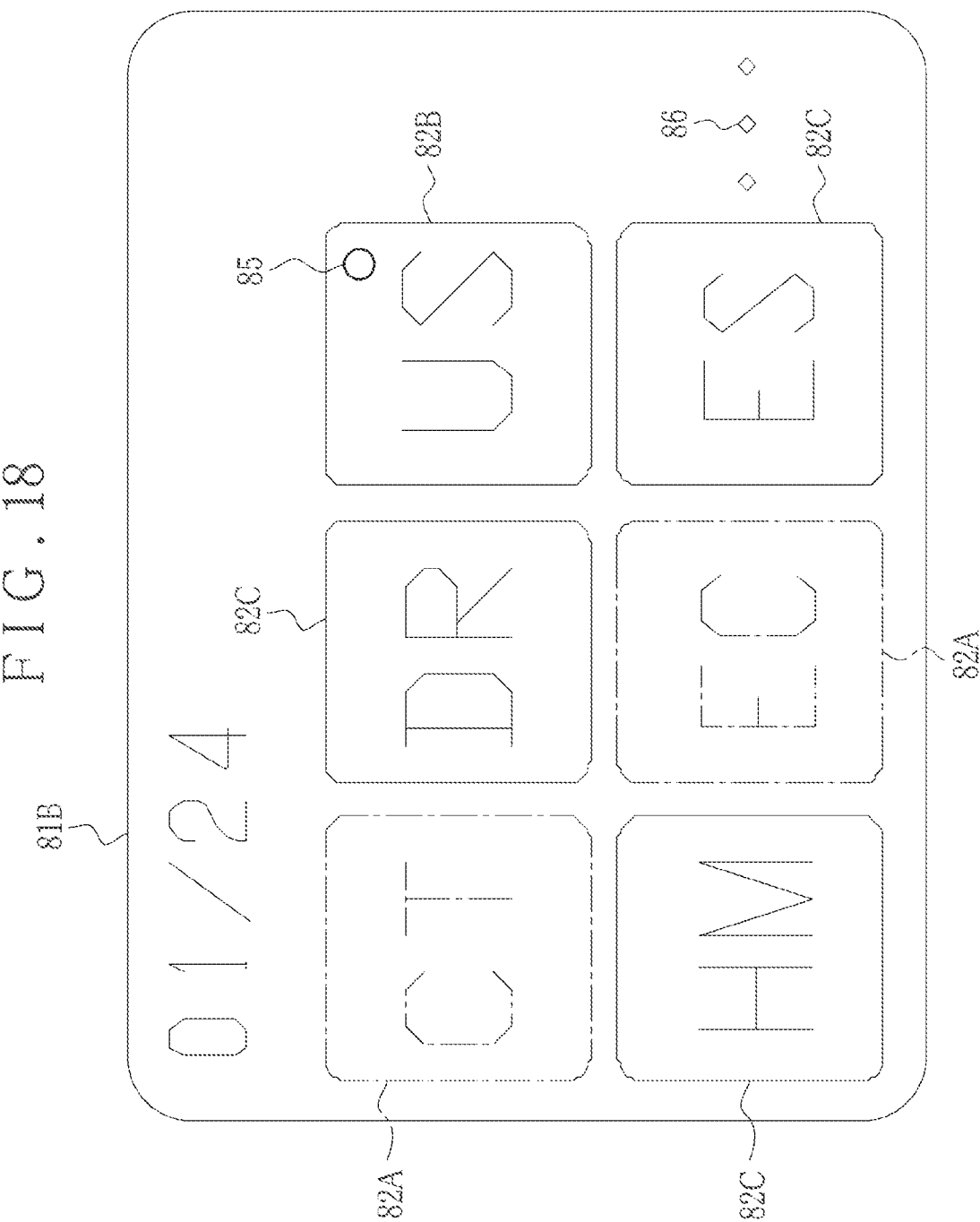

FIG. 19

| PATIENT | PREOPERATIVE SUMMARY | REQUEST FOR SURGERY | CONSENT TO ANESTHESIA | CONSENT TO SURGERY |
|---|---|---|---|---|
| 1 ○▽ M Age 73<br>1941/02/15<br>Akada, Goro<br>0123456789 | 01/23<br>Confirmed<br><br>Doctor: Yokoyama, Taikan | 01/23<br>1/28<br>14:30–<br>Doctor: Yokoyama, Taikan | 01/23<br>1/25<br><br>Doctor: Yagyu, Hironao | 01/23<br>1/23<br><br>Info: Yokoyama, Taikan |
| 2 ○▽ M Age 19<br>1995/02/03<br>Iwamoto, Kenji<br>0000003210 | 01/20<br>Interrupted Due to Liver Metastasis…<br>Doctor: Okakura, Tenshin  81CB | 01/23<br>1/27<br>16:30–<br>Doctor: Okakura, Tenshin | 01/23<br>Waiting for Signature<br>Doctor: Okakura, Tenshin  81CB | |
| 3 ○△ F Age 34<br>1980/12/05<br>Kugayama, Saeko<br>0000254798 | 01/25<br>Confirmed<br><br>Doctor: Tobita, Shuzan | 01/24<br>1/29<br>13:30–<br>Doctor: Tobita, Shuzan | | 01/24<br>1/24<br><br>Info: Tobita, Shuzan  81CA |

| PATIENT | SCHEDULING OF HOSPITALIZATION | SYMPTOM NAME | DIAGNOSTIC TEST | REQUEST FOR ANESTHESIA | PREOPERATIVE SUMMARY | REQUEST FOR SURGERY |
|---|---|---|---|---|---|---|
| 1. ♂ M Age 73 1941/02/15 Akada, Goro 0123456789 | 01/23 09:30 01/25~ 1/30 Room 405: Single | 01/23 Gastric Cancer Doctor: Yokoyama, Taikan | 01/24 DR US HM ES | 01/23 General Doctor: Yagyu, Hironao | 01/23 Confirmed Doctor: Yokoyama, Taikan | 01/23 1/23 14:30~ Doctor: Yokoyama, Taikan |
| 2. ♂ M Age 19 1995/02/03 Iwamoto, Kenji 0000003210 | 01/23 09:30 1/25~ 1/31 Room 505: Single | 01/23 Infiltrating Carcinoma Doctor: Okakura, Tenshin | 01/24 CT DR US HM EC ES | 01/23 General Doctor: Yagyu, Hironao | 01/20 Interrupted Due to Liver Metastasis... Doctor: Okakura, Tenshin | 01/23 1/27 16:30~ Doctor: Okakura, Tenshin |
| 3. ♀ F Age 34 1980/12/05 Kugayama, Saeko 0000254798 | 01/24 1/27~ 2/10 Room 503: 4 Beds | 01/24 Appendicitis Doctor: Tobita, Shuzan | 01/24 CT HM US | 01/24 Local Doctor: Yagyu, Hironao | 01/25 Confirmed Doctor: Tobita, Shuzan | 01/24 1/29 13:30~ Doctor: Tobita, Shuzan |
| 4. ♀ F Age 25 1989/04/02 Koda, Fumie 0000078632 | 01/23 1/30~ 2/15 Room 503: 4 Beds | 01/23 Rectal Cancer Doctor: Yokoyama, Taikan 81A | 01/24 DR US HM ES | 01/23 Local Doctor: Yagyu, Hironao | 01/20 Confirmed Doctor: Okazaki, Taro | 01/23 2/2 17:00~ Doctor: Okazaki, Taro |
| 5. ♂ M Age 34 1980/10/06 Sasaki, Takurota 0123456789 | 01/23 1/30~ 2/15 Room 602: 4 Beds | | 01/24 US HM ES | 01/23 General Doctor: Yagyu, Hironao | | 81C 75 79 |

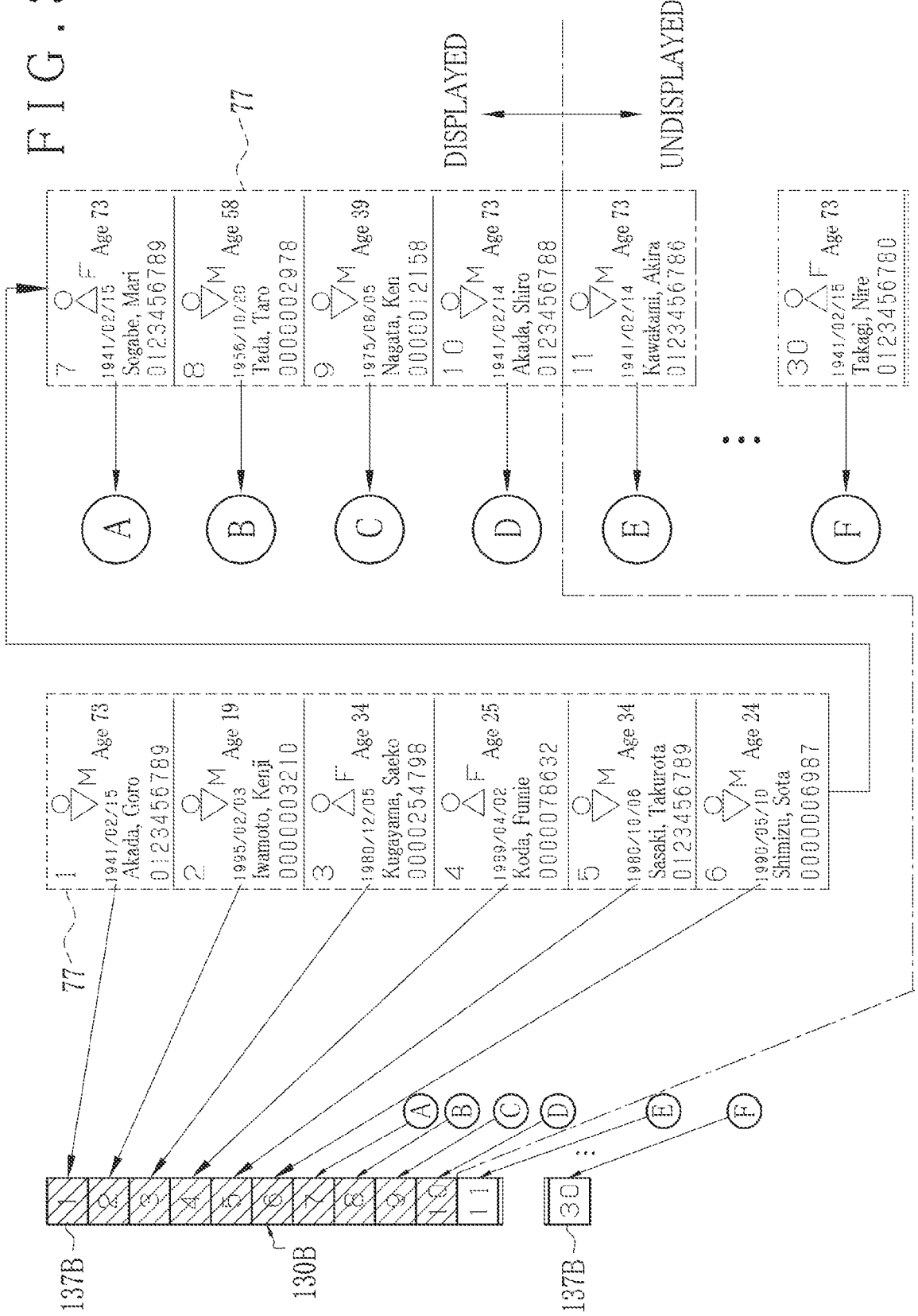

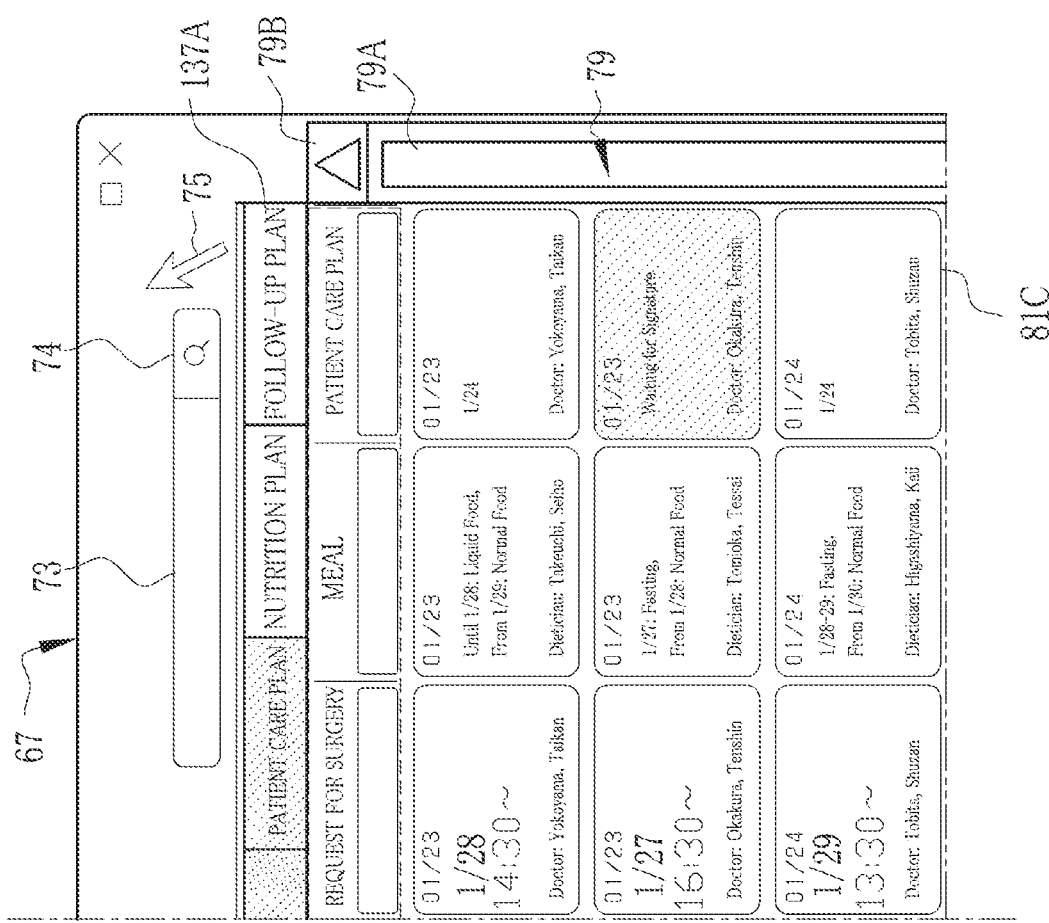

FIG. 33A

| | | SURGERY-SCHEDULED PATIENT | OUT-PATIENT | IN-PATIENT | |
|---|---|---|---|---|---|
| | | SCHEDULING OF HOSPITALIZATION | SYMPTOM NAME | DIAGNOSTIC TEST | REQUEST FOR ANESTHESIA | PREOPERATIVE |
| | PATIENT | SCHEDULING OF HOSPITALIZATION ▽ | SYMPTOM NAME | DIAGNOSTIC TEST |
| 1 | 1 ▽M Age 73<br>1941/02/15<br>Akada, Goro<br>0123456789 | 01/23 09:30<br>1/25 -<br>1/31<br>Room 405: Single | 01/23<br>Gastric Cancer<br><br>Doctor: Yokoyama, Taikan | 01/24<br>DR US HM<br>ES |
| 2 | 2 ▽M Age 19<br>1995/02/03<br>Iwamoto, Kenji<br>0000003210 | 01/23 09:30<br>1/25 -<br>1/31<br>Room 505: Single | 01/23<br>Infiltrating Carcinoma<br><br>Doctor: Okakura, Tenshin | 01/24<br>CT DR US<br>HM EC ES |
| 3 | 3 △F Age 34<br>1980/12/05<br>Kugayama, Saeko<br>0000254798 | 01/24<br>1/27 -<br>2/10<br>Room 503: 4 Beds | 01/24<br>Appendicitis<br><br>Doctor: Tobita, Shuzan | 01/24<br>CT HM US |
| 4 | 4 △F Age 25<br>1989/04/02<br>Koda, Fumie<br>0000078632 | 01/23 09:30<br>1/30 -<br>2/15<br>Room 503: 4 Beds | 01/23<br>Rectal Cancer<br><br>Doctor: Yokoyama, Taikan | 01/24<br>DR US HM<br>ES |
| 30 | Akada, Shiro<br>0123456788 | 2/20<br>Room 604: Single | | |

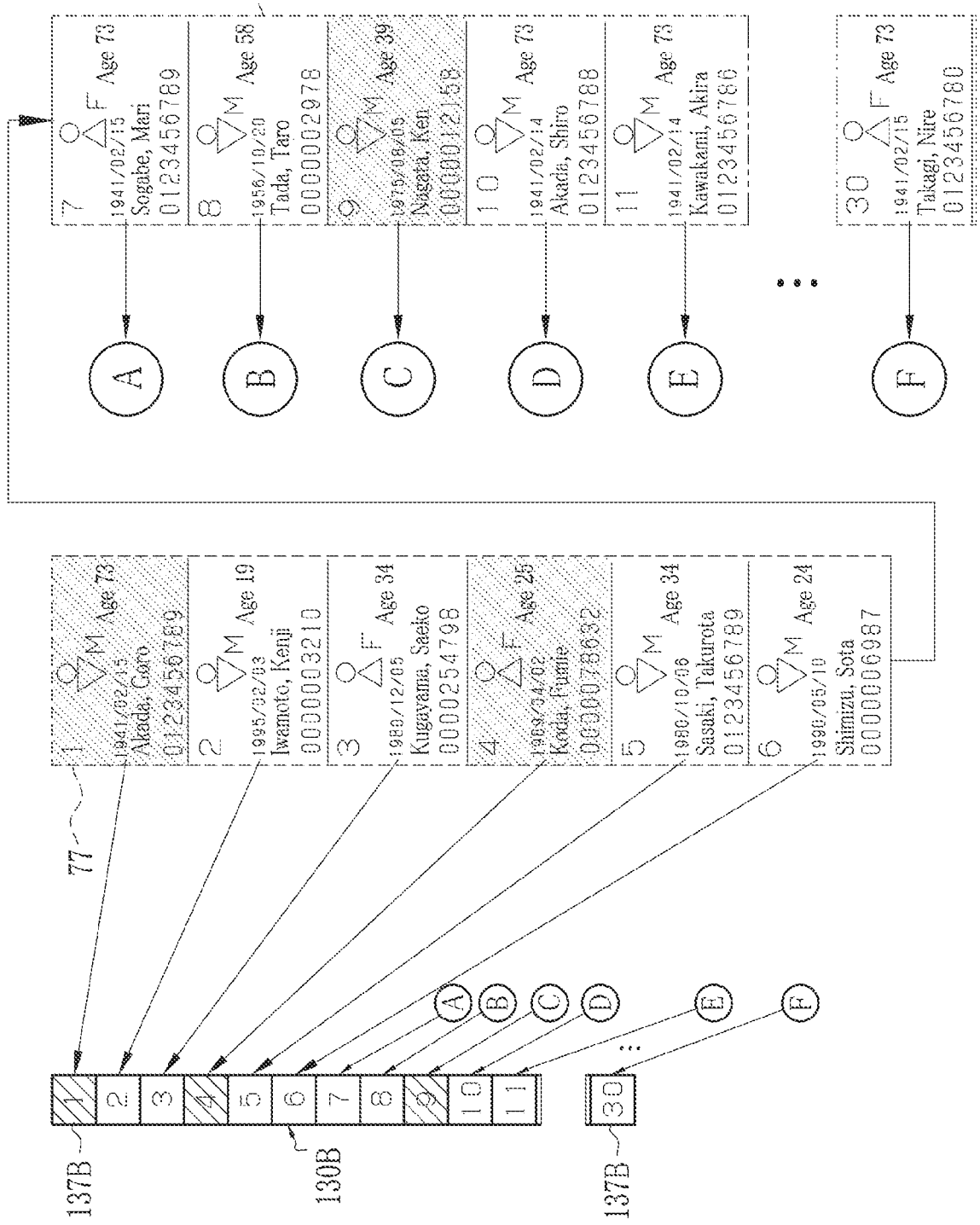

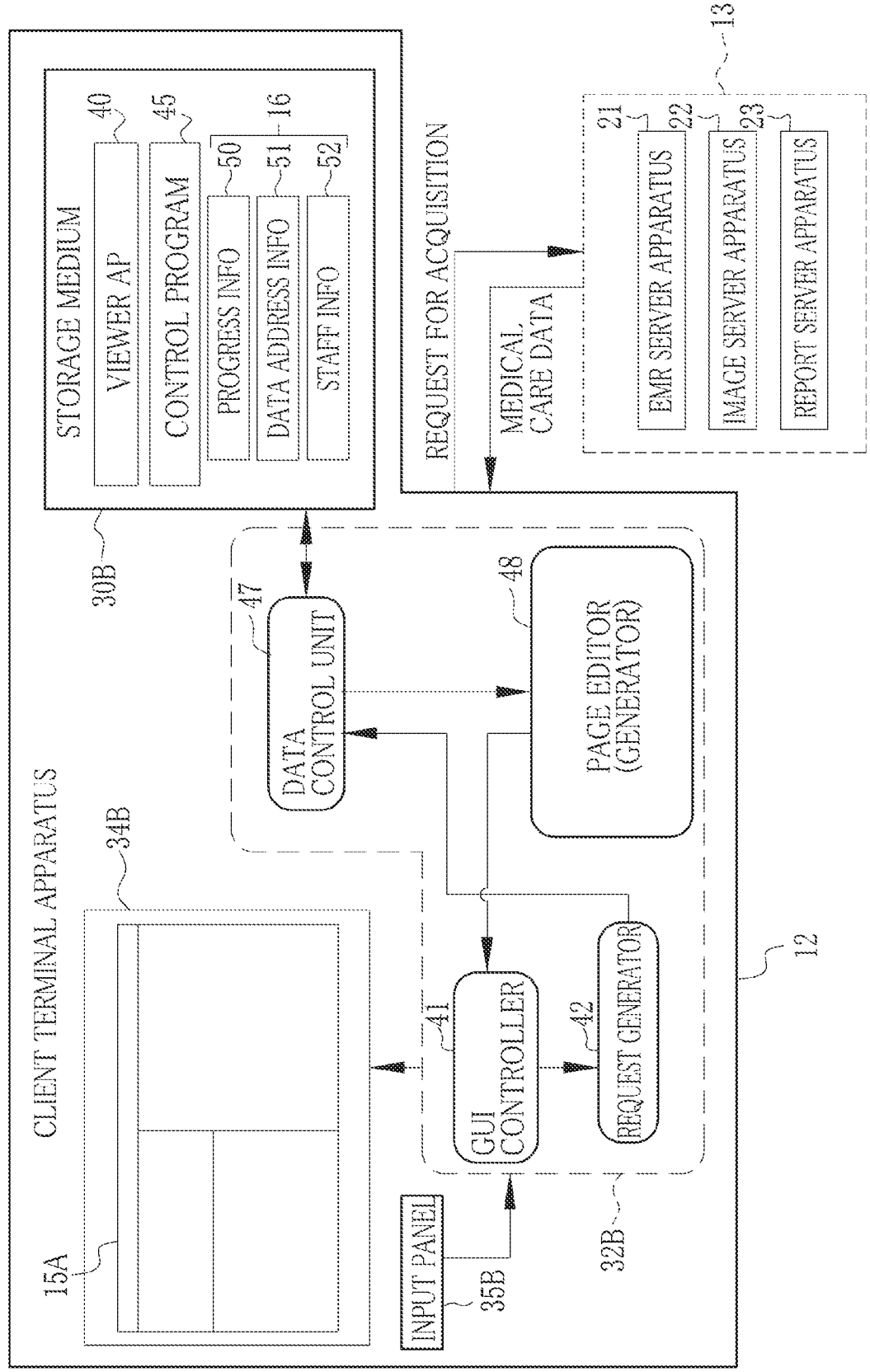

MEDICAL SUPPORT APPARATUS, METHOD AND SYSTEM FOR MEDICAL CARE

CROSS-REFERENCE TO RELATED APPLICATION

This application claims priority under 35 USC 119 from Japanese Patent Application No. 2015-017943, filed 30 Jan. 2015, and Japanese Patent Application No. 2015-017944, filed 30 Jan. 2015, the disclosure of which is incorporated by reference herein.

BACKGROUND OF THE INVENTION

1. Field of the Invention

The present invention relates to a medical support apparatus, method and system for medical care. More particularly, the present invention relates to a medical support apparatus, method and system for medical care, in which a patient list on a display panel can be viewed by a medical professional easily with good visual perceptibility.

2. Description Related to the Prior Art

A patient list or work list in the field of the medicine is known. Medical professionals (medical staff members) view the patient list for aid in medical care for patients (patient bodies), including a doctor, a nurse, and a technician for performing a diagnostic test of the patient. In the patient list, a two-dimensional area is defined by a first axis for plural information items related to the medical care of the patients and a second axis for a case ID or identification data of the plural patients. Content of the items of the patients is indicated in the two-dimensional area.

JP-A 2006-338521 discloses a medical support apparatus (management server) for creating an information page, which has the patient list with information items of clinical processes (medical care processes) from the professionals to a patient in relation to medical care, such as check-up and the diagnostic test. The medical support apparatus outputs the information page to a client terminal apparatus at each of the professionals. The client terminal apparatus causes a display panel to display the information page for the professional to view the same.

In JP-A 2006-338521, the information items are arranged along a horizontal axis. The case IDs (patient Nos.) are arranged along a vertical axis. Examples of the information items are such related to the diagnostic test of ophthalmology, including visual acuity test, checking dilation of the pupil, eye fundus imaging, non-contact tonometry, and the like, and also the clinical process other than the diagnostic test, including consultation, treatment, payment and the like. Icons (status marks) are disposed in the information items of the clinical process for expressing the progress of the clinical process.

The information page in JP-A 2006-338521 displays part of the above-described information items. Remaining information items among the information items are undisplayed as the information page cannot contain the remaining information items. A horizontal scroll bar is provided in the patient list for redisplaying the undisplayed remaining information items. Also, a vertical scroll bar is provided in the patient list for scroll patients particularly at the time of occurrence of undisplayed patients among all the patients with the case ID in relation to the information page.

Each scroll bar includes a slider and two arrow buttons. The slider is movable longitudinally. The arrow buttons are disposed at ends of the slider. In case a data amount of an active display area is larger than a data amount of an undisplayed portion, an area of the slider relative to the entirety of the scroll bar is large. In case the data amount of the undisplayed portion is larger than the data amount of the active display area, the area of the slider relative to the entirety of the scroll bar is small. The undisplayed portion can become displayed by an input action for scroll, such as press of the slider or arrow buttons with a mouse cursor, or rotation of a wheel button in the mouse.

Assuming that the undisplayed portion is created without entire containment of the information items or the case ID of the patient list in the information page, a well-known method of scroll as disclosed in JP-A 2006-338521 is used for redisplaying the undisplayed portion by an input action for the scroll.

A display form having the scroll bars as disclosed in JP-A 2006-338521 enables recognition of an estimated data amount of the undisplayed portion by use of the area of the slider relative to the entire area of the scroll bars. Also, data amounts of the active display area and the undisplayed portion (ratio) and an estimated entire data amount of the patient list in combination of the active display area and the undisplayed portion can be recognized. However, it is impossible to recognize the number of information items in the undisplayed portion, or the number of datasets of the case ID in the undisplayed portion (number of patients of whom the case ID is included in the undisplayed portion), or the data amount of the undisplayed portion. Furthermore, the exact data amount of the active display area and the undisplayed portion and the entire data amount of the patient list cannot be recognized.

In case a professional does not recognize the data amount of the undisplayed portion, or the data amount of the entirety of the patient list in combination with the data amounts of the active display area and the undisplayed portion, he or she cannot find user accessibility or time related to viewing the patient list. There arises a serious problem in visual perceptibility and interface functionality in the medical support apparatus to professionals to perform busy tasks of medical care.

SUMMARY OF THE INVENTION

In view of the foregoing problems, an object of the present invention is to provide a medical support apparatus, method and system for medical care, in which a patient list on a display panel can be viewed by a medical professional easily with good visual perceptibility.

In order to achieve the above and other objects and advantages of this invention, a medical support apparatus includes a page generator for generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. A display processor is operable in response to an input action for scroll, for display processing to change over an undisplayed portion to a display state for view assuming that at least one of a partial information item among the plural information items and partial identification data among the plural identification data is in the undisplayed portion hidden from the information page. The display processor performs display processing to display at least one of first and second number data in the information page, the first number data being a number of the partial information item, the second number data being a number of the partial identification data.

Preferably, the first or second number data is indicated in a translucent form in the patient list.

Preferably, the first or second number data is deleted from the information page upon occurrence of an action for scroll.

Preferably, the first or second number data is displayed in a number window area for indicating a hidden form of the undisplayed portion.

Preferably, the number window area is shaped to project in one direction, and points a direction associated with the undisplayed portion.

Preferably, the information items include an information item of a clinical process performed by a medical professional for the patient bodies.

Preferably, at least one icon portion is displayed in the patient list. The icon portion is arranged in one or more arrays, displayed in relation to the clinical process of which a schedule is registered, for expressing the information item graphically.

Preferably, the icon portion expresses progress of the clinical process, and has a display form changeable with a change in the progress.

Preferably, the patient list is generated for each one of plural professionals, and at least one of the information items, the identification data and the progress is different between the professionals in relation to the plural patient bodies and the clinical process.

Preferably, the patient list is generated according to one of plural patient types of the patient bodies, and at least one of the information items, the identification data and the progress is different between the patient types.

Preferably, the patient type is a selected one of a surgery-scheduled patient for whom a surgery is scheduled, an out-patient and an in-patient.

Preferably, the display processor performs display processing of at least one of first and second data list areas in the information page, the first data list area has an array of first block cells of which a number is equal to a total of the information items included in an active display area of the information page and the undisplayed portion, and the second data list area has an array of second block cells of which a number is equal to a total of the identification data included in the active display area and the undisplayed portion.

Preferably, at least one of the first block cells corresponding to the active display area is displayed distinctly from at least one of the first block cells corresponding to the undisplayed portion. At least one of the second block cells corresponding to the active display area is displayed distinctly from at least one of the second block cells corresponding to the undisplayed portion.

Preferably, one of the first block cells corresponding to one of the information items set in an alert condition is displayed in an emphasized form in the first data list area. One of the second block cells corresponding to the identification data of one of the patient bodies set in an alert condition is displayed in an emphasized form in the second data list area.

Preferably, an information item corresponding to the emphasized first block cell among the information items arranged along the first axis is displayed in an emphasized form. Identification data corresponding to the emphasized second block cell among the identification data arranged along the second axis is displayed in an emphasized form.

Preferably, the first data list area extends in a direction of the first axis along arrangement of the information items, and the second data list area extends in a direction of the second axis along arrangement of the identification data.

Preferably, alphanumeric information expressing the information items is indicated in the first block cells, and alphanumeric information expressing the identification data is indicated in the second block cells.

Also, a medical support method includes a step of generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. An undisplayed portion is changed over to a display state for view in response to an input action for scroll assuming that at least one of a partial information item among the plural information items and partial identification data among the plural identification data is in the undisplayed portion hidden from the information page. At least one of first and second number data is displayed in the information page, the first number data being a number of the partial information item, the second number data being a number of the partial identification data.

Also, a medical support system including a medical support apparatus, and a client terminal apparatus connected with the medical support apparatus communicably by network connection is provided. A page generator generates an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. A display processor is operable in response to an input action for scroll, for display processing to change over an undisplayed portion to a display state for view assuming that at least one of a partial information item among the plural information items and partial identification data among the plural identification data is in the undisplayed portion hidden from the information page. The display processor performs display processing to display at least one of first and second number data in the information page, the first number data being a number of the partial information item, the second number data being a number of the partial identification data.

Consequently, a patient list on a display panel can be viewed by a medical professional with good visual perceptibility, because number data of the information items and identification data are displayed irrespective of the undisplayed portion outside an active display area.

BRIEF DESCRIPTION OF THE DRAWINGS

The above objects and advantages of the present invention will become more apparent from the following detailed description when read in connection with the accompanying drawings, in which:

FIG. 4 is a data chart illustrating a structure for storing medical reports;

FIG. 6 is a block diagram schematically illustrating circuit devices in a CPU in the computer;

FIG. 7 is a table illustrating information of progress;

FIG. 8 is a flow chart illustrating a flow of a diagnostic test and its progress;

FIG. 9 is a data chart illustrating a structure for storing data addresses;

FIGS. 11 and 11A are a screen view illustrating a first information page;

FIG. 12 is an explanatory view illustrating an upper portion of a patient list area;

FIGS. 13, 13A and 13B are a screen view illustrating the patient list area;

FIGS. 15, 15A and 15B are a screen view illustrating the patient list area after scroll to the right;

FIG. 16 is a type mapping table illustrating various data related to patient types and professional types;

FIGS. 17, 17A and 17B are a screen view illustrating a patient list on a condition of an in-patient and a dietician;

FIG. 18 is an explanatory view illustrating information of the progress with a small icon;

FIG. 19 is a screen view illustrating information of the progress with a normal icon;

FIGS. 26, 26A and 26B are a screen view illustrating the floating window in one example of a location;

FIGS. 28, 28A and 28B are a screen view illustrating a second preferred patient list;

FIG. 30 is an explanatory view illustrating a relationship between personal information and second block cells;

FIGS. 31, 31A and 31B are a screen view illustrating the patient list after scroll to the right;

FIGS. 32, 32A and 32B are a screen view illustrating a patient list on the condition of the in-patient and the dietician;

FIGS. 33, 33A and 33B are a screen view illustrating a third preferred patient list having a setting in an alert condition;

FIG. 34 is an explanatory view illustrating a relationship between the personal information and the second block cells;

FIG. 36 is a block diagram schematically illustrating an example in which a client terminal apparatus is functioned as a medical support apparatus.

DETAILED DESCRIPTION OF THE PREFERRED EMBODIMENT(S) OF THE PRESENT INVENTION

Figure 1:
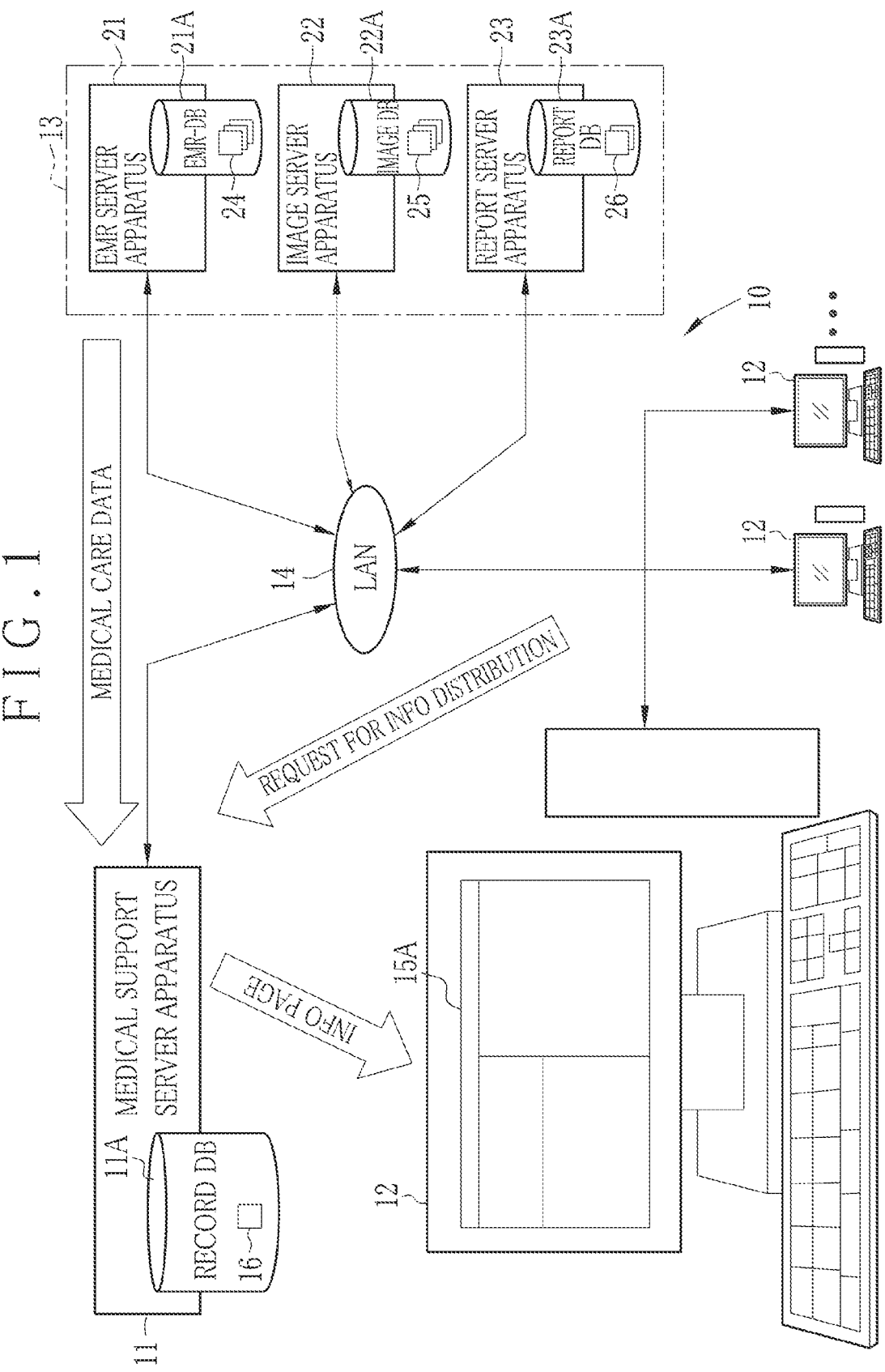
FIG. 1 is a block diagram schematically illustrating a medical support system.

In FIG. 1, a medical support system 10 (clinical decision support system) is a computer system for medical support in a hospital facility. The medical support system 10 includes a medical support server apparatus 11, client terminal apparatuses 12 and a server cluster 13. A LAN 14 or local area network is installed in a site of the hospital facility, and interconnects those apparatuses in a communicable manner.

The medical support server apparatus 11 functions as a medical support apparatus of the invention. The medical support server apparatus 11 acquires medical care data from the server cluster 13 as a result of medical care of a patient, and creates a first information page 15A (in FIGS. 11 and 11A) and a second information page 15B (in FIG. 20) according to the acquired medical care data. The medical support server apparatus 11 performs information distribution of the first and second information pages 15A and 15B to the client terminal apparatuses 12. In FIG. 1, the first information page 15A is illustrated.

A record database 11A (DB) for pages is combined with the medical support server apparatus 11, and stores record information 16 for the pages. The medical support server apparatus 11 generates and edits the first and second information pages 15A and 15B by referring to the record information 16.

The client terminal apparatus 12 is disposed in each one of hospital departments, such departments as internal medicine, surgery, otolaryngology and ophthalmology for medical care, and such departments as a radiology department and clinical testing department for diagnostic tests. The client terminal apparatus 12 is manually operated by each one of medical professionals (medical staff members), such as doctors, technicians, nurses, dieticians and the like. The client terminal apparatus 12 displays the first and second information pages 15A and 15B distributed by the medical support server apparatus 11, for use in medical care of professionals. The client terminal apparatus 12 is a viewer terminal apparatus for viewing the first and second information pages 15A and 15B.

The medical support server apparatus 11 distributes the first and second information pages 15A and 15B to the client terminal apparatus 12 in a format of XML data for web distribution created according to the XML (Extensible Markup Language) as a markup language. The client terminal apparatus 12 performs display processing to display the first and second information pages 15A and 15B on the web browser according to the XML data. Also, it is possible to use another data description language instead of the XML, such as JSON (JavaScript Object Notation) and the like, JavaScript being a trade name.

The server cluster 13 searches medical care data according to a request for acquisition from the medical support server apparatus 11, and transmits acquired medical care data to the medical support server apparatus 11. The server cluster 13 includes an EMR server apparatus 21 or electronic chart server apparatus, an image server apparatus 22, and a report server apparatus 23.

An EMR database 21A (DB) or chart database is combined with the EMR server apparatus 21, and stores EMRs 24 (electronic medical records) or electronic charts. Medical care data are recorded in the EMRs 24, and include patient visit data (consultation data), diagnostic test data, measurement data, request data, treatment progress data and payment data. Examples of the patient visit data include results of questionnaire, finding of progress, symptom name and the like. Examples of the diagnostic test data include test values of diagnostic tests, such as a blood test, biochemical test and other sample tests, electrocardiography (ECG), and electroencephalography (EEG) and other physiological tests. Examples of the measurement data include measurement values of vital signs, such as respiration rate, heart rate, blood pressure, body temperature and the like. Examples of the request data are for requesting a diagnostic test, treatment, surgery, drug administration and the like. Examples of the treatment progress data include event information of medical processes (events) of a patient body, such as a first consultation, hospitalization, hospital discharge, rehospitalization, treatment, surgery, drug administration, complete cure and the like. Examples of the payment data include a clinical cost, drug cost, cost of hospitalization and the like. The various data in the EMRs 24 can be input by the client terminal apparatus 12. Also, the EMRs 24 can be viewed and read by the client terminal apparatus 12.

The image server apparatus 22 is a PACS server (Picture Archiving and Communication System). An image database 22A (DB) is combined with the image server apparatus 22, and stores diagnostic images 25. Examples of the diagnostic images 25 are those formed by the CT (Computed Tomography), MRI (Magnetic Resonance Imaging), X-ray imaging, ultrasonography, endoscopy and other medical imaging. The diagnostic images 25 are produced in a data file format of the DICOM (Digital Imaging and Communication in Medicine). The diagnostic images 25 can be viewed by use of the client terminal apparatus 12.

A report database 23A (DB) is combined with the report server apparatus 23, and stores medical reports 26. The medical reports 26 are a document produced by a radiologist as a result of interpreting the diagnostic images 25 formed by the imaging. The medical reports 26 are produced by use of the client terminal apparatus 12, and can be viewed with the client terminal apparatus 12.

A case ID (identification data) for identifying a patient is associated as meta information with each one of the EMRs 24, the diagnostic images 25 and the medical reports 26. See FIGS. 2-4. A professional ID (staff member ID) as meta information is associated with the EMRs 24 for identifying a medical transcriptionist or secretary having input medical care data (staff member ID for a staff member). A professional ID as meta information is associated with the diagnostic images 25 for identifying a technician having performed a diagnostic test. A professional ID as meta information is associated with the medical reports 26 for identifying a radiologist having produced the medical reports 26. The professional ID makes it possible to recognize who has performed a particular clinical process (medical care process) among the professionals. An example of the professional ID is a number or sign for identification of each professional. The EMRs 24, the diagnostic images 25 and the medical reports 26 can be searched from the EMR database 21A, the image database 22A and the report database 23A by use of a search query of meta information such as a case ID.

Figure 2:
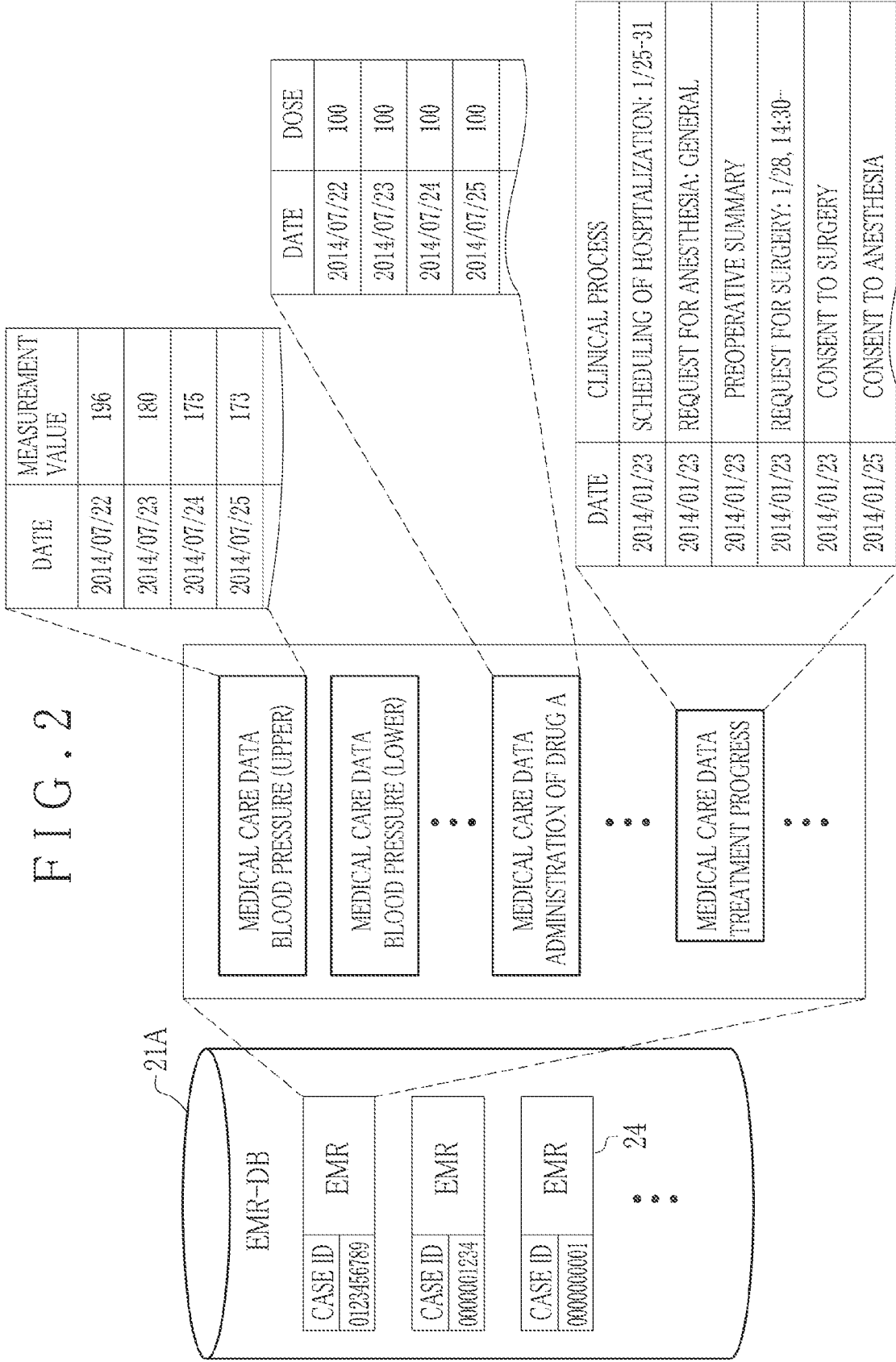
FIG. 2 is a data chart illustrating a structure for storing EMRs.

In FIG. 2, the EMRs 24 stored in the EMR database 21A are managed by the unit of patients (patient bodies) in association with a case ID including 10 digits, such as "0123456789". The EMRs 24 contain the case ID, personal information and medical care data of plural information items. The personal information includes a name, sex, birthday, age and the like of each patient. The medical care data are recorded according to a time sequence in an arranged manner of a blood pressure (upper), blood pressure (lower), biochemical test A, progress note and the like. Further examples of the medical care data, which are not shown in FIG. 2, include the progress note data, measurement data of vital signs such as a heart rate, respiration rate and body temperature in addition to the blood pressure, request data and payment data.

A record of one case of information items in the medical care data includes date/time information, such as a date/time of a patient visit, a date/time of a diagnostic test, a date/time of measurement, a date/time of drug administration (date/time of its use or date/time of the administration), and dates/times of various medical events in the course of medical care of the patient, and patient health information, such as content of questionnaire, a result of diagnosis, a test value, a measurement value, dose of a drug, payment information, and medical events. Assuming that the information item is the drug administration, an example of the drug administration at one time may be "dose of a particular amount per one day and continuation for five days", because effect of the drug administration may require a certain period. For this example, a date/time scheduled for the use of the drug is recorded as the date/time of the drug administration.

Examples of the medical events related to the treatment progress data are hospitalization, surgery, conversion between the hospital departments, hospital discharge, rehospitalization and the like. Further examples of data in the treatment progress data are details of scheduling of the hospitalization, details of a request for anesthesia, preoperative summary, details of a request for a surgery, patient consent to the anesthesia, patient consent to the surgery, and the like in relation to the surgery. The preoperative summary is a summary of the result of the diagnostic test (check-up) before the surgery. The patient consent to the anesthesia and patient consent to the surgery are documents with brief descriptions for the anesthesia and surgery and a signature or seal of the patient or his or her family member after providing sufficient information of necessity and risk of the anesthesia and surgery.

Figure 3:
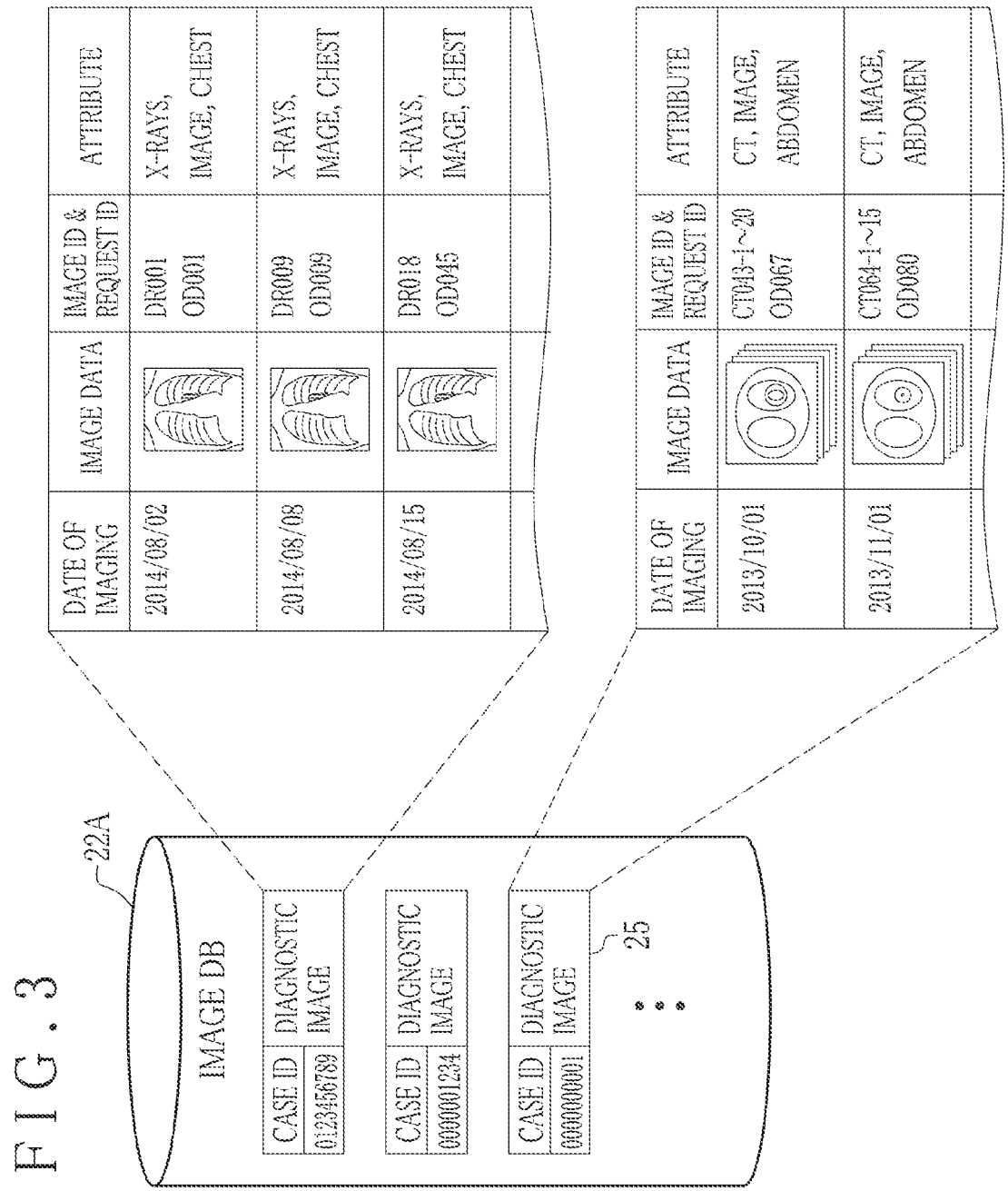
FIG. 3 is a data chart illustrating a structure for storing diagnostic images.

In FIG. 3, the diagnostic images 25 stored in the image database 22A are managed by the unit of the patients in association with the case ID in the same manner as the EMRs 24. Attributes of the diagnostic images 25 are meta information associated with image data of the diagnostic images 25 in addition to the case ID, and include a date of the imaging (date of uploading the image database 22A with the diagnostic images 25), image ID, request ID, modality of the imaging, such as X-ray, CT and the like, type of the diagnostic images 25, such as an X-ray image and CT image, and body part, such as a chest and abdomen. The image server apparatus 22 transmits the diagnostic images 25 to the medical support server apparatus 11 as medical care data together with the dates of the diagnostic tests and the attributes as meta information.

The image ID is a code with numbers or signs for identification of the diagnostic images 25. The request ID is a code with numbers or signs for identification of each request. In the X-ray imaging, one image is created generally in one diagnostic process of the imaging. In the CT imaging, in contrast, a plurality of the diagnostic images 25 are created in one diagnostic process of imaging. For this case, a common request ID is allocated to the diagnostic images 25 to express that the diagnostic images 25 are derived from the single diagnostic process of imaging. The diagnostic images 25 are managed as one group. This is the same assuming that a plurality of X-ray images are created in one diagnostic process of the imaging.

Also, examples of the meta information of the diagnostic images 25 can include a location and size of a lesion in the diagnostic images 25, a type, feature amount and cure level of the lesion, and the like. Assuming that the imaging is ultrasonography, information of a measurement value of a blood flow obtained by analyzing an ultrasonic image can be included in the meta information.

In FIG. 4, the medical reports 26 stored in the report database 23A are managed by the unit of patients in association with case IDs in the same manner as the EMRs 24 and the diagnostic images 25. Meta information is associated with the medical reports 26, inclusive of the case ID, date and time of updating the medical reports 26 to the report database 23A, report ID of the medical reports 26, image ID and request ID of the diagnostic images 25 attached to report data of the medical reports 26, and attributes in the same manner as the diagnostic images 25. The report server apparatus 23 transmits the medical reports 26 to the medical support server apparatus 11 as medical care data together with the meta information. In FIGS. 2-4, the date is depicted, but the time is not depicted.

Each one of the medical support server apparatus 11, the client terminal apparatus 12 and the server apparatuses 21-23 in the server cluster 13 is constituted by a computer and programs installed therein. Examples of the computer are a personal computer, server computer, workstation and the like. The programs include control programs and application programs. The control programs are an Operating System (OS) and the like. The application programs are client programs, server programs and the like.

Figure 5:
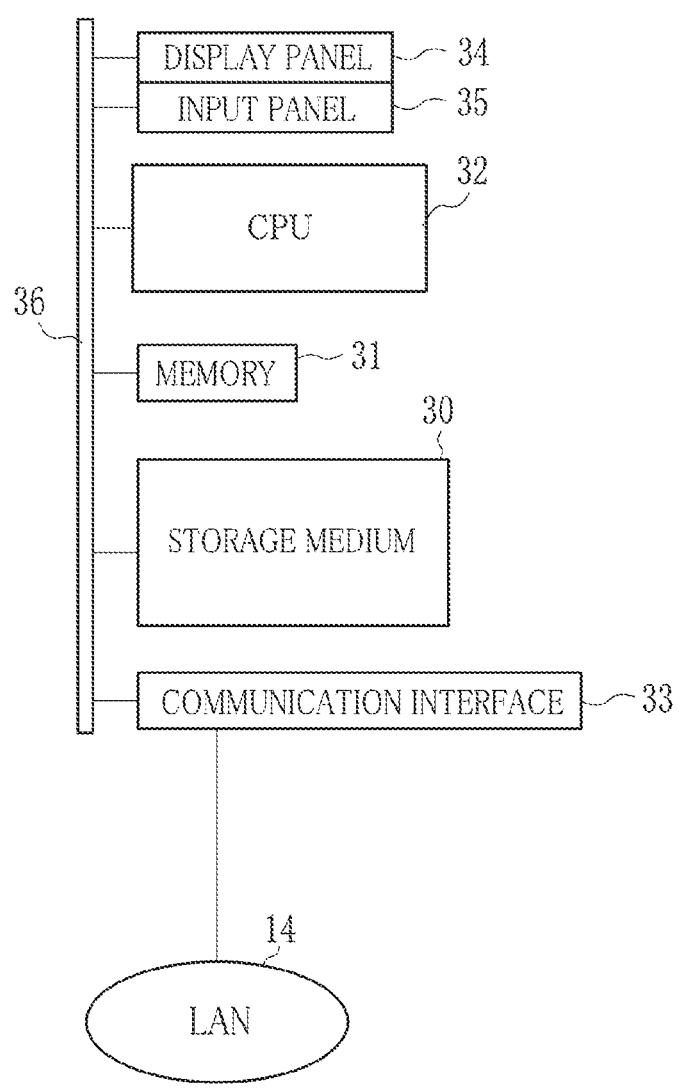
FIG. 5 is a block diagram schematically illustrating a computer constituting each one of terminal apparatuses in the medical support system.

In FIG. 5, computers constituting the medical support server apparatus 11, the client terminal apparatus 12 and the like are basically constructed equally. Each of the computers includes a non-transitory storage medium 30 or storage device, a non-transitory memory 31, a CPU 32 (central processing unit), a communication interface 33, a display panel 34 and an input panel 35. A data bus 36 connects those circuit devices with one another.

The storage medium 30 is a hard disk drive incorporated in the computer constituting the medical support server apparatus 11, the client terminal apparatus 12 or the like or connected to the computer by a cable, network or the like. Also, the storage medium 30 may be a disk array having plural hard disk drives. The storage medium 30 stores a control program and various application programs such as the Operating System (OS), and display page data for control pages associated with the programs.

The memory 31 is a working memory with which the CPU 32 performs tasks. The CPU 32 loads the memory 31 with the programs read from the storage medium 30, and controls the various elements in the computer by processing according to the programs.

The communication interface 33 is a network interface for transmission control of various data by use of the LAN 14. The display panel 34 displays the various control pages according to operation of the input panel 35, such as a mouse, keyboard or the like. A function of input is provided in the control page according to the GUI (Graphical User Interface). The computer for the medical support server apparatus 11, the client terminal apparatus 12 or the like receives inputs of command from the input panel 35 by use of the control page. In the following description, a sign A will be added to each of reference signs of components in the computer constituting the medical support server apparatus 11. A sign B will be added to each of reference signs of components in the computer constituting the client terminal apparatus 12.

In FIG. 6, a non-transitory storage medium 30B or storage device in connection with the client terminal apparatus 12 stores a viewer application 40 or viewer software (application program) for viewing the first and second information pages 15A and 15B. Plural gadgets (gadget engines) are included in the viewer application 40 for display processing of the first and second information pages 15A and 15B with a display panel. The gadgets are subsidiary programs of various functions in combination with main components of application programs included in the viewer application 40.

In case the viewer application 40 is run, a CPU 32B (central processing unit) in the client terminal apparatus 12 cooperates with the non-transitory memory 31, so that a GUI controller 41 and a request generator 42 are ready to operate in the CPU 32B.

The GUI controller 41 performs display processing of the first and second information pages 15A and 15B distributed by the medical support server apparatus 11 so that a display panel 34B displays the first and second information pages 15A and 15B. The GUI controller 41 controls the first and second information pages 15A and 15B according to an input action from an input device 35B, for example, click of a button for a position of a mouse cursor 75 of FIG. 12, and the like.

The request generator 42 receives an input action of the input device 35B by use of the GUI controller 41, and generates various requests for processing to the medical support server apparatus 11. The requests include a request for information distribution of the first information page 15A, and a request for editing of the first and second information pages 15A and 15B. The requests generated by the request generator 42 are transmitted to the medical support server apparatus 11 through the LAN 14.

The request for information distribution includes a professional ID. The professional ID is input together with an authorization key by use of a login page (not shown) for starting up the first information page 15A.

The requests for editing are for instructing the medical support server apparatus 11 to edit the content information of the first and second information pages 15A and 15B according to input actions at the input device 35B. One of the requests for editing may include information of a patient type. Examples of the patient types are a surgery-scheduled patient, out-patient and in-patient among all patients cared in the hospital facility having the medical support system 10. The surgery-scheduled patient is one for whom surgery is scheduled. The out-patient is one visiting the hospital facility repeatedly. The in-patient is one hospitalized in the hospital facility. Note that one patient type may be a patient with a gastric cancer, as a symptom name of a disease, disorder or injury of the patient.

A non-transitory storage medium 30A or storage device stores a control program 45 in the medical support server apparatus 11 as an application. The control program 45 is run for a computer of the medical support server apparatus 11 to function as a medical support apparatus. A CPU 32A in the medical support server apparatus 11 is caused by running the control program 45 to operate with a request receiving unit 46, a data control unit 47 for pages or manager, a page editor 48 or page generator, and a transmission controller 49 or output interface in cooperation with the non-transitory memory 31.

The request receiving unit 46 receives a request for the information distribution and a request for editing from the client terminal apparatus 12. The request receiving unit 46 outputs those received requests to the data control unit 47.

The data control unit 47 manages the record information 16 in the record database 11A. The record information 16 includes progress information 50 of FIG. 7, data address information 51 of FIG. 9, and staff information 52 of FIG. 10. The progress information 50 is information of progress of a clinical process (medical care process) from a professional to a patient and required for creating the first information page 15A. The data address information 51 is information of storage addresses of medical care data, such as addresses for the diagnostic images 25 in the image database 22A and addresses for the medical reports 26 in the report database 23A, and required for creating the second information page 15B. The staff information 52 is information of professionals with settings in the first and second information pages 15A and 15B.

The data control unit 47 sends a request for acquisition to the server cluster 13 periodically, for example, by one hour, to acquire medical care data. In response to the request for acquisition, the data control unit 47 acquires the medical care data transmitted from the server cluster 13, to update the progress information 50 and the data address information 51 according to the medical care data. Also, the data control unit 47 updates the staff information 52 according to the request for editing from the request receiving unit 46. Note that a time interval for generating the request for acquisition can be set with differences between types of the medical care data. For example, the medical care data related to the diagnostic test can be requested by one hour. The other medical care data can be requested by one day.

The data control unit 47, upon receiving the request for the information distribution and request for the editing from the request receiving unit 46, provides the record information 16 to the page editor 48, the record information 16 being required for producing and editing the first information page 15A and for editing the second information page 15B.

The page editor 48 generates the first information page 15A according to the record information 16 provided by the data control unit 47. The page editor 48 operates as a page generator of the invention.

Figure 13:
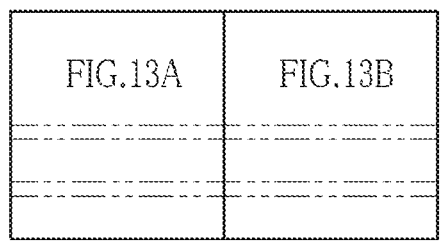

Also, the page editor 48 operates as a display processor for display processing of the first and second information pages 15A and 15B. The page editor 48 responds to the request received by the request receiving unit 46, and edits content information to be the first and second information pages 15A and 15B. Also, the page editor 48 changes a display form of normal icons 81C (normal icon windows) and small icons 82 (icon portions) of FIGS. 13, 13A and 13B according to changes in the progress of the clinical process from a professional to a patient.

The transmission controller 49 controls the information distribution of the first and second information pages 15A and 15B to the client terminal apparatus 12 by use of the communication interface 33 after generating a request for processing.

In FIG. 7, the progress information 50 is information of progress of the clinical process in association with respectively the case ID. Information items of the progress information 50 are a patient type, professional ID, symptom name, and relevant information items of the clinical process. In FIG. 7, the progress information 50 is illustrated in a condition of the doctor as a professional type, as indicated at the menu tab on the upper left corner.

Any one of the surgery-scheduled patient, out-patient and in-patient described above is recorded to an information item of the patient type. The surgery-scheduled patient is a patient of whom a request for the surgery is recorded with request data in the EMRs 24. The in-patient is a patient of whom treatment progress data in the EMRs 24 includes information of occurrence of the hospitalization but does not include information of occurrence of hospital discharge. Some of the in-patients satisfy conditions of the in-patient and the surgery-scheduled patient at the same time. For this information item of the patient type, the surgery-scheduled patient is recorded. The out-patient is a patient who is not the surgery-scheduled patient nor the in-patient. It is possible to recognize a patient type of the patient by referring to the medical care data in the EMRs 24.

A professional ID of a professional is recorded for the information item of a particular professional ID in relation to the professional in charge of medical care of the patient. The professional recorded with the particular professional ID is included in a group of professionals constituting a medical team for the patient. The particular professional ID can be recognized from the professional ID combined with the medical care data.

For the information item of the symptom name, additional data are recorded together with the symptom name such as "gastric cancer", including a date of recording the symptom name, such as 01/23, and the professional ID of the doctor having recorded the symptom name, such as D001. The symptom name and the professional ID are specifically obtained from the patient visit data (consultation data) in the EMRs 24.

The information items of the clinical process are information items of scheduling of hospitalization, diagnostic test (check-up), request for the anesthesia, preoperative summary, request for the surgery, patient consent to the anesthesia, and patient consent to the surgery. Information related to the clinical process is recorded to those information items. Specifically, information for the scheduling of the hospitalization includes a date and time of scheduling of the hospitalization, a scheduled period of the hospitalization, a room number, a room type and the like. For example, the date and time is "01/23 09:30". The scheduled period is "1/25-1/30". The room number is "405". The room type is "Single". Also, information for the request for the anesthesia includes a date of the request for the anesthesia, anesthesia type, professional ID of an anesthesiologist receiving the request, and the like. For example, the date is "01/23". The anesthesia type is "General" (whole body). The professional ID is "D005".

In the information items of the diagnostic tests, a date and the progress of the diagnostic tests are recorded, the date being 01/24 or the like for initially starting the diagnostic tests. Signs or symbols of the diagnostic tests are CT for the CT imaging, MR for the MRI (magnetic resonance imaging), DR for the simple X-ray imaging (digital radiography), US for the ultrasonography, ES for the endoscopy, HM for the blood test, BC for the biochemical test, EC for the electrocardiography (ECG), and EE for the electroencephalography.

Examples of statuses in the progress in the clinical process other than diagnostic tests are an "initial inactive" status, "incomplete" status and "completed" status. In the "initial inactive" status, the clinical process has not started. In the "incomplete" status, the clinical process has been started but not completed yet. In the "completed" status, the clinical process has been completed. In FIG. 7, the "initial inactive" status is set to the information item of the patient consent to the surgery for the case ID 0000003210. Thus, the "initial inactive" status is recorded to the information item in the clinical process. The "incomplete" status is set to the information items of the preoperative summary and patient consent to the anesthesia for the case ID 0000003210. Thus, reasons, date and professional ID are recorded to the information items in the clinical process. The reasons for the "incomplete" status are "Interruption due to liver metastasis" and "Waiting for signature". The date is 01/20 and the like for entry of the reasons. An example of the professional ID is D002. The "completed" status is set to the information items of the preoperative summary for the case ID 0123456789 and scheduling of hospitalization for the case ID 0000254798. Thus, no information is recorded to information items in the clinical process for the case ID 0000254798 to form a blank, because the anesthesia and the like are unnecessary.

Examples of statuses of the progress of each diagnostic test are a "non-tested" status, "unconfirmed" status and "confirmed" status. The "non-tested" status is a status before performing the diagnostic test. The "unconfirmed" status is a status producing the medical reports 26 but before confirming the medical reports 26 on a side of a professional. The "confirmed" status is a status after confirming the medical reports 26 on the side of the professional. Even in the same medical team, there occurs a difference between plural professionals for the "unconfirmed" status or "confirmed" status in the progress of the diagnostic test. Except for a diagnostic test of the "non-tested" status and a diagnostic test of the "confirmed" status in relation to all the professionals in the medical team, combined data are recorded for the diagnostic test, inclusive of professional IDs of professionals of the "unconfirmed" status and professional IDs of professionals of the "confirmed" status. See the information item of the diagnostic test of the case ID 0123456789 with data of "US: D050 Unconfirmed, D001, D005, D018 Confirmed".

The diagnostic test (check-up) is performed according to a flow in FIG. 8. At first, a request for the diagnostic test in the EMR 24 is generated by a particular doctor (patient's doctor) of each of hospital departments in a step S10. The request is transmitted to the client terminal apparatus 12 of the hospital department. A technician of the diagnostic test reviews the request at the client terminal apparatus 12 in a step S11. The technician prepares for test instruments and receives entry of a patient in an examination room to prepare for the diagnostic test in a step S12. The technician performs the diagnostic test (clinical process) according to the confirmed request in a step S13.

After the diagnostic test is performed, a result is uploaded in a step S14. Assuming that the diagnostic test is the imaging, the diagnostic image 25 as a result is uploaded to the image database 22A of the image server apparatus 22. Assuming that the diagnostic test is the sample test or physiological test, a test value as a result is uploaded to the EMR database 21A of the EMR server apparatus 21. Note that in case the diagnostic test is the imaging, message information is transmitted to a radiologist in charge of producing the medical reports 26 as soon as the result is uploaded.

The radiologist views the uploaded result of the imaging with the client terminal apparatus 12, and produces the medical report 26 according to the result in a step S15 (clinical process). The medical report 26 is uploaded to the report database 23A at the report server apparatus 23 in a step S16. Information of uploading of the medical reports 26 is transmitted to the particular doctor having requested the imaging in relation to the medical reports 26.

The doctor views the medical reports 26 at the client terminal apparatus 12 after being uploaded, and checks the content of the medical reports 26 in a step S17. The doctor performs diagnosis and plans content of treatment by observation of the medical reports 26. This is one of the purposes of the diagnostic tests.

The "non-tested" status is a status in a period after the step S10 or the generation of the request until the step S11 or reception of the request. The "unconfirmed" status is a status in a period after the step S16 or uploading of the medical report until the step S17 or confirmation of the medical report. The "confirmed" status is a status in a period after the step S17 or confirmation of the medical report. Note that a period after the step S11 or reception of the request until the step S16 or uploading of the medical report is a period in the course of performing the diagnostic test. Therefore, a current status in the progress of the diagnostic test is changeable incessantly. Similarly, a current status in the progress of a clinical process other than the diagnostic test is changeable incessantly.

In FIG. 9, the data address information 51 (data file) is information of addresses of storing medical care data by the case IDs. The data address information 51 has data components for the medical reports 26 and the diagnostic images 25. Other examples of data components in the data address information 51 include data components for other medical care data, such as diagnostic test data of results of the sample test and physiological test, and measurement data of a vital sign. Information of a path is recorded with each one of the data components to express the addresses of storing the medical care data, such as I:¥0123456789¥DR¥20140808¥DR001.

Figure 10:
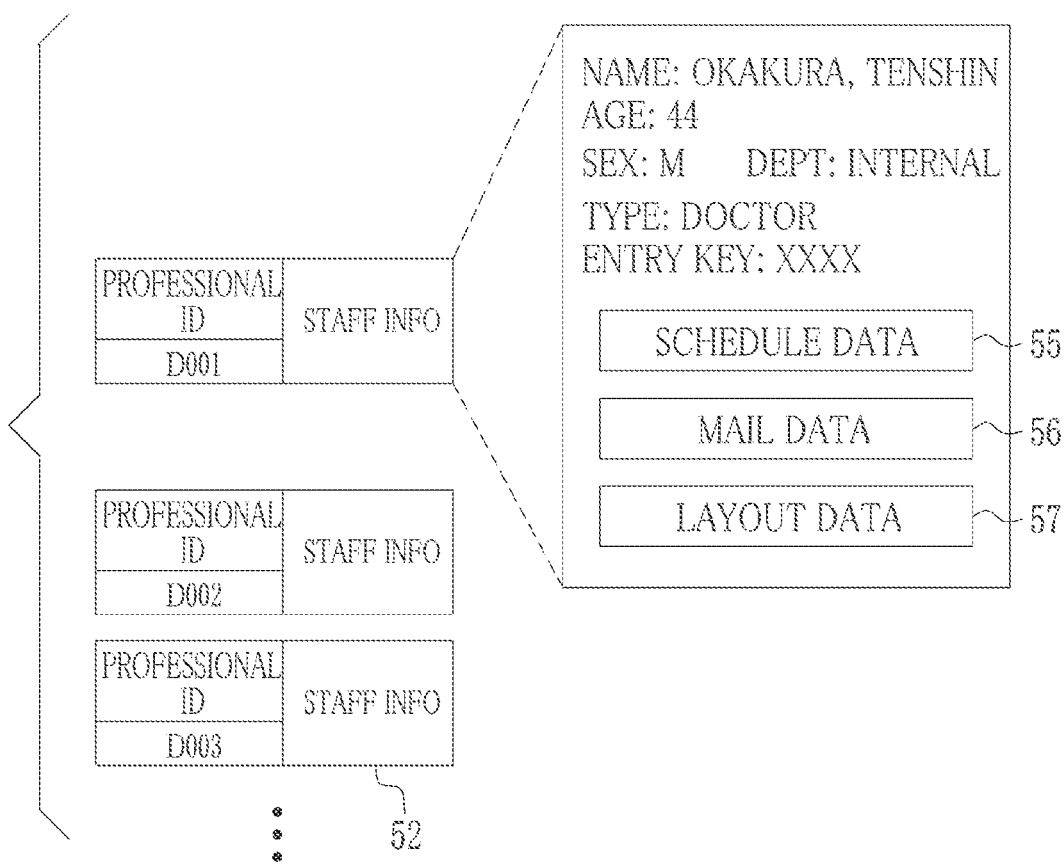
FIG. 10 is a data chart illustrating a structure for storing staff information.

In FIG. 10, the staff information 52 is managed by the unit of a professional in association with the professional ID. Datasets in the staff information 52 include a name, age, sex, hospital department, professional type, authorization key of the professional, examples of the professional type being a doctor, technician, nurse, dietician and the like. Also, other datasets in the staff information 52 (data file) include schedule data 55, mail data 56 and layout data 57, as content data related to the first and second information pages 15A and 15B.

Professional events in the schedule of a professional are recorded as the schedule data 55 in association with dates and time, such as medical care for an out-patient, hospital care for an in-patient, attendance at an academic conference, lecture in a college, vacation and the like. Various electronic mails are recorded as the mail data 56, including mails transmitted to professionals, and mails received from the professionals. Information of layout of the first and second information pages 15A and 15B customized by a professional (staff member) is recorded as the layout data 57.

Figure 11A:
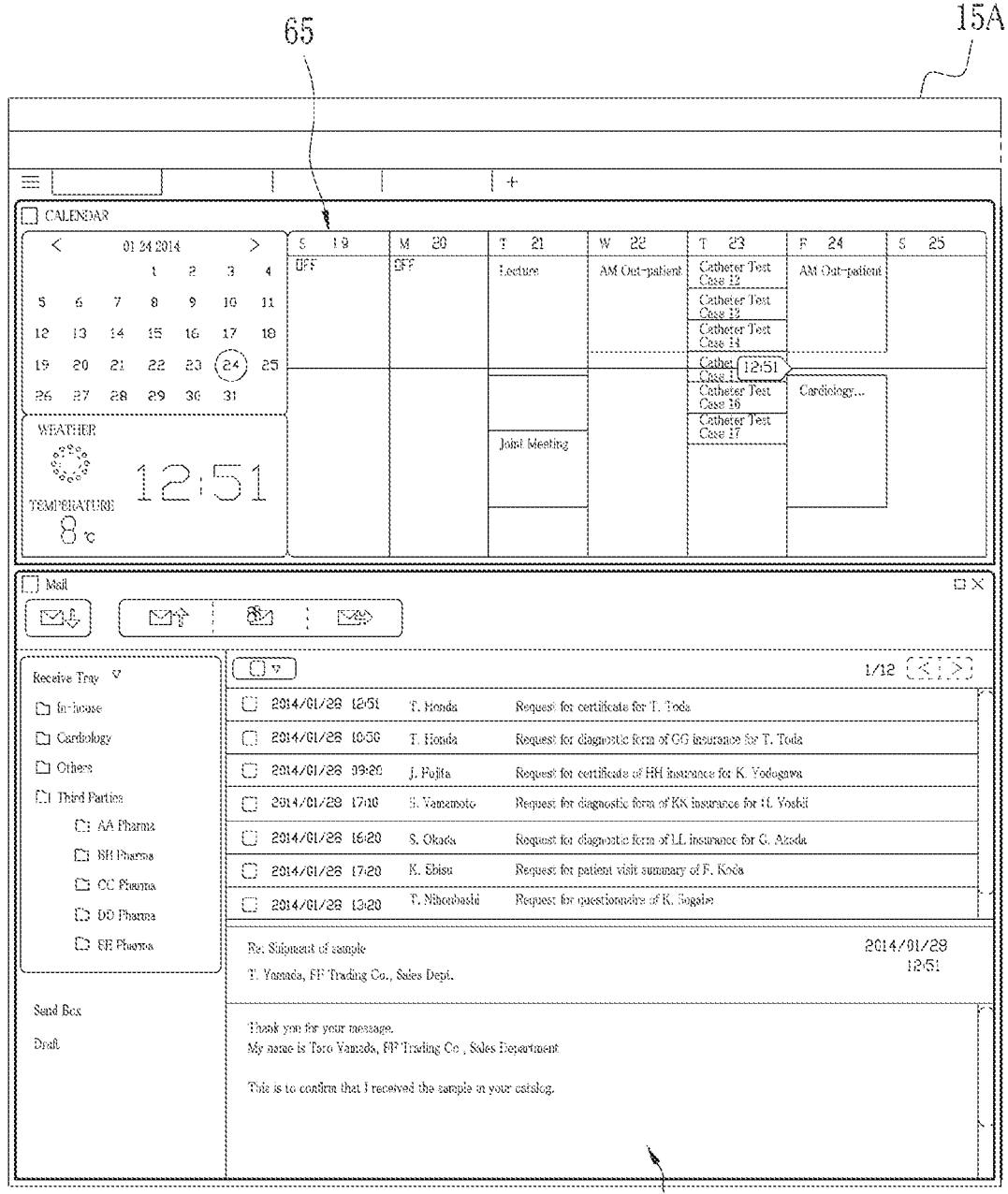

In FIGS. 11 and 11A, the first information page 15A has a schedule area 65 on an upper side, a mail area 66 on a lower side, and a patient list area 67 on a right side.

The schedule area 65 is produced by a gadget for schedule management. In the schedule area 65, the gadget for schedule management performs display processing of calendar, current time, local weather of a site of the hospital facility, temperature of the atmosphere and the like. The gadget for schedule management performs display processing of a schedule of one week of a professional of whom a professional ID is input with the login page.

The gadget for schedule management receives an input of writing a schedule by use of the schedule area 65. The request generator 42 generates a request for editing inclusive of the written schedule with the schedule area 65. The data control unit 47 writes the schedule to an area of the schedule data 55 as data included in the request, and updates the schedule data 55.

The mail area 66 is produced by a gadget for mail management. According to the mail data 56, the gadget for mail management performs display processing of a list of electronic mails to the professional of whom the professional ID has been input with the login page, texts of the mails, and the like, to the mail area 66.

The gadget for mail management receives various input actions by use of the mail area 66, such as checking reception of a new mail, response to the received mail, and drafting a new mail to be transmitted. The request generator 42 generates a request for editing inclusive of the input actions from the mail area 66. The data control unit 47 writes the data of the input actions in the request to an area of the mail data 56, and updates the mail data 56.

The gadgets for the schedule management and mail management are components included in the viewer application 40. The schedule displayed in the schedule area 65 and the mails displayed in the mail area 66 are changed over according to the professional ID input from the login page. Note that a display location, area and content of the display areas 65-67 can be changed and customized by user input of professionals. For example, only the mail area 66 is displayed on a left side by turning off the schedule area 65. Also, the schedule area 65 can be disposed at a lower left corner, and the mail area 66 can be disposed at an upper left corner. Those data of layout are recorded as the layout data 57 by the data control unit 47.

A patient list 71 or work list is displayed in the patient list area 67. The patient list 71 is information of progress of plural clinical processes for each one of the patients in relation to medical care of a professional of a professional ID input in the login page to his or her patients. It is possible to display a full screen view of each of the patient list area 67, the schedule area 65 and the mail area 66 in the entirety of the first information page 15A.

Note that various letters and numbers are actually displayed in the patient list area 67 in a right half of FIG. 11. However, the letters and numbers are substantially the same as those displayed in the patient list area 67 in FIGS. 26A and 26B.

The patient list 71 is created by the page editor 48 for each one of the professionals. To be precise, in case the professional ID input from the login page is D001, then the data control unit 47 selectively reads out the progress information 50 recorded in the information items of the professional ID D001 (the progress information 50 of the case ID 0123456789 for the patient of FIG. 7), and transfers the progress information 50 to the page editor 48. The page editor 48 produces the patient list 71 for the progress of the clinical process to the patient in association with the professional of the professional ID D001 in compliance with the progress information 50. The patient in the patient list 71 is each one of the patients to whom one of the professionals is assigned.

Figure 12:
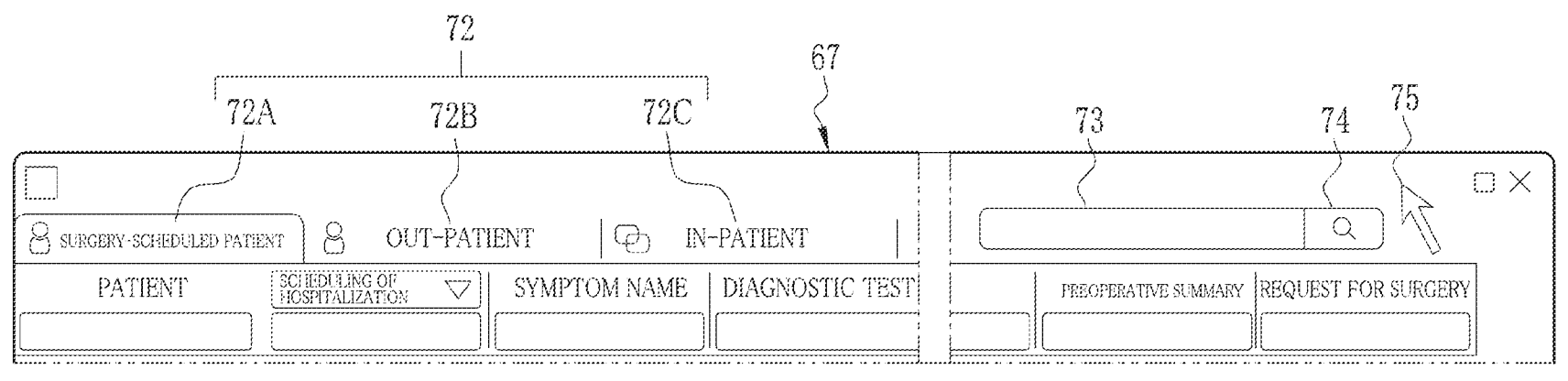

In FIG. 12, an upper portion of the patient list area 67 includes menu tabs 72, a search box 73 and a search button 74. The menu tabs 72 are used for changing over the patient type. The search box 73 is used for inputting a symptom name of the patient in relation to the patient type. The menu tabs 72 include a surgery tab 72A, an out-patient tab 72B and an in-patient tab 72C. The surgery tab 72A is one for a surgery-scheduled patient. The menu tabs 72, the search box 73 and the search button 74 are for the purpose of refining the selection of the indicated patients in the patient list 71 in relation to the patient type.

A desired one of the menu tabs 72A-72C is selected by use of the cursor 75. Otherwise, a certain symptom name is input to the search box 73 and the search button 74 is pressed by use of the cursor 75. Then a request for editing is generated by the request generator 42. Among plural datasets of the progress information 50 read out according to the request for the information distribution, the data control unit 47 transfers the progress information 50 to the page editor 48 with record of the patient type designated by the request for editing. The page editor 48 edits the patient list 71 in a form of fine selection of the patients according to the patient type on the basis of the progress information 50 transferred by the data control unit 47.

Figure 13A:
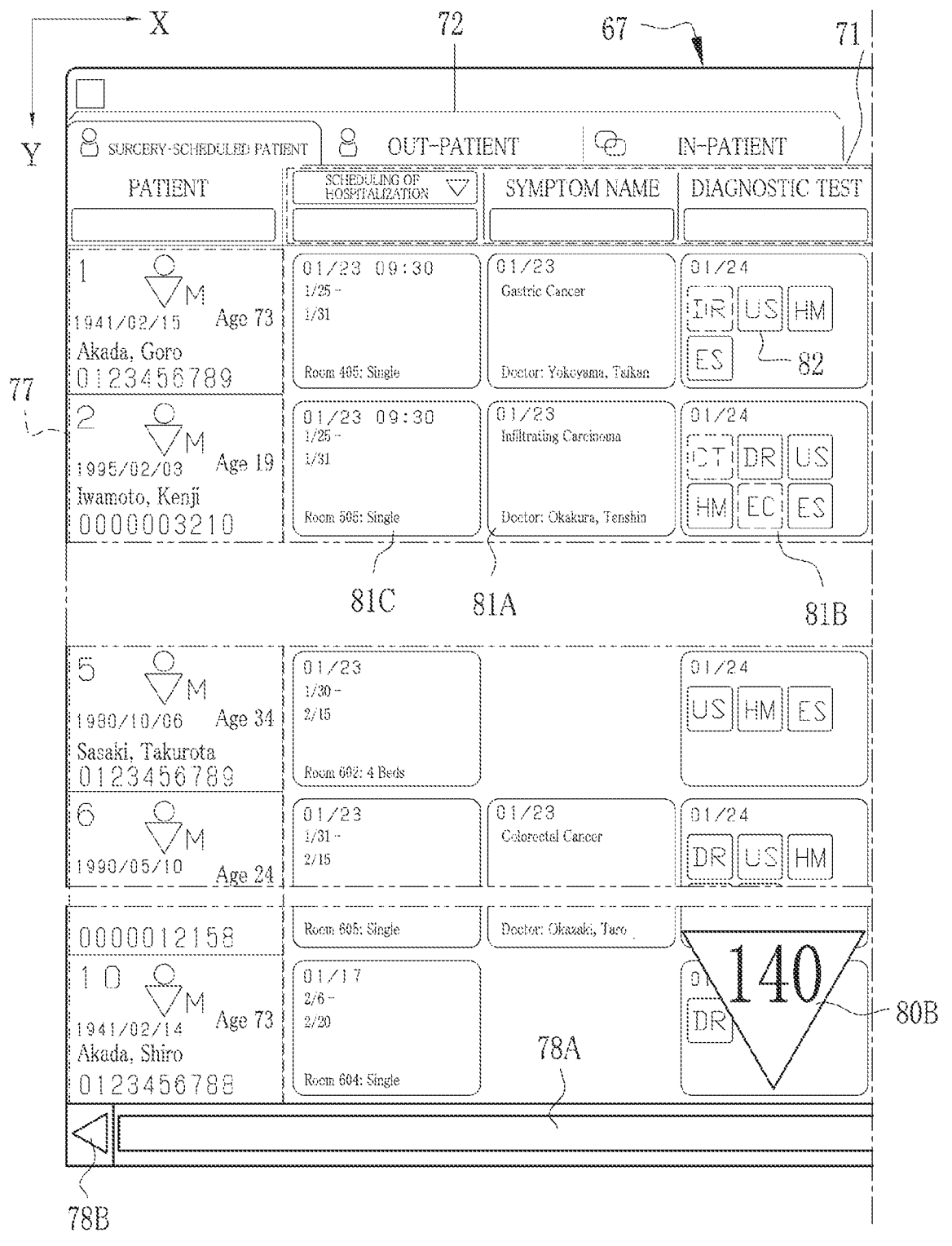
Figure 13B:
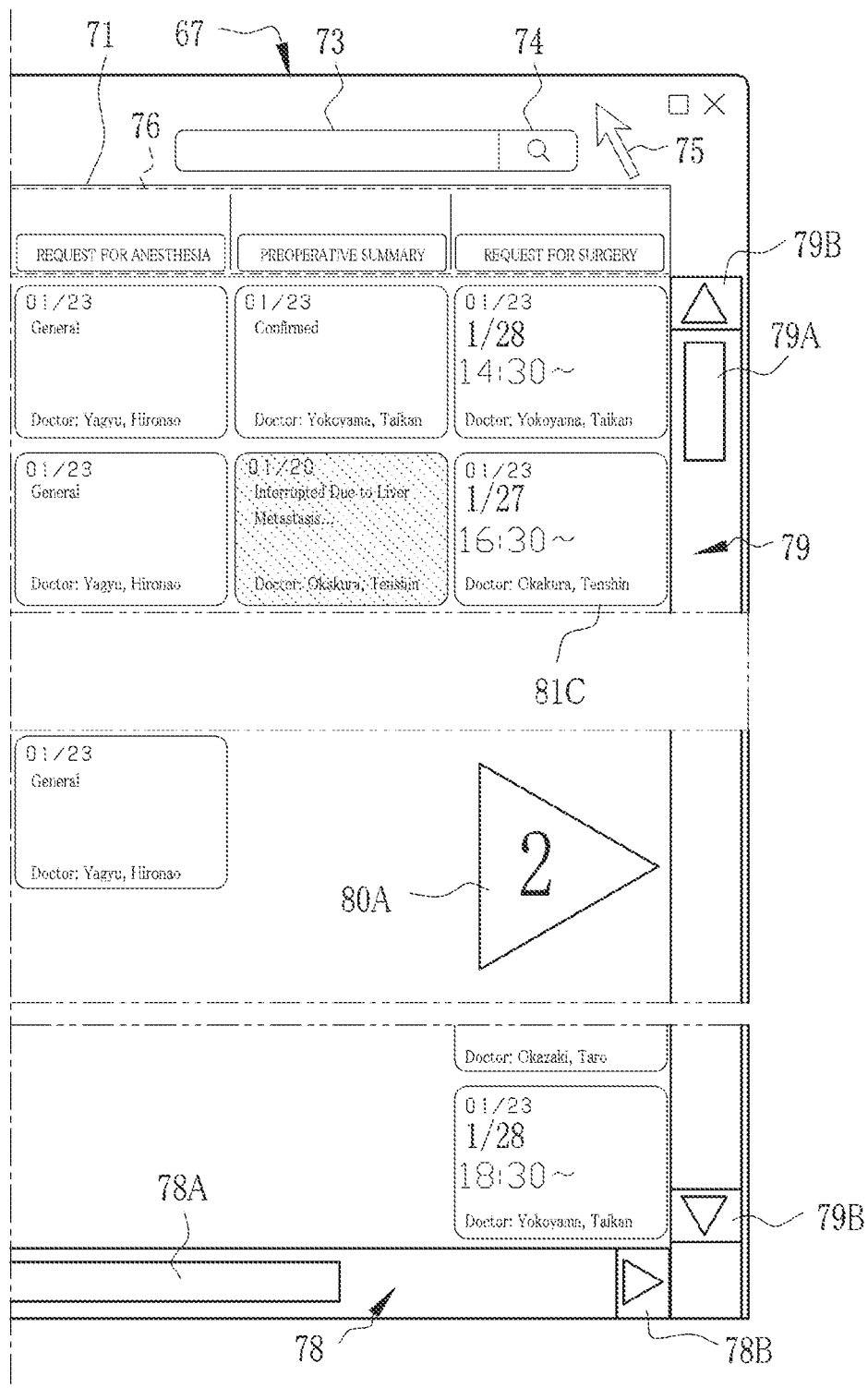

In FIGS. 13A and 13B, the patient list 71 is illustrated, in which the professional of the professional ID input from the login page is the doctor (professional type), and the surgery tab 72A for the "surgery-scheduled patient" in the menu tabs 72 is selected.

Figure 15:
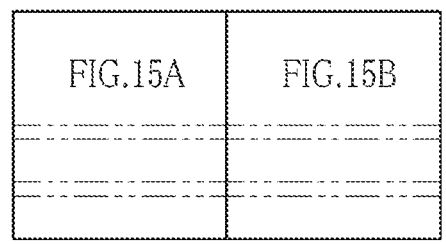

In FIGS. 13A and 13B, the patient list 71 includes an information item field 76 (row area) and a patient field 77 (columnar area). The information item field 76 extends along a horizontal axis X (corresponding to a first axis) and is disposed on an upper side. The patient field 77 extends along a vertical axis Y (corresponding to a second axis) being perpendicular to the horizontal axis X, and is disposed on a left side. The information item field 76 has an information item of a symptom name and information items of clinical processes of FIG. 7, the information items including the scheduling of the hospitalization, diagnostic test, request for anesthesia, preoperative summary, request for the surgery, patient consent to the anesthesia, patient consent to the surgery, and the like. (For the patient consent to the anesthesia and patient consent to the surgery, see FIGS. 15, 15A and 15B.) Those information items are arranged from the left to the right by following a general sequence of medical care. In the first information page 15A, there is a sorting function in the information item field 76 for sorting the display sequence of the patients in the patient list 71. The display sequence can be changed in a sequence of early dates of entering the scheduling of the hospitalization, or in a sequence of early scheduled dates of the surgery. Furthermore, it is possible in a display sequence to sort the patients in a sequence of the "initial inactive" status, "incomplete" status and "completed" status for the progress of the clinical process, or in a sequence of the greater number of diagnostic tests of the "non-tested" status for the progress of the clinical process among the various patients.

The patient field 77 indicates the personal information of each patient in combination with the serial number of the indication. The personal information includes the name, case ID, sex, birthday and age of the patient registered in the EMRs 24. Among those, the name and case ID correspond to identification data of the invention. Information of the sex is indicated by a symbol and one of the letters M and F. The patient field 77 can display personal information of 10 patients at one time as illustrated in FIG. 11.

Icons 81 (icon windows) are arranged regularly in plural arrays two-dimensionally, namely, at intersection points defined by a series of the information items of the information item field 76 and a series of datasets of personal information of the patient field 77. The icons 81 include three types, namely, a symptom icon 81A, a special icon 81B and the normal icons 81C. The icons 81A-81C have an equal size.

The symptom icon 81A (icon window) is disposed at an intersection point between an information item of the symptom name in the information item field 76 and the personal information in the patient field 77. In the symptom icon 81A, there are indicated the symptom name, date of recording the symptom name, and a particular doctor (patient's doctor) having recorded the symptom name. The symptom name and the date are recorded in the information item of the symptom name in the progress information 50. A name of the doctor can be acquired from the staff information 52 of the professional ID recorded in the information item of the symptom name in the progress information 50. Also, the symptom icon 81A can indicate a hospital department, such as a brain surgery and neurosurgery department, and cardiology department.

The special icon 81B (icon window) is disposed at an intersection point between an information item of a diagnostic test in the information item field 76 and the personal information in the patient field 77. A date of initially starting the diagnostic test is indicated in the special icon 81B, such as 01/24. A plurality of the small icons 82 are disposed in the special icon 81B. At most six small icons 82 are displayable in the special icon 81B.

The small icons 82 indicate progress of various diagnostic tests, including medical imaging such as CT (computed tomography), MRI, X-ray imaging, ultrasonic imaging, endoscopy and other medical imaging, blood test, biochemical test and other sample tests, and electrocardiography (ECG), electroencephalography (EEG) and other physiological tests. The small icons 82 are displayed only for a diagnostic test of which a request is issued by a doctor of a relevant hospital department and of which a schedule is registered. There is no indicated icon for an unnecessary diagnostic test without a registered schedule.

Alphabet letter codes are indicated in each of the small icons 82 for expressing diagnostic tests. The letter codes in the small icons 82 are the same as those of the diagnostic tests abbreviated at the information items of the diagnostic tests of the progress information 50. To be precise, the letter codes include CT for the CT imaging, MR for the MRI, DR for the simple X-ray imaging, US for the ultrasonography, ES for the endoscopy, HM for the blood test, BC for the biochemical test, EC for the electrocardiography (ECG), and EE for the electroencephalography. The small icons 82 have a size smaller than the icons 81. Each of the letter codes of the small icons 82 have only one or two letters of initials for distinction of the diagnostic tests described above.

The normal icons 81C (icon windows) are disposed at intersection points of the personal information in the patient field 77 and information items of the clinical process in the information item field 76 except for diagnostic tests. Alphanumeric information is displayed in the normal icons 81C in relation to the clinical process. The alphanumeric information is an expression of words or values for content information of the clinical process. For example, information displayed in the normal icons 81C at an information item of scheduling of hospitalization includes a date of entry of the scheduling, scheduled period, and number and type of a hospital room. Information displayed in the normal icons 81C at an information item of a request for anesthesia includes a date of the request, type of the anesthesia, and name of an anesthesiologist. Information displayed in the normal icons 81C at an information item of a request for the surgery includes a date of the request, surgery date, and name of a surgeon. Content information of the alphanumeric information is recorded in information items of the clinical processes of the progress information 50. Furthermore, it is possible additionally to display alphanumeric information of a surgical procedure in the normal icons 81C disposed in an information item of a request for the surgery.

In the same manner as the small icons 82, the normal icons 81C are displayed only in relation to the clinical process of surgery and the like of which a request is recorded in request data in the EMRs 24 by a doctor of a hospital department for a registered schedule of the surgery. The normal icons 81C for a clinical process without necessity are not displayed, such as a clinical process of patient consent to the anesthesia of the case ID of 0000254798. There occurs a blank 83 in the patient list 71 for this location as illustrated in FIG. 19.

Display colors in a normal state are allocated to the icons 81A-81C for each of the information items. A color of the normal icons 81C at the information item of the scheduling of the hospitalization is russet brown. A color of the special icon 81B and the small icons 82 at the information item of the diagnostic test is yellow ocher. A color of the normal icons 81C at the information item of the request for the anesthesia is greenish brown. A color of the normal icons 81C at the information item of the request for the surgery is dark green. A color of the normal icons 81C at the information item of the patient consent to the surgery is indigo blue. A display form of the icons 81A-81C is full-color with chromaticity. Also, alphanumeric information in the icons 81A-81C and the small icons 82, and peripheral lines of the small icons 82 are expressed in white color as blank portions.

A horizontal scroll bar 78 and a vertical scroll bar 79 are disposed in the patient list 71. See FIGS. 11 and 11A. The horizontal scroll bar 78 extends along the horizontal axis X on a lower side of the patient list 71 and opposite to the information item field 76. The vertical scroll bar 79 extends along the vertical axis Y on a right side of the patient list 71 and opposite to the patient field 77. The horizontal scroll bar 78 has a slider 78A and a pair of arrow buttons 78B. The slider 78A is movable in the horizontal scroll bar 78. The arrow buttons 78B are disposed at ends of the horizontal scroll bar 78. Similarly, the vertical scroll bar 79 has a slider 79A and a pair of arrow buttons 79B.

The page editor 48 additionally forms the horizontal scroll bar 78 in the patient list 71 assuming that partial information items among all the information items are displayed in the first information page 15A but remaining information items are undisplayed in the first information page 15A according to layout of the first information page 15A based on the layout data 57. The page editor 48 additionally forms the vertical scroll bar 79 in the patient list 71 assuming that partial datasets of personal information in all the personal information are displayed in the first information page 15A but remaining datasets of the personal information are undisplayed in the first information page 15A.

In FIGS. 13A and 13B, information items of the patient consent to the anesthesia and patient consent to the surgery are undisplayed among the information items of the scheduling of hospitalization, symptom name, diagnostic test, request for anesthesia, preoperative summary, request for surgery, patient consent to the anesthesia, patient consent to the surgery, and the like. Personal information of ten patients of serial numbers 1-10 is displayed. Personal information of the remaining patients is undisplayed.

The page editor 48 performs display processing of an information item number window area 80A and a patient number window area 80B in the patient list 71 while the horizontal and vertical scroll bars 78 and 79 are displayed. See FIG. 11. The information item number window area 80A (mark) indicates a number of the information items in an undisplayed portion, and is disposed on the right side at the center in the patient list 71. The patient number window area 80B (mark) indicates a number of the datasets of the personal information (namely, number of patients) in the undisplayed portion, and is disposed on the lower side at the center in the patient list 71.

Figure 14:
FIG. 14 is an explanatory view illustrating a number window area for patient bodies.

The number window areas 80A and 80B are displayed with the icons 81 in an overlapped manner. A display form of the number window areas 80A and 80B is translucent and in achromatic gray. It is possible to observe indicated information in the icons 81 even in presence of the number window areas 80A and 80B as depicted by the dotted line in the patient number window area 80B in FIG. 14.

Numbers are indicated in the number window areas 80A and 80B for totals of cases. In FIGS. 13A and 13B, a number of 2 is indicated in the information item number window area 80A to inform that two information items of the patient consent to the anesthesia and patient consent to the surgery are undisplayed. A number of 140 is indicated in the patient number window area 80B. Those indications inform that personal information of 140 patients is undisplayed currently, and the two information items are undisplayed.

The number window areas 80A and 80B are in tapered shapes (or projecting shapes) of triangles to point directions of a hidden location of the undisplayed portion. In FIGS. 13A and 13B, the undisplayed portion of the information items of the patient consent to the anesthesia and patient consent to the surgery is hidden on the right side from the patient list 71. Thus, the information item number window area 80A is the tapered shape to point the right side. Also, the undisplayed portion of the personal information of the remaining patients different from the ten patients of serial numbers 1-10 is hidden on the lower side from the patient list 71. Thus, the patient number window area 80B is the tapered shape to point the lower side.

Figure 15A:
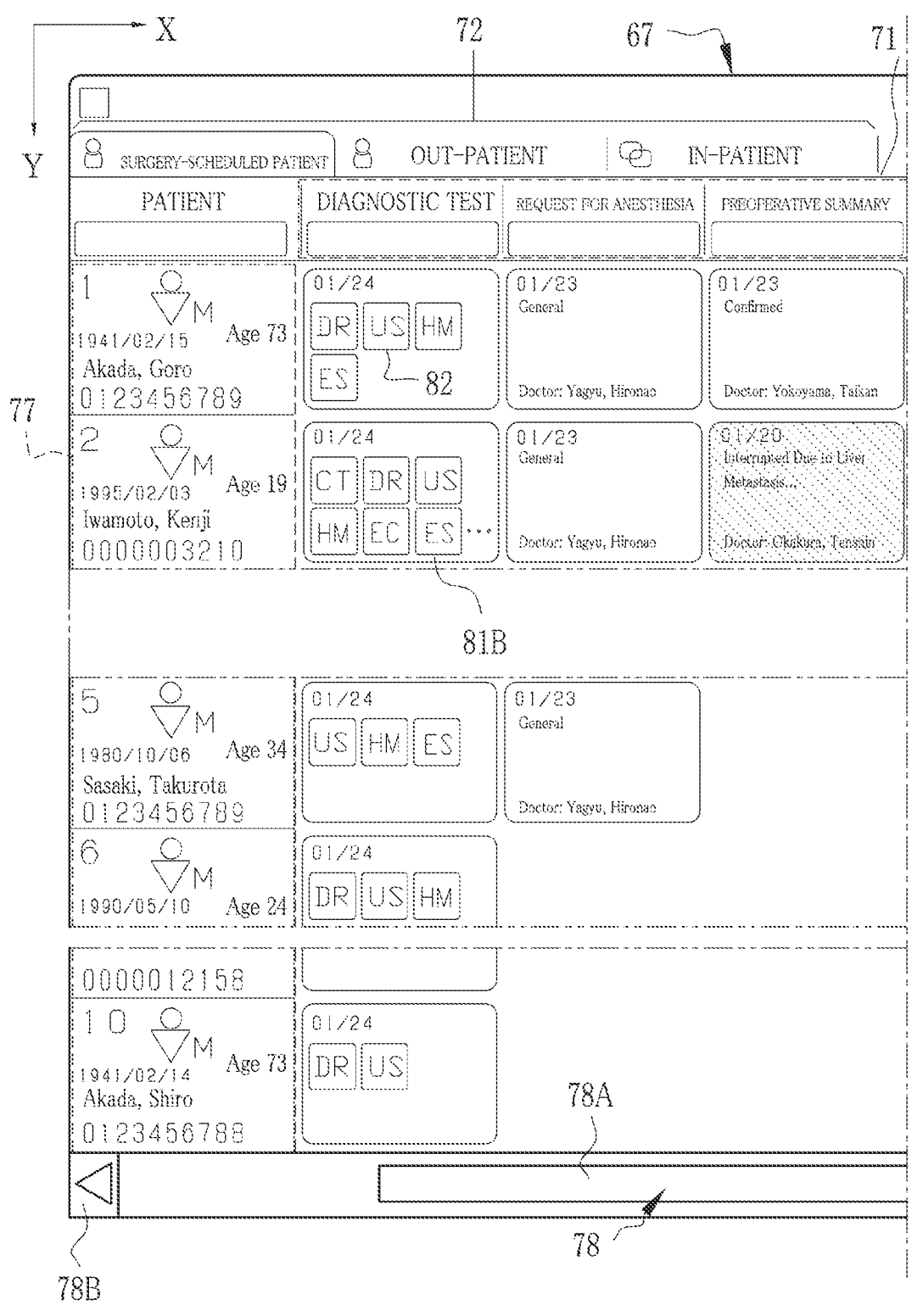

The undisplayed portion becomes displayed by an input action for scroll, such as press of the sliders 78A and 79A or the arrow buttons 78B and 79B with the cursor 75, or rotation of a wheel button of a mouse. In FIGS. 15A and 15B, an example of an input action for scroll to the right is illustrated. The first information page 15A comes to display the patient consent to the anesthesia, patient consent to the surgery and the icons 81 associated with those, unlike the undisplayed portion in FIGS. 13A and 13B. At the same time, the scheduling of the hospitalization, symptom name, and the icons 81 associated with those are made undisplayed in the first information page 15A. The number window areas 80A and 80B become deleted by this scroll. Note that positions of the information item field 76 and the patient field 77 are unchanged even upon occurrence of the scroll.

A clinical process of a professional to a patient is different between the patient types and between professional types. Assuming that the patient type is an out-patient, no clinical process related to hospitalization or surgery is required, such as scheduling of the hospitalization or request for the surgery described with FIGS. 13A and 13B. Assuming that the professional type is a dietician, clinical processes not depicted in FIGS. 13A and 13B are required, such as creation of menus of meals for the in-patient, guide for nutrition for the in-patient, and the like. Consequently, information items in the information item field 76 in the patient list 71 are different between the patient types and the professional types, as illustrated in a type mapping table 84 of FIG. 16.

In FIG. 16, let a patient type be a surgery-scheduled patient. Let a professional type be a doctor. Information items in the information item field 76 are a symptom name, scheduling of hospitalization, diagnostic test, request for anesthesia, preoperative summary, request for surgery, patient consent to the anesthesia, patient consent to the surgery, and the like depicted in FIGS. 13A and 13B. Let a patient type be an out-patient. Information items of a symptom name, diagnostic test and patient referral are prepared irrespective of the professional type. The patient referral is a document of description of medical information of a patient issued by a previous doctor assuming that the out-patient has a history of past medical care of the previous doctor at a clinic or different hospital.

Assuming that the patient type is an in-patient and the professional type is a doctor, then the information items indicated in the information item field 76 include a symptom name, meal, scheduling of the hospitalization, diagnostic test, request for the surgery, patient care plan, anti-bedsore plan, nutrition plan, follow-up plan, and post-discharge summary.

The patient care plan is a document created by the doctor, and includes information of a symptom name (disease, disorder or injury), progress, plan for treatment, diagnostic tests, surgery, date of the surgery, estimated period of hospitalization, and the like. The anti-bedsore plan is a document created by a nurse, and includes information of bedsore of a patient hospitalized in a long term, prevention and treatment of the bedsore, and the like. The nutrition plan is a document created by a dietician, and includes information of menus of meals for the patient in the hospital, guide information for nutrition to the patient, and the like. The follow-up plan is a document created by the doctor, and includes information of an estimated date of hospital discharge, symptom at the time of the hospital discharge, plan of treatment after the hospital discharge, medical advice related to a bed rest level, meals, medication and bathing, guide information for healthcare services and welfare services, and the like. The post-discharge summary is a document of a summarized result of diagnostic tests performed during the hospitalization.

Figure 17:
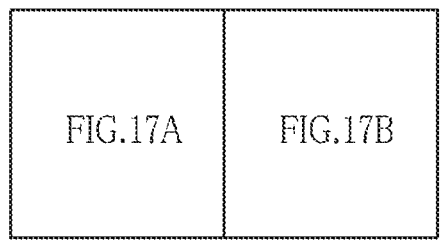

The information items in the information item field 76 are different between the professional types, so that other sets of the progress information 50 for nurses, dieticians and the like are recorded in addition to the progress information 50 for the doctor in FIG. 7. Assuming that the type of the professional of whom the professional ID is input from the login page is the dietician, and assuming that the in-patient tab 72C in the menu tabs 72 is selected, then the patient list 71 according to the patient type and professional type is created and edited by the page editor 48 in the manner of the patient list 71 in FIGS. 17, 17A and 17B.

In the information item field 76 in the patient list 71 of FIGS. 17A and 17B, various information items are indicated according to information items in the dietician for the "in-patient" as patient type in the type mapping table 84 of FIG. 16, the information items including a symptom name, scheduling of hospitalization, diagnostic test, request for the surgery, patient care plan, nutrition plan and follow-up plan (planning document). The icons 81 are disposed in plural arrays at intersection points of the information items and the personal information in the same manner as FIGS. 13A and 13B. The normal icons 81C at the information item of the meal indicate data inclusive of dates before and after the surgery, meal types, and name of the dietician, the meal types including liquid food, fasting, normal food, parenteral nutrition, and the like. The normal icons 81C at the information items of the patient care plan, nutrition plan and follow-up plan indicate a date of submitting the plans, and name of a professional having drafted the plans.

Assuming that the patient type is an out-patient, the normal icons 81C at the information item of the patient referral (not shown) indicate alphanumeric information such as a name of a previous hospital facility (primary care), and a name of a previous doctor. Also, other information items can be added, such as a request for blood transfusion and patient consent to the blood transfusion for the purpose of the surgery requiring the blood transfusion, and a request for the use of ICU (Intensive Care Unit). For example, information items of daily clinical processes can be added in relation to the nurse, including measurement of body temperature, measurement of a heart rate, measurement of a blood pressure, drawing of blood, and the like for an in-patient. Also, it is possible to change information items of diagnostic tests according to the professional type, for example, all of the diagnostic tests including imaging, sample test and physiological test for the doctor, nurse and technician of the test, and only the sample test for the dietician.

In FIG. 18, the page editor 48 changes the display form of the small icons 82 according to changes in the progress in the diagnostic tests. At the time of the "non-tested" status for the progress, a small icon 82A is displayed with achromatic gray color for alphanumeric information and frame lines of "CT" and "EC" indicated in the phantom line. At the time of the "unconfirmed" status for the progress, a small icon 82B is displayed with white color for alphanumeric information and frame lines of "US". A dot or unread flag 85 is indicated in the small icon 82B. At the time of the "confirmed" status for the progress, a small icon 82C is displayed with white color for alphanumeric information and frame lines of "DR", "HM" and "ES".

As has been described heretofore with FIG. 7, the "unconfirmed" or "confirmed" status in the progress of the diagnostic test is different between professionals. For example, let a professional ID of D007 be input by use of the login page. Data of "US: D007 Unconfirmed" is recorded at the information item of the diagnostic test of the patient with the case ID of 0000003210 in the progress information 50. Thus, the unread flag 85 is displayed in the small icon 82 of US in the manner of the small icon 82B in FIG. 18. Also, let a professional ID of D002 be input by use of the login page. Data of "US: D002 Confirmed" is recorded at the information item of the diagnostic test of the patient with the case ID of 0000003210 in the progress information 50. Thus, the unread flag 85 does not appear in the small icon 82 of US. The small icon 82 of US is indicated in the same manner as the small icons 82C of DR, HM and ES. In short, the progress indicated in the patient list 71 is different between the professionals.

Ellipsis dots 86 (AND MORE) are indicated assuming that the types of the diagnostic tests are more than six and assuming that the number of the small icons 82 is more than six that is the maximum displayable within the special icon 81B. In case the ellipsis dots 86 are designated (clicked) by use of the cursor 75, hidden small icons 82 become displayed in a pop-up manner on the special icon 81B though the number of the diagnostic tests in relation to the special icon 81B is more than six.

In FIG. 19, the page editor 48 changes a display form of the normal icons 81C with changes in the progress of the clinical process other than diagnostic tests. Let the progress be in the "initial inactive" status. A normal icon 81CA indicated by the dotted line for the information item of the patient consent to the surgery for the case ID of 0123456789 is displayed achromatically with white color, without preset colors of chromaticity. A frame line of the normal icon 81CA is displayed with the dotted line. Let the progress be in the "incomplete" status. A normal icon 81CB indicated by a hatched portion for the information items of the preoperative summary and patient consent to the anesthesia of the case ID 0123456789 is displayed achromatically with gray color and white letters, without preset colors of chromaticity. Let the progress be in the "completed" status. A normal icon 81CC of the case ID 0123456789 and the information item of the request for the surgery of the case ID 0123456789 are displayed in a colored form with a predetermined color and white letters. Note that FIG. 19 illustrates partial components in the same page as FIGS. 15A and 15B, in which information items of the patient consent to the anesthesia and the patient consent to the surgery and the icons 81 for the information items are displayed after scroll to the right from the state of FIGS. 13A and 13B.

In case the patients are finely selected, personal information of the selected patients of the particular patient types is displayed in the patient field 77 of the patient list 71. The icons 81 and the small icons 82 indicate the progress of the clinical process for the selected patients of the particular patient types. The patients and the progress displayed in the patient list 71 are different according to the types of the patients. In a case before the fine selection of the patient types, the patient list 71 being created contains mixed information of patients of various types including the "surgery-scheduled patient", "out-patient" and "in-patient".

The personal information in the patient field 77 can be selected by use of the cursor 75. Upon the selection of the personal information with the cursor 75, the request generator 42 generates a request for editing of the second information page 15B for displaying the medical reports 26 and a result of a diagnostic test of the patient related to the selected personal information. The data control unit 47 selectively reads out addresses from the data address information 51 for the medical care data of the case ID of the patient related to the selected personal information. The data control unit 47 performs access to the addresses of the selective readout, acquires medical care data required for forming the second information page 15B, and transfers the medical care data to the page editor 48. The page editor 48 edits the second information page 15B according to the medical care data from the data control unit 47.

Figure 20:
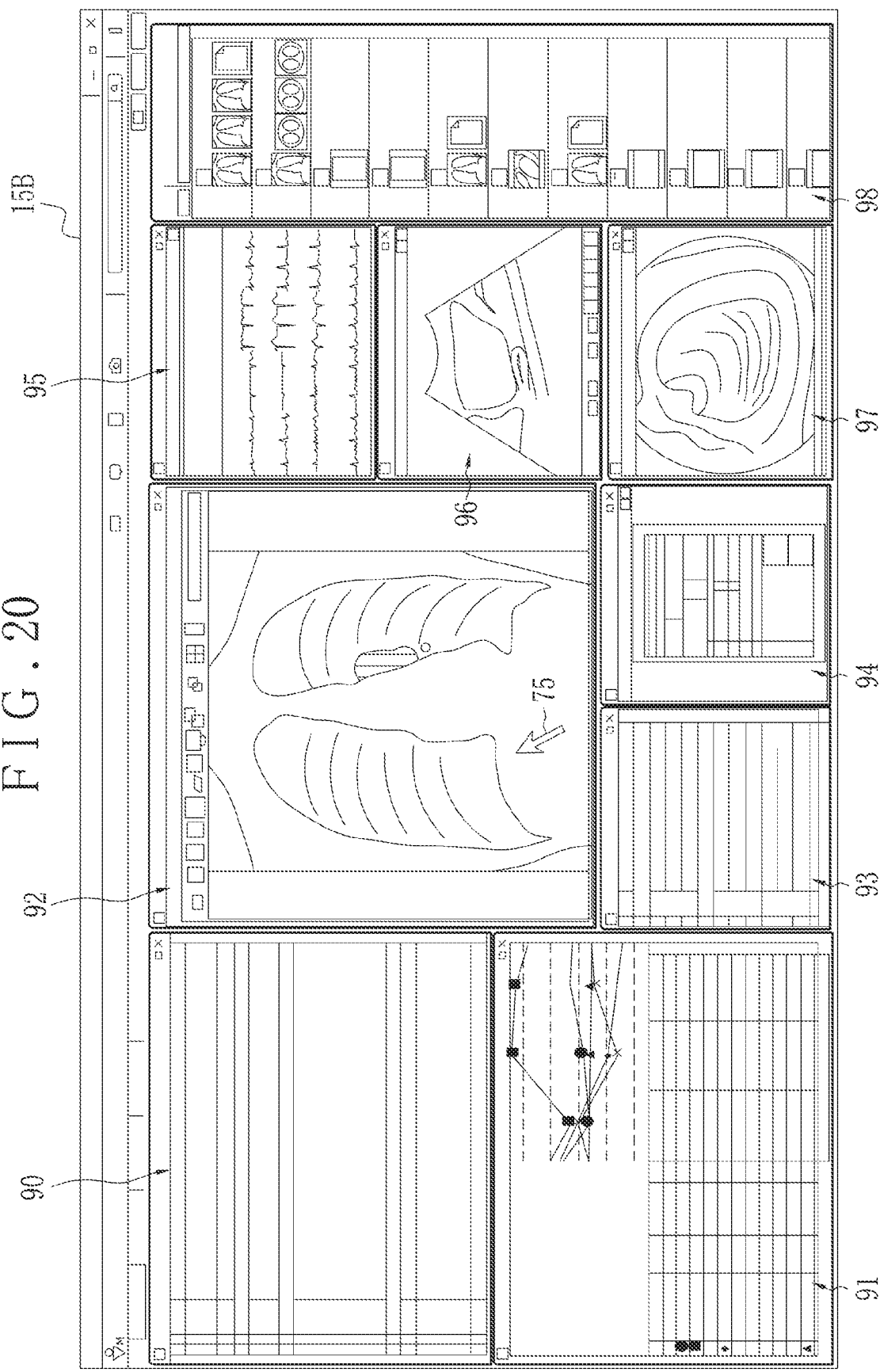
FIG. 20 is a screen view illustrating a second information page.

In FIG. 20, the second information page 15B includes nine display areas, namely a progress note area 90, a diagnostic area 91, an X-ray area 92, a medication area 93, a report area 94, an ECG area 95, an ultrasonography area 96, an endoscopy area 97 and a history area 98. The progress note area 90 and the diagnostic area 91 are disposed on a left side. The X-ray area 92, the medication area 93 and the report area 94 are disposed in the center as viewed in the longitudinal direction of the second information page 15B. The ECG area 95, the ultrasonography area 96, the endoscopy area 97 and the history area 98 are disposed on a right side. The second information page 15B is a page for displaying the medical reports 26 and results of medical diagnostic tests as detailed information of the clinical process.

The second information page 15B is displayed on the display panel 34B of the client terminal apparatus 12 in place of the first information page 15A in an exchangeable manner to the first information page 15A. Otherwise, the second information page 15B is displayed on the display panel 34B as a discrete page from the first information page 15A.

In a manner similar to the display areas 65-67 in the first information page 15A, a display position, display area and content in the second information page 15B can be customized with degree of freedom by user inputs of a professional or the like. Data of the layout is recorded as the layout data 57. For example, additional display areas can be disposed, including an area for a result of the CT imaging, an area for a result of the MRI imaging, and an area for other diagnostic tests, and an area for patient consent to the anesthesia, and an area for patient consent to the surgery.

In the progress note area 90, a gadget for displaying description operates to display description such as patient visit data in the EMRs 24 in a time sequence. In the diagnostic area 91, a gadget for displaying test results operates to display test values of sample tests such as blood test and biochemical test, and also a graph of changes of the test values with time. In the X-ray area 92, a gadget for displaying X-ray images operates to display an X-ray image formed by the X-ray imaging. In the medication area 93, a gadget for displaying medication operates to display information of drug administration in a time sequence according to the request data for the drug administration and the treatment progress data.

The medical report 26 is displayed in the report area 94 by use of a gadget for displaying the report. An electrocardiogram of electrocardiography is displayed in the ECG area 95 by use of a gadget for displaying the ECG result. An ultrasonic image of ultrasonography is displayed in the ultrasonography area 96 by use of a gadget for displaying the ultrasonography result. An endoscopic image of endoscopy is displayed in the endoscopy area 97 by use of a gadget for displaying the endoscopy result. History information of a medical history of the various diagnostic tests of the patient is displayed in the history area 98 by use of a gadget for displaying the history. Those gadgets are components included in the viewer application 40. The display areas 90-98 can be displayed in a full screen view in the second information page 15B by enlargement.

Figure 21:
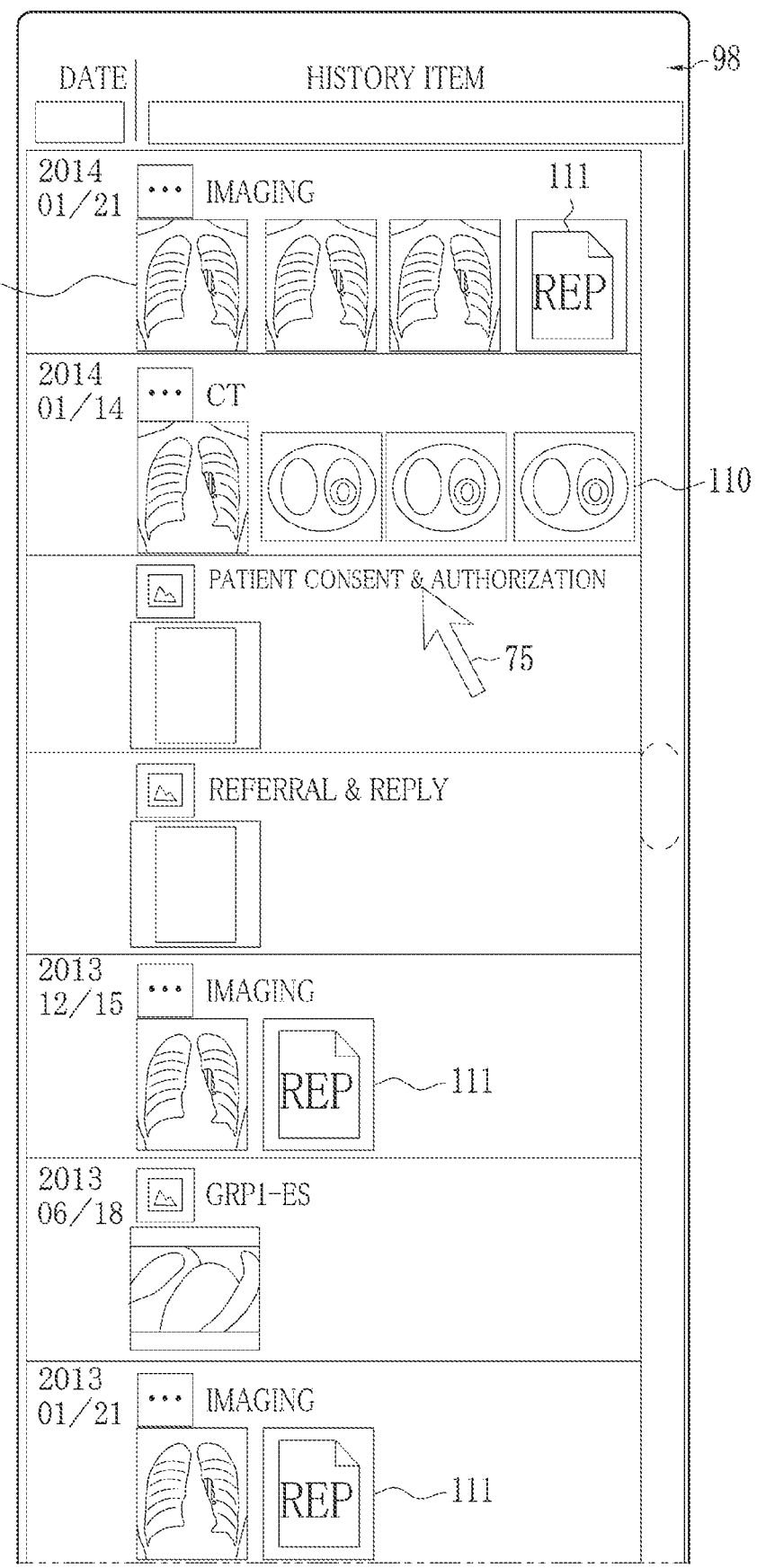
FIG. 21 is a screen view illustrating a history area.

In FIG. 21, the history area 98 contains history information of the history of diagnostic tests of newer dates in a sequence toward the lower side. In the history of the diagnostic tests, a thumbnail icon 110 for the diagnostic images 25 and a link icon 111 for the medical reports 26 are displayed with the date of the diagnostic test. The history of the diagnostic test of the "non-tested" status of the progress is not displayed, so that the thumbnail icon 110 and the link icon 111 are not displayed.

In case the thumbnail icon 110 is selected by use of the cursor 75, an image portion of the diagnostic images 25 of the thumbnail icon 110 becomes displayed in an area for the result of the diagnostic test. For example, in case the thumbnail icon 110 of X-ray imaging is selected, an image portion of the X-ray image becomes displayed in the X-ray area 92. In case the link icon 111 is selected by use of the cursor 75, a document of the medical reports 26 becomes displayed in the report area 94. To this end, requests for selecting the thumbnail icon 110 and the link icon 111 are generated by the request generator 42 as requests for editing.

The diagnostic images 25 obtained in the newest diagnostic test are indicated in the X-ray area 92, the ultrasonography area 96 and the endoscopy area 97 in the second information page 15B displayed initially by selecting the personal information with the cursor 75. Also, an ECG image obtained the most newly in the electrocardiography and the medical reports 26 are displayed in the ECG area 95 and the report area 94.

The data control unit 47, upon receiving a request from the request receiving unit 46 for editing by selecting the personal information or by selecting the link icon 111, recognizes that the medical reports 26 have finished being confirmed by a login professional. The data control unit 47 changes the "unconfirmed" status to the "confirmed" status for the progress of the professional in the information item of the diagnostic test in the progress information 50.

Figure 22:
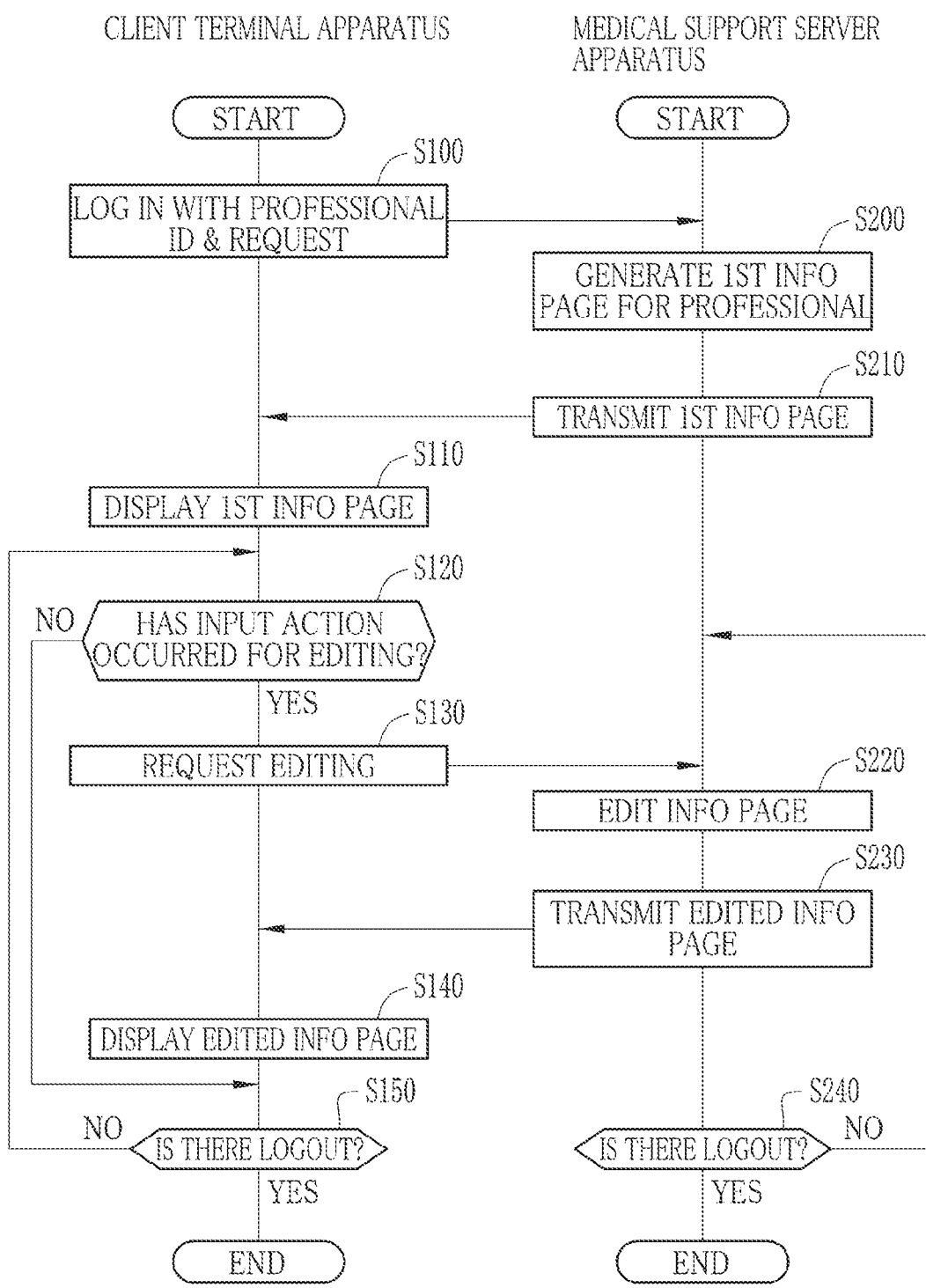
FIG. 22 is a flow chart illustrating operation of processing for the medical support.

The operation of the above construction is described now by referring to FIG. 22. At first, a medical professional (medical staff member) manually operates the client terminal apparatus 12 to start up the viewer application 40. The GUI controller 41 and the request generator 42 are established in the CPU 32B of the client terminal apparatus 12 by running the viewer application 40.

In FIG. 22, the professional inputs a professional ID by use of the login page to view the first information page 15A in a step S100. The request generator 42 generates a request for information distribution of the first information page 15A.

In the medical support server apparatus 11, the request receiving unit 46, the data control unit 47, the page editor 48 and the transmission controller 49 are established in the CPU 32A by running the control program 45. The medical support server apparatus 11 operates as a medical support apparatus.

The request for information distribution from the request generator 42 of the client terminal apparatus 12 is received by the request receiving unit 46 in the medical support server apparatus 11, and transferred to the data control unit 47. The data control unit 47 selectively reads the record information 16 from the record database 11A with necessity for generating the first information page 15A, for example, the progress information required for creating the patient list 71. The record information 16 read by the data control unit 47 is provided to the page editor 48.

The page editor 48 creates the first information page 15A according to the record information 16 from the data control unit 47 in a step S200. The page editor 48 changes a display form of the small icons 82 (icon portions) as illustrated in FIG. 18 according to a change in the progress in the diagnostic test. The page editor 48 changes a display form of the normal icons 81C as illustrated in FIG. 19 with changes in the progress in a clinical process other than the diagnostic test.

In FIGS. 13A and 13B, the horizontal or vertical scroll bar 78 or 79 becomes displayed in the patient list 71 by the page editor 48 while the undisplayed portion of the hidden form in relation to the first information page 15A is defined with a part of the plural information items (corresponding to partial information items) and/or a part of the plural datasets of the personal information (corresponding to partial identification data). Also, the number window area 80A or 80B is displayed in the patient list 71. The first information page 15A is transmitted to the client terminal apparatus 12 by the transmission controller 49 in a step S210.

In the client terminal apparatus 12, the GUI controller 41 causes the display panel 34B to display the first information page 15A in a step S110. The first information page 15A contains the patient list 71 in which the special icon 81B is displayed with a plurality of the small icons 82 for indicating the progress of various diagnostic tests.

In case an input action for scroll is performed to redisplay the undisplayed information, the number window areas 80A and 80B are deleted.

Items in the information item field 76 and patients (patient bodies) in the patient field 77 are different between professional types of the professionals and patient types of the patients. So the numbers indicated in the number window areas 80A and 80B are different between the professional types and the patient types. Thus, the professional can find the data amount related to the undisplayed portion, such as the total of the information items or personal information in the undisplayed portion, as the information item number window area 80A for the undisplayed information items or the patient number window area 80B for the undisplayed personal information is displayed in the patient list 71. The professional can view the patient list 71 without problems in the visual perceptibility and interface functionality, as user accessibility and time related to viewing the patient list 71 can be estimated apparently.

The icons 81 can be viewed through the number window areas 80A and 80B, which are translucent. The number window areas 80A and 80B are deleted upon an input action for scroll to redisplay the undisplayed portion. The icons 81 are safely visible in the absence of the number window areas 80A and 80B after reading the number of the information items included in the undisplayed portion and the number of the patients of whom the personal information is included in the undisplayed portion. There is no partial blocking of the patient list 71 for viewing.

The special icon 81B makes it possible to arrange the small icons 82 with good visual perceptibility, or compactly for expressing the progress of various diagnostic tests in a limited display area of the patient list 71 in the horizontal direction of the axis X. Thus, a size of the information item field 76 in the horizontal direction can be kept from excessive increase. It is possible to satisfy requirements of professionals for grasping the progress of a large number of clinical processes at one time without extra time or labor for manipulation.

The small icons 82 are icons for the progress of diagnostic tests in the same category of the clinical processes. A set of the small icons 82 is contained in the special icon 81B, so that it is possible to recognize the progress of the diagnostic tests as one group. The progress of the diagnostic tests can be grasped more easily than a structure in which plural icons for the progress of the plural diagnostic tests are disposed in the patient list 71 at plural locations distant from one another. A list form of displaying the progress of the plural diagnostic tests can be useful with good visual perceptibility. The number of the diagnostic tests is high because of inclusion of the imaging, sample tests and physiological tests. The progress can be viewed in comparison between the diagnostic tests even with the number of the diagnostic tests.

The normal icons 81C are also displayed in the patient list 71 in the same size as the special icon 81B for indicating the progress of the clinical process other than the diagnostic tests. Alphanumeric information is indicated in the normal icons 81C, including a date and time of a past clinical process, scheduled date and time, type, professional of the clinical process, professional of the past clinical process, reason of interrupting the clinical process, and the like. Also, alphanumeric information is indicated in the small icons 82 for indicating a type of the diagnostic test. Thus, quality in medical care of a medical team can be set high as the relevant information can be shared between professionals in relation to the clinical process.

Should only the special icon 81B be used for the icons 81, grasping the progress may be more difficult, as the content of the clinical process is not apparently clarified. However, the special icon 81B in the invention is limited to the icon for progress of the clinical process of the same category (diagnostic tests). The normal icons 81C are used for progress of other clinical processes. Thus, the patient list 71 can be set useful for totally grasping the progress.

The small icons 82 indicate the statuses of the progress, namely, the "non-tested" status, "unconfirmed" status and "confirmed" status. In the "non-tested" status, a diagnostic test has not been performed. In the "unconfirmed" status, the diagnostic test has been performed to produce the medical report 26, but the medical report 26 has not been reviewed and confirmed. In the "confirmed" status, the medical report 26 has been reviewed and confirmed. Let the professional be a technician for a diagnostic test. The progress expressed by the small icon 82 is the "non-tested" status. Then it is possible to remind the technician rapidly to perform the diagnostic test. Also, let the professional be a doctor. The progress expressed by the small icon 82 is the "unconfirmed" status. Then it is possible to remind the doctor rapidly to review and confirm the medical report 26.

The use of the normal icons 81C indicates the progress of the "initial inactive" status, "incomplete" status and "completed" status. The "initial inactive" status is a status before starting the clinical process. The "incomplete" status is a status after starting the clinical process but before completing the same. The "completed" status is a status of completion of the clinical process. Assuming that the progress expressed by the normal icons 81C is the "initial inactive" status and "incomplete" status, it is possible to remind a professional to perform the clinical process rapidly in the same manner as the small icons 82.

The normal icons 81C and the small icons 82 are displayed only for the clinical process of which the plan is registered. Assuming that no clinical process requires being performed, the blank 83 is formed without the normal icons 81C or the small icons 82. It is possible to grasp various types of clinical processes with and without requirements, so that errors of performing unnecessary medical care can be prevented.

The patient list 71 is created according to the professional. There are differences between professionals in relation to the information items in the information item field 76, the patients in the patient field 77, and the progress of the clinical process indicated by the icons 81. Thus, it is possible to share information between professionals reliably for the progress of the clinical process of the patients. Each one of the professionals can recognize his or her preparation for next step of the clinical process, which can be performed properly.

The professional views the first information page 15A and checks the progress in the clinical processes for the patients. The professional refines the selection of the patients according to the patient type in the patient list 71 by use of the menu tabs 72, or selects the personal information in the patient field 77 to display the second information page 15B. Upon the occurrence of the user input for editing the page (yes in a step S120 in FIG. 22), the request generator 42 issues a request for editing in a step S130.

The request for editing generated by the request generator 42 of the client terminal apparatus 12 is received by the request receiving unit 46 in the medical support server apparatus 11, and transferred to the data control unit 47. The data control unit 47 selectively reads out the record information 16 from the record database 11A with necessity for page editing. The record information 16 being read out to the data control unit 47 is set in the page editor 48.

The page editor 48 edits the information page according to the record information 16 from the data control unit 47 in a step S220. Assuming that a request for editing from the request receiving unit 46 is for the second information page 15B, the second information page 15B is edited according to the medical care data from the data control unit 47. The first or second information page 15A or 15B after the page editing is transmitted by the transmission controller 49 to the client terminal apparatus 12 in a step S230.

In the client terminal apparatus 12, the GUI controller 41 causes the display panel 34B to display the first or second information page 15A or 15B after the page editing in a step S140. The professional views the second information page 15B, and can observe results of the diagnostic tests and the medical reports 26 at one time. Assuming that the progress of the professional of the information item of the progress information 50 is in the "unconfirmed" status, then the data control unit 47 changes the status to the "confirmed" status.

Assuming that the request for editing from the request receiving unit 46 is a request for refinement of selecting patients in the patient list 71 according to the patient type, then the patient list 71 in a form according to the patient type is created. Therefore, the progress of the clinical process according to the patient type can be grasped easily, owing to the patient list 71 including the information items in the information item field 76, the patient in the patient field 77, and the progress of the clinical process of the icons 81, in a manner suitable for the patient type.

The client terminal apparatus 12 repeats the above-described steps S120-S140 while there is no input for logout by manipulation of a professional (no in a step S150). Also, the medical support server apparatus 11 repeats the steps S220 and S230 while the request receiving unit 46 does not receive an input for logout (no in a step S240).

In FIG. 22, one of the client terminal apparatuses 12 and the medical support server apparatus 11 are illustrated for the flow of processing. However, the medical support server apparatus 11 actually receives requests for information distribution or requests for editing from a plurality of the client terminal apparatuses 12. The medical support server apparatus 11 performs plural tasks at the same time for the plural client terminal apparatuses 12, the tasks including creation of the first information page 15A, editing of the first and second information pages 15A and 15B, and information distribution of the first and second information pages 15A and 15B.

Figure 23:
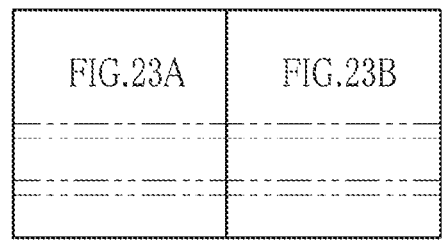
FIGS. 23, 23A and 23B are a screen view illustrating other preferred number window areas.
Figure 23A:
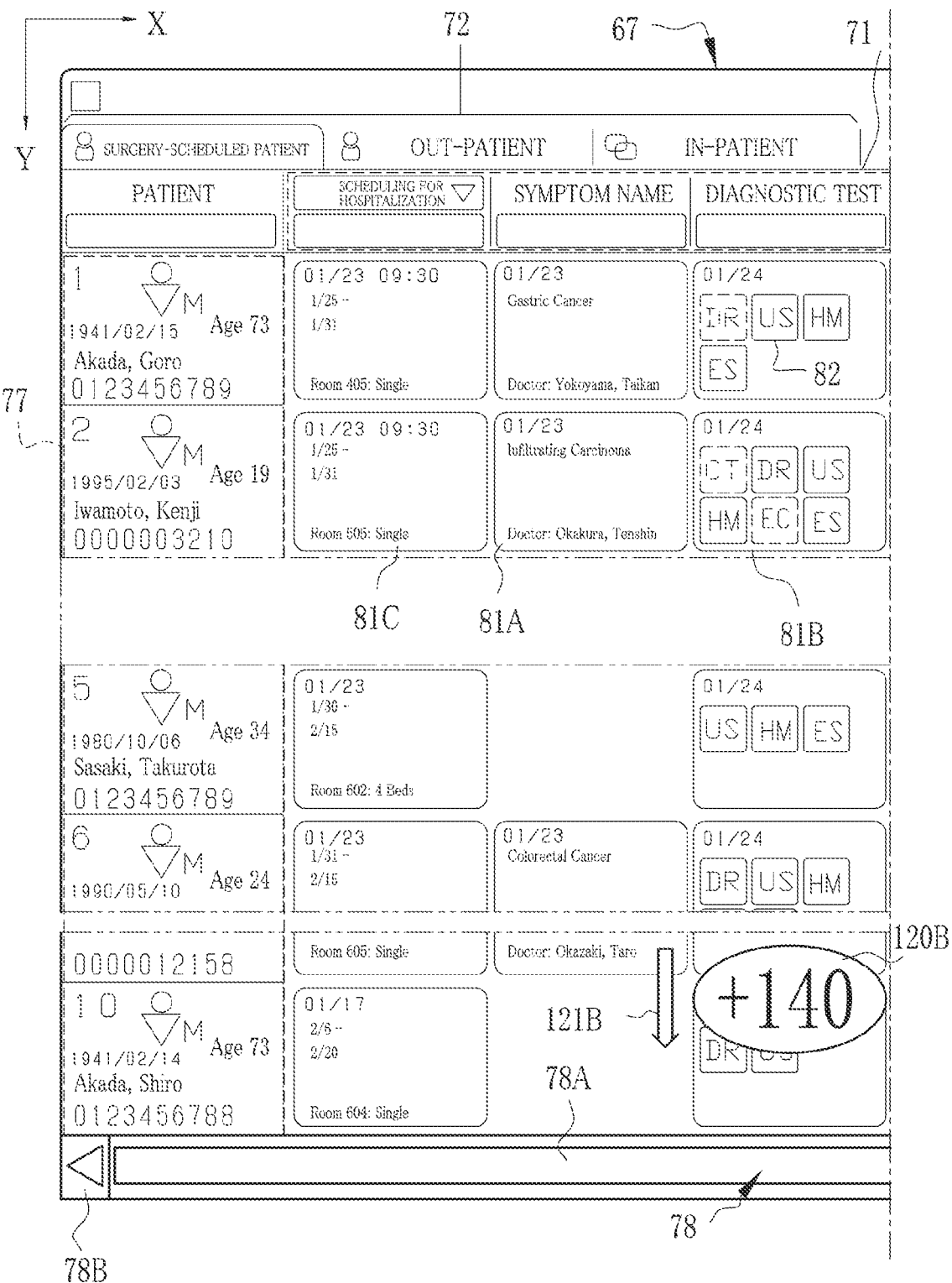
Figure 23B:
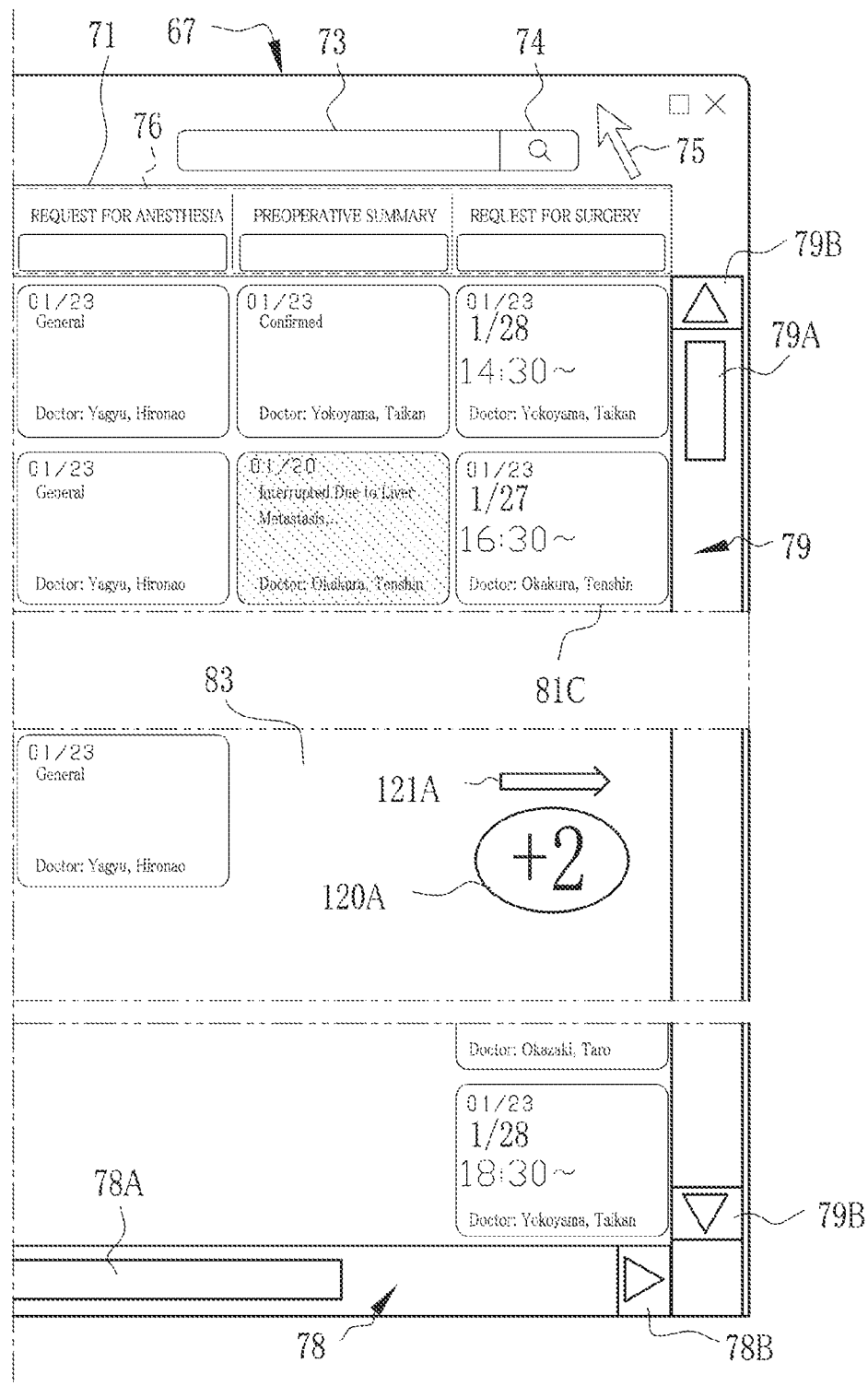

Note that the number window areas are not limited to the number window areas 80A and 80B of the tapered triangular shape in the first embodiment. In FIGS. 23, 23A and 23B, other preferred forms are illustrated. An information item number window area 120A or balloon (mark), and a patient number window area 120B or balloon (mark), are shaped in an elliptic form, and are disposed to surround the numbers for the information items and patients. Arrows 121A and 121B can be associated respectively with the number window areas 120A and 120B, to point directions of a hidden location of an undisplayed portion. The number window areas 120A and 120B are disposed with the icons 81 in an overlapped form in the same manner as the number window areas 80A and 80B, and displayed in a translucent form in achromatic gray.

Also, the number can be indicated without the use of a window area (mark) in place of the window area of the above embodiment in which the number is indicated. Furthermore, a display form with emphasis for the window area or the number can be used, for example, conspicuous red color can be used, or one of those can be turned on and off repeatedly in a winking manner. Also, the window area can be a circular form. The number can be contained in the window area eccentrically and so positioned as to point a direction of the hidden location of an undisplayed portion. In short, any suitable variants of the number in a window area can be used, and are not limited to the above embodiment.

Figure 24:
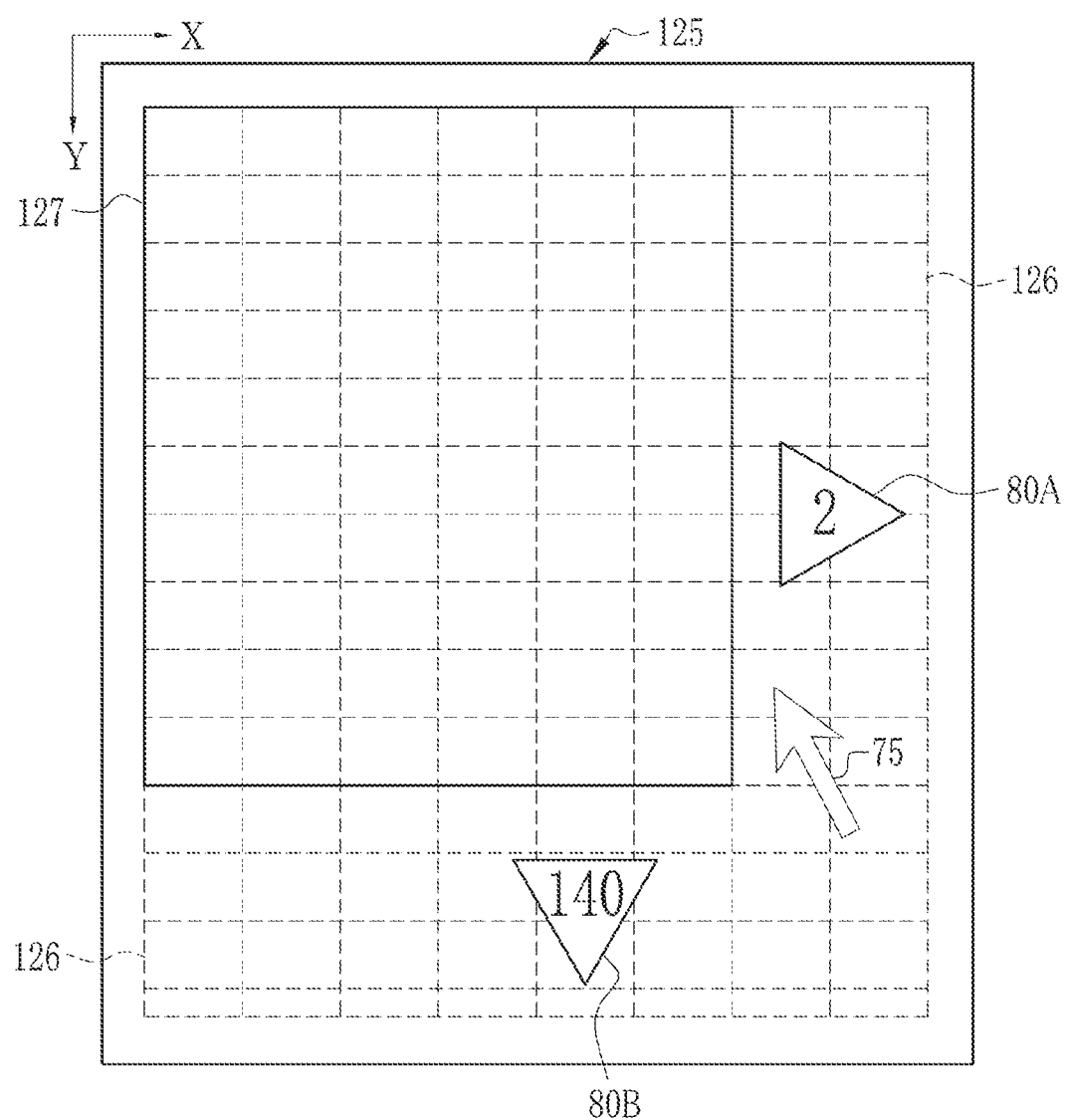
FIG. 24 is a screen view illustrating a floating window.

Furthermore, it is possible to display the number related to the undisplayed portion distinctly from the patient list 71, in a form unlike the patient list 71 in the first embodiment. In FIG. 24, a floating window 125 (float map) is illustrated. The floating window 125 is discrete from the patient list 71, and displays the number window areas 80A and 80B.

The floating window 125 displays a simplified form of an active display area of the patient list 71 with an area of an undisplayed portion. The floating window 125 includes plural frame elements 126 of the dotted line and a current frame 127 of the solid line. In the frame elements 126, all of the eight information items in the information item field 76 of the patient list 71 are arranged along the horizontal axis X. Personal information of the patient field 77 is arranged along the vertical axis Y for more than 10 patients. The current frame 127 displays the active display area in the first information page 15A among datasets of the personal information of the patient field 77 and information items in the information item field 76 in the patient list 71. A peripheral portion contained in the floating window 125 but disposed outside the current frame 127 corresponds to an undisplayed portion, and has the number window areas 80A and 80B disposed therein.

In the condition of FIG. 24, the personal information of ten patients of serial numbers 1-10 in the display sequence is displayed. Two information items on the right side among the eight information items are undisplayed. The personal information of the remaining patients other than the ten patients is undisplayed. This is the same as the condition of FIGS. 13A and 13B. Thus, a left side line and upper side line of the current frame 127 are aligned with respectively a left side line and upper side line of the floating window 125. The periphery of the current frame 127 is disposed to surround six of the frame elements 126 along the horizontal axis X and ten of the frame elements 126 along the vertical axis Y.

Figure 25:
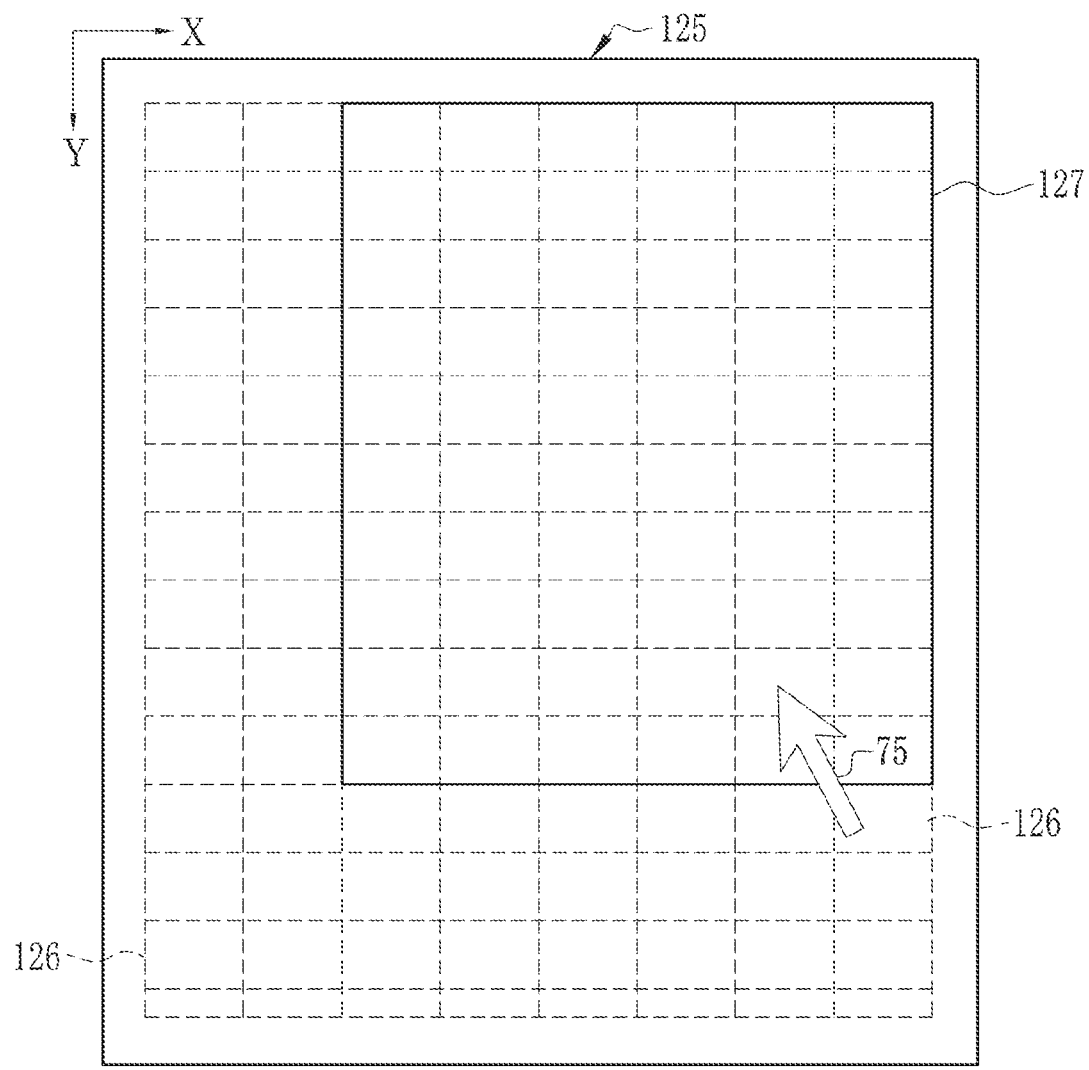
FIG. 25 is a screen view illustrating the floating window after a shift of a current frame.

The current frame 127 is shiftable inside the floating window 125 by use of the cursor 75. Shifting the current frame 127 changes over the display of the patient list 71. In FIG. 25, the current frame 127 is shifted to the right by an amount of two of the frame elements 126 along the horizontal axis X. Two information items on the right side, which have been undisplayed in FIG. 24, and the icons 81 associated with those become displayed in the first information page 15A. This is similar to the occurrence of scroll from the state of FIGS. 13A and 13B to the right side. In short, shifting the current frame 127 is a type of input action for the scroll in the same manner as pressing the sliders 78A and 79A and the arrow buttons 78B and 79B and rotating a wheel button of the mouse. Note that in case such an input action for scroll is performed to redisplay the undisplayed portion, the number window areas 80A and 80B are deleted in FIG. 25 in the same manner as the first embodiment.

Figure 26:
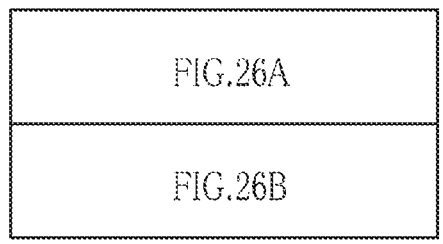
Figure 26B:
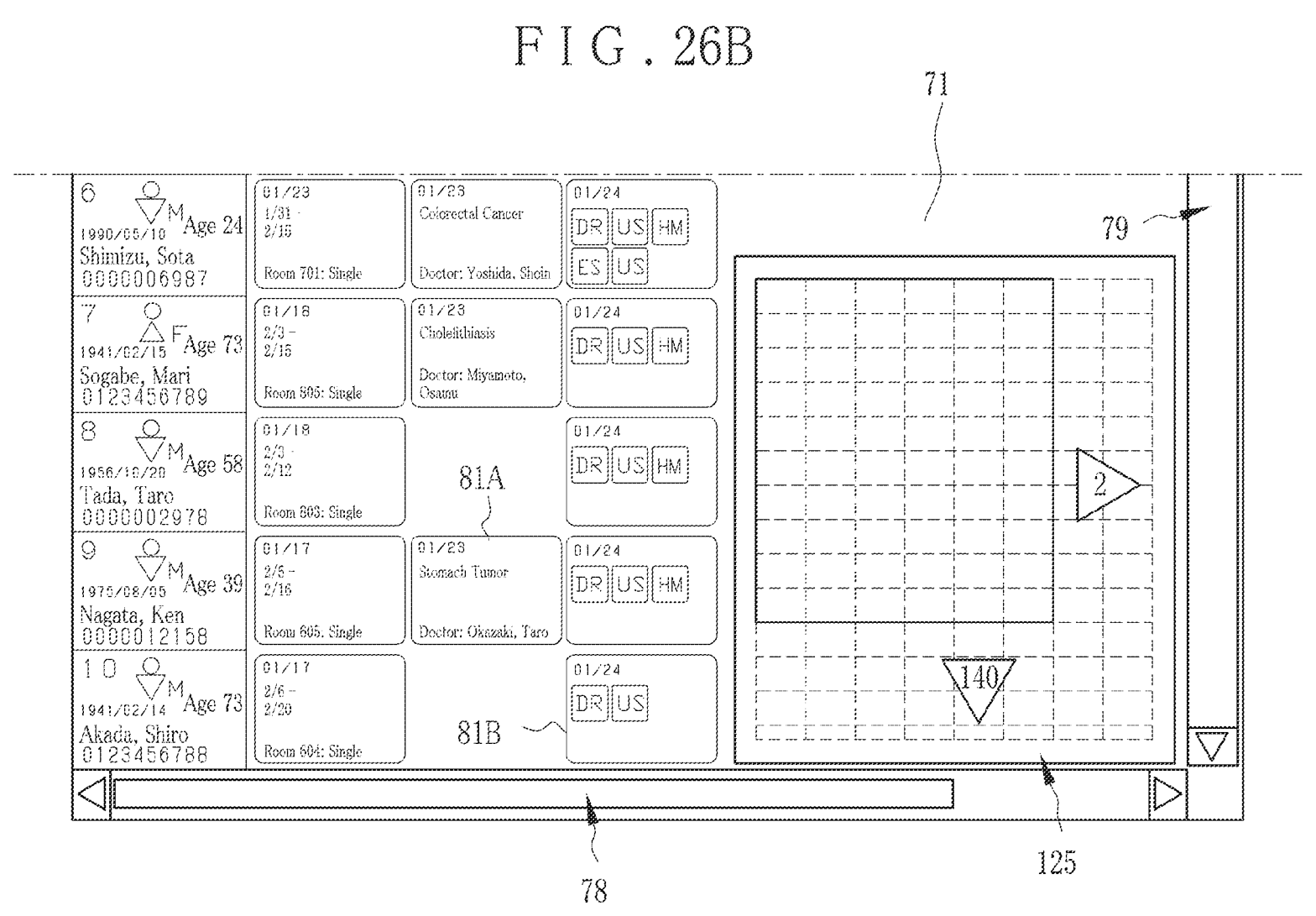

For example, the floating window 125 is displayed to overlap with a lower right portion of the patient list 71 as illustrated in FIG. 26B, which is a view on a lower side than FIG. 26A in FIG. 26. It is also possible to display the floating window 125 to overlap with the schedule area 65 or the mail area 66. Also, it is possible to construct the floating window 125 with changeover between turn-on and turn-off states of display according to user preferences.

Thus, it is possible for a professional to grasp the data amount of the active display area and the undisplayed portion entirely by viewing the floating window 125. The number window areas 80A and 80B make it possible to recognize the data amount of the undisplayed portion.

In the first embodiment, the number window areas 80A and 80B are deleted upon an action for the scroll. However, it is possible to keep the number window areas 80A and 80B displayed always in a display state irrespective of an input action for scroll to redisplay the undisplayed portion.

Figure 27:
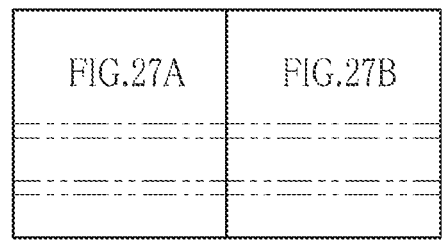
FIGS. 27, 27A and 27B are a screen view illustrating a preferred embodiment in which window areas remain irrespective of scroll.
Figure 27A:
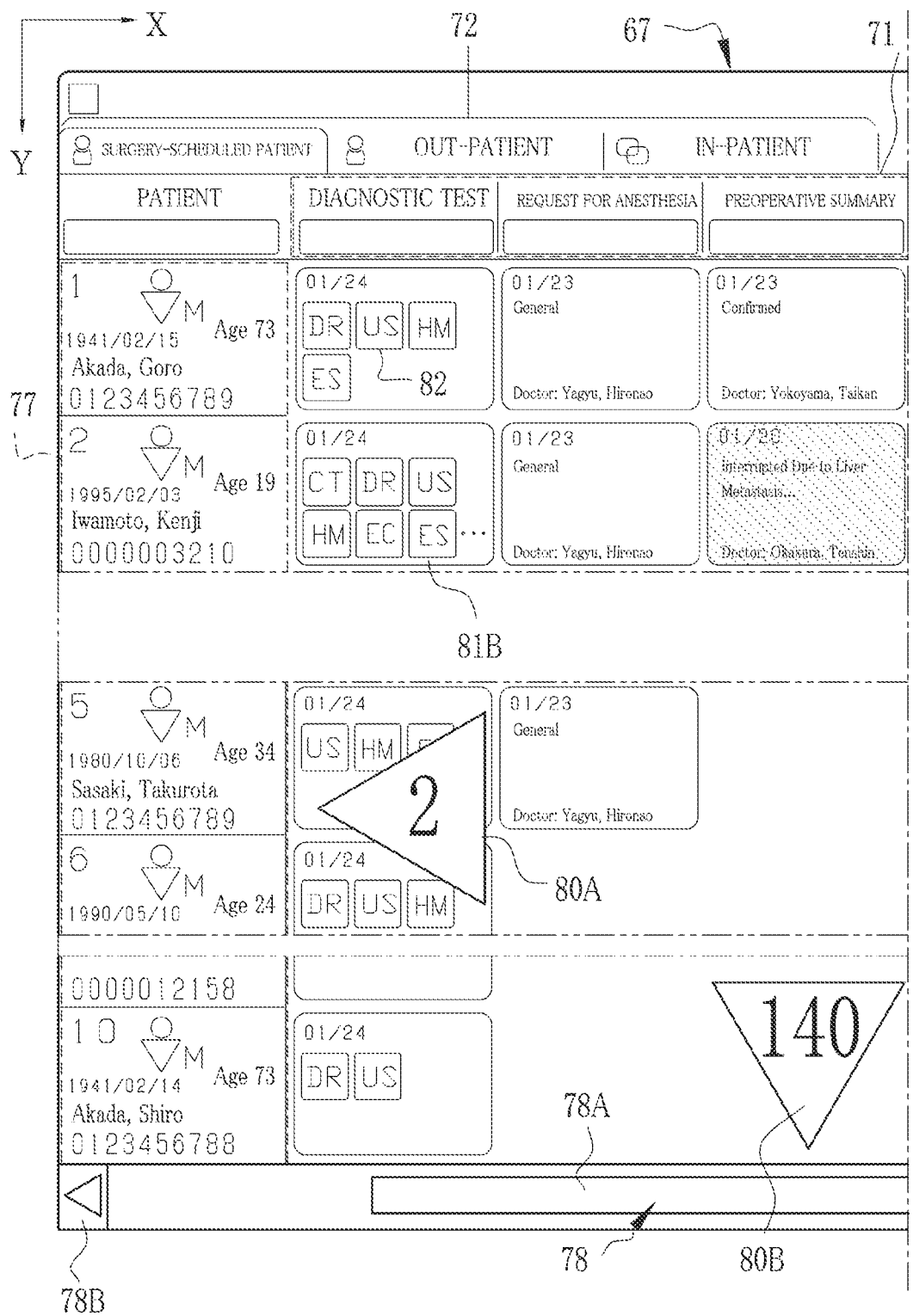
Figure 27B:
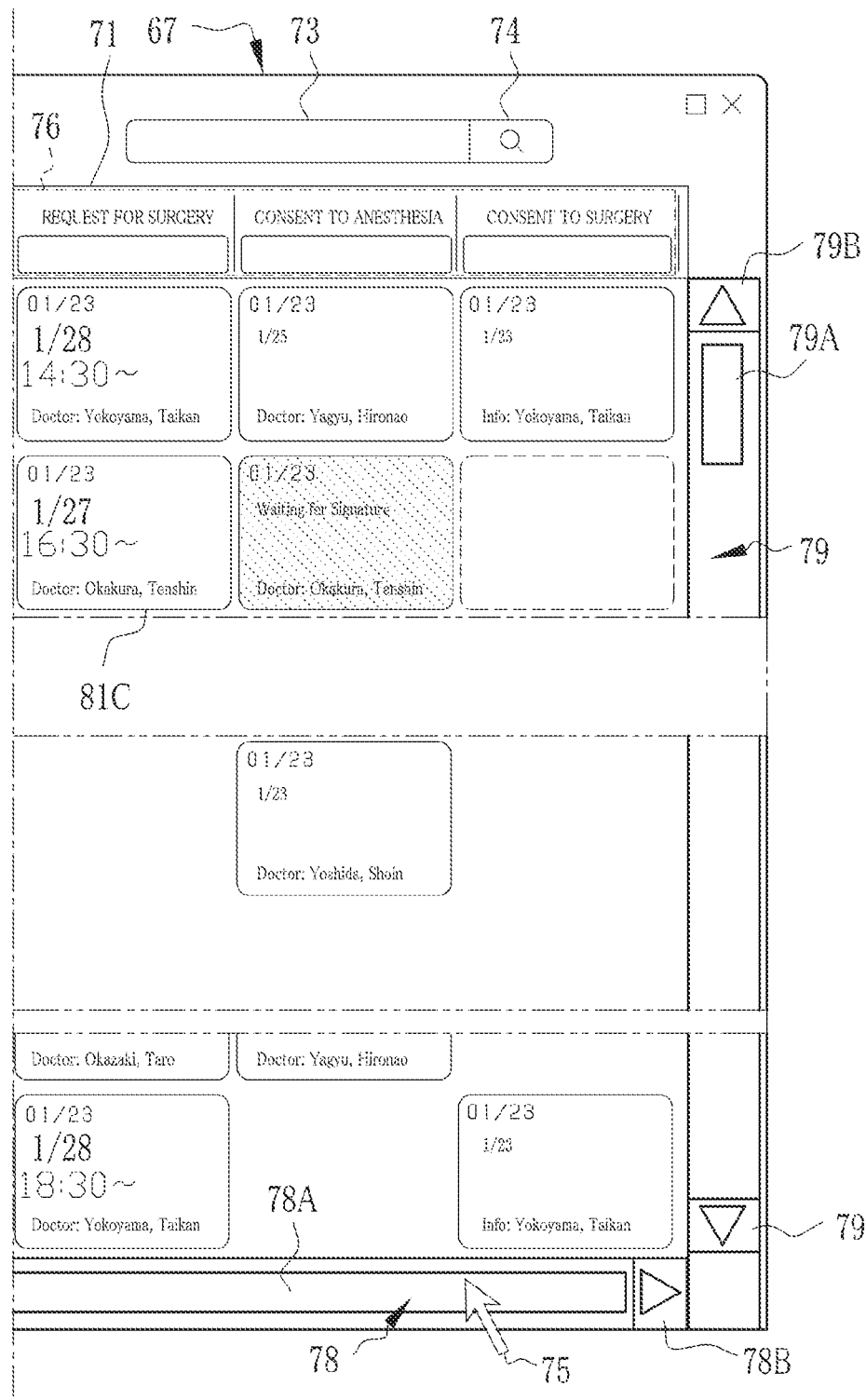

In case the input action for the scroll to the right from the state of FIGS. 13A and 13B is performed, data are displayed, the data including information items of the patient consent to the anesthesia and patient consent to the surgery, and the icons 81 associated with the information items. The number window areas 80A and 80B are displayed with the patient list 71 in an overlapped manner in FIGS. 27, 27A and 27B. This is unlike the state of FIGS. 15A and 15B from which the number window areas 80A and 80B of the first embodiment are deleted. However, other data are undisplayed, including information items of scheduling of hospitalization and a symptom name, and the icons 81. The information item number window area 80A is displayed at the center of the left of the patient list 71 in the tapered shape to point the left side.

Also, the number window areas 80A and 80B in the floating window 125 in FIG. 24 can be kept indicated even upon an input action for scroll to redisplay the undisplayed portion. Furthermore, the number window areas 80A and 80B can be displayed in the patient list 71 of FIGS. 13A and 13B at the same time as the number window areas 80A and 80B are displayed in the floating window 125 of FIG. 24. The number window areas 80A and 80B in the patient list 71 can be turned off upon occurrence of an input action for scroll to redisplay the undisplayed portion, and the number window areas 80A and 80B in the floating window 125 can be kept indicated.

Second Embodiment

Figure 28:
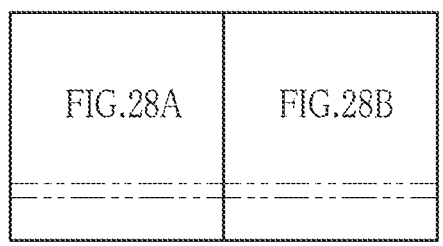
Figure 28A:
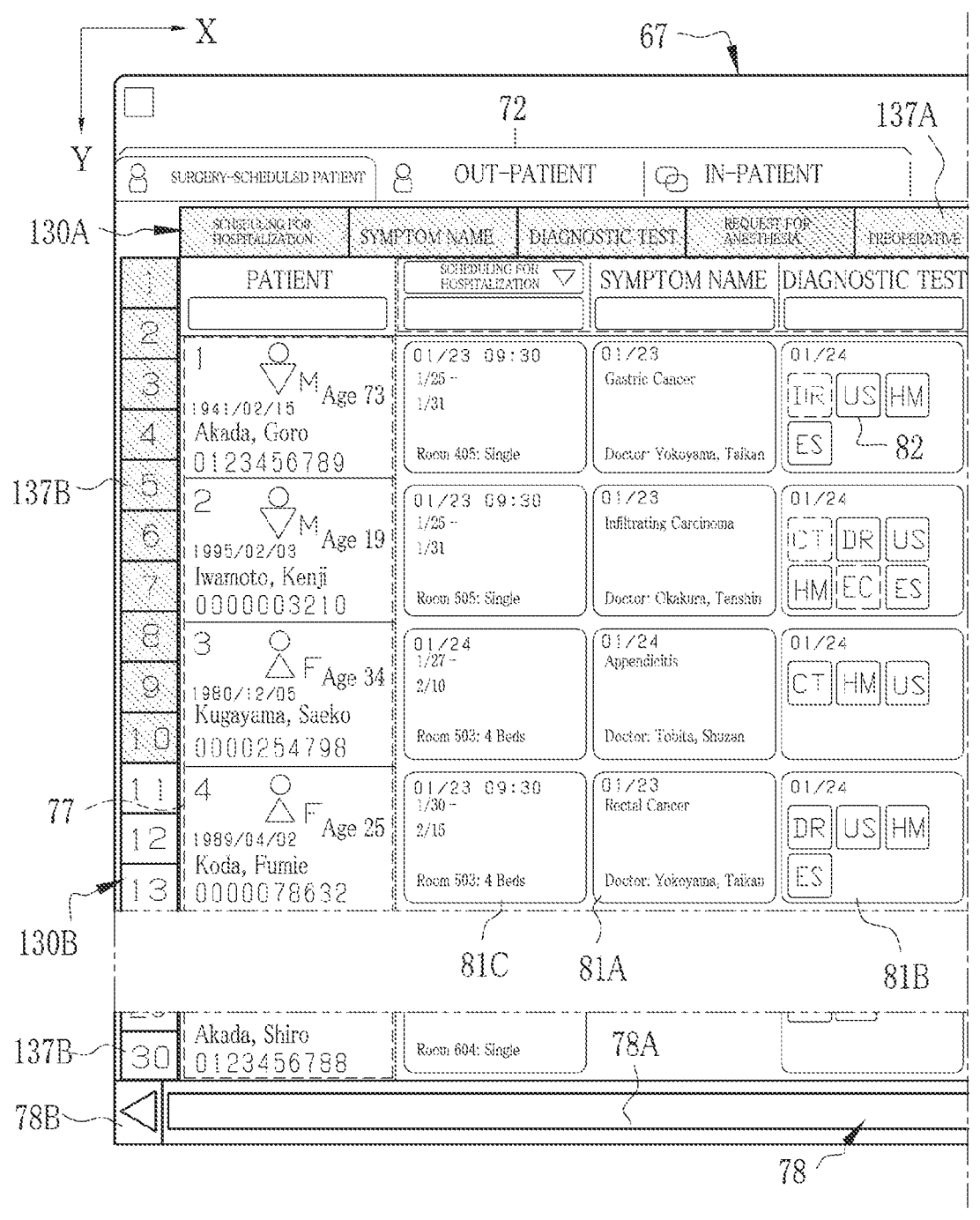
Figure 28B:
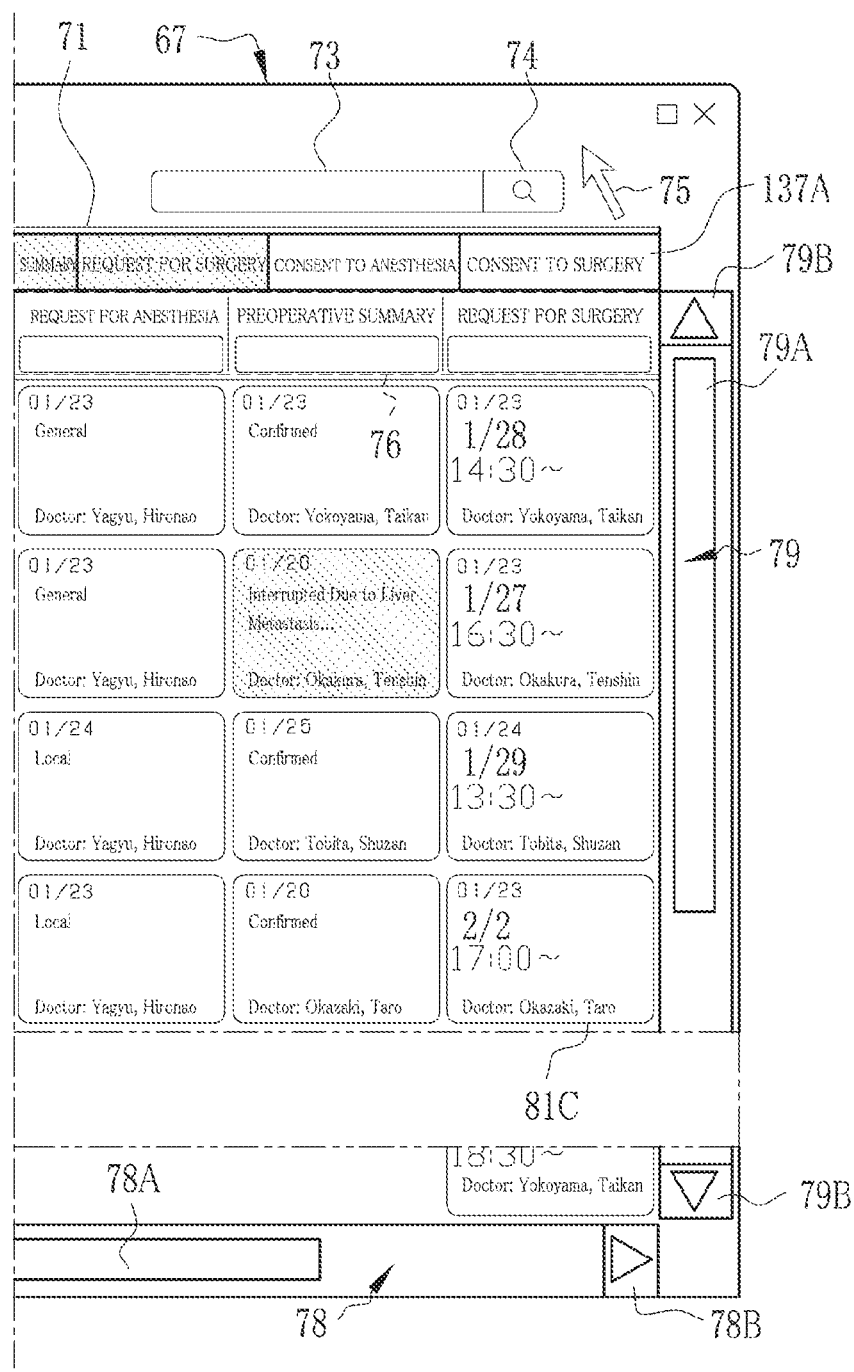

In FIGS. 28, 28A and 28B, a second preferred embodiment is illustrated. The page editor 48 performs display processing to display a first data list area 130A for information items, and a second data list area 130B for patients (patient bodies) in the patient list 71 while the horizontal and vertical scroll bars 78 and 79 are displayed in the patient list 71. The first data list area 130A extends along the horizontal axis X (first axis) and is disposed higher than the information item field 76 with the information items. The second data list area 130B extends along the vertical axis Y (second axis) and is disposed on a left side of the patient field 77 with the personal information of patients.

Figure 29:
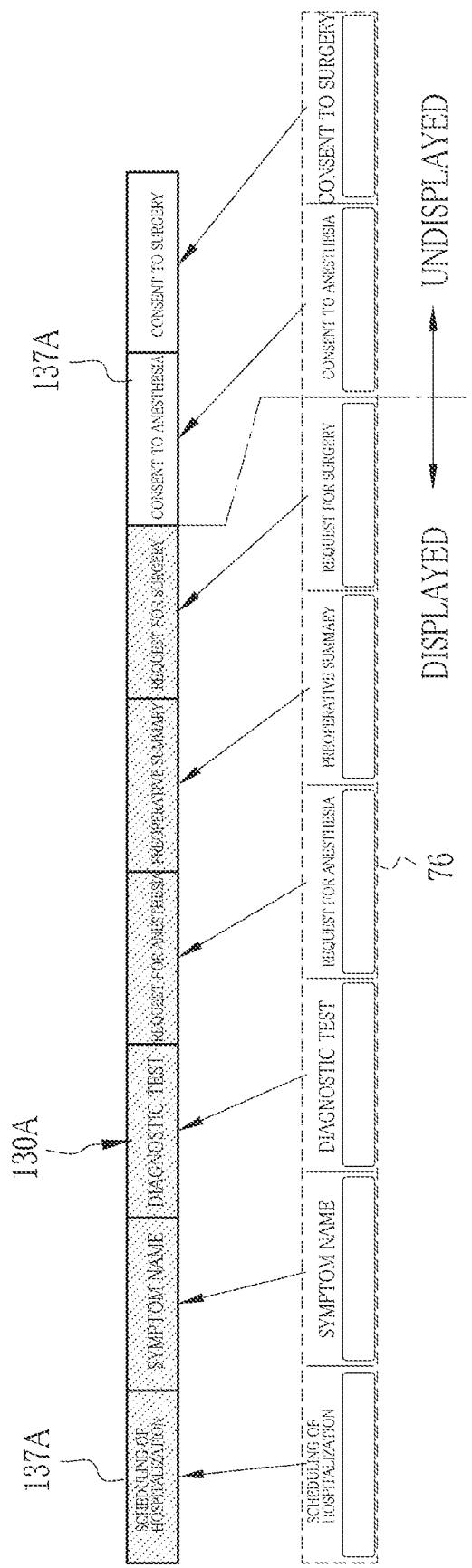
FIG. 29 is an explanatory view illustrating a relationship between information items and first block cells.

In FIG. 29, first block cells 137A are arranged in the first data list area 130A in the number equal to the total of the information items in both of the active display area and undisplayed portion. In FIGS. 28A and 28B, information items in the active display area are six, including scheduling of the hospitalization, symptom name, diagnostic test, request for the anesthesia, preoperative summary and request for the surgery. Information items in the undisplayed portion are the patient consent to the anesthesia and patient consent to the surgery. Total of the information items are eight. Thus, the first data list area 130A is constituted by eight of the first block cells 137A. In the first block cells 137A, alphanumeric information is indicated for scheduling of the hospitalization, symptom name and diagnostic test to describe the information items.

In FIG. 30, the second data list area 130B is constituted by as many second block cells 137B as the number of the datasets of all the personal information as a sum of the numbers of datasets of the personal information in the active display area and the undisplayed portion. In FIGS. 28A and 28B, the number of the datasets of the personal information in the active display area is 10. The number of the datasets of the personal information in the undisplayed portion is 20. The total of the datasets of the personal information is 30. Thus, the second data list area 130B is constituted by 30 of the second block cells 137B. Number data are indicated in the second block cells 137B for a sequence of the indication.

Among all of the first block cells 137A in the first data list area 130A, the first block cells 137A corresponding to the active display area are different in a display form from the first block cells 137A corresponding to the undisplayed portion, as indicated by the hatching in the first block cells 137A corresponding to the active display area for distinction. For example, a color for the first block cells 137A corresponding to the active display area is dark blue. A color for the first block cells 137A corresponding to the undisplayed portion is light blue. In FIGS. 28A and 28B, the first block cells 137A corresponding to the active display area are six block cells on the left side corresponding to the scheduling of the hospitalization, symptom name, diagnostic test, request for the anesthesia, preoperative summary and request for the surgery. The first block cells 137A corresponding to the undisplayed portion are two block cells on the right side corresponding to the patient consent to the anesthesia and patient consent to the surgery.

A display form of the second block cells 137B of the second data list area 130B is different between those corresponding to an active display area and those corresponding to an undisplayed portion in the same manner as the first block cells 137A of the first data list area 130A. For example, a color of the second block cells 137B for the active display area is dark blue. A color of the second block cells 137B for the undisplayed portion is light blue. In FIGS. 28A and 28B, 10 of the second block cells 137B on the upper side correspond to the active display area for the personal information of 10 patients. 20 of the second block cells 137B on the lower side correspond to the undisplayed portion for the personal information of 20 patients.

Figure 31:
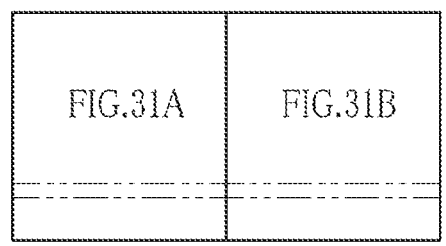
Figure 31A:
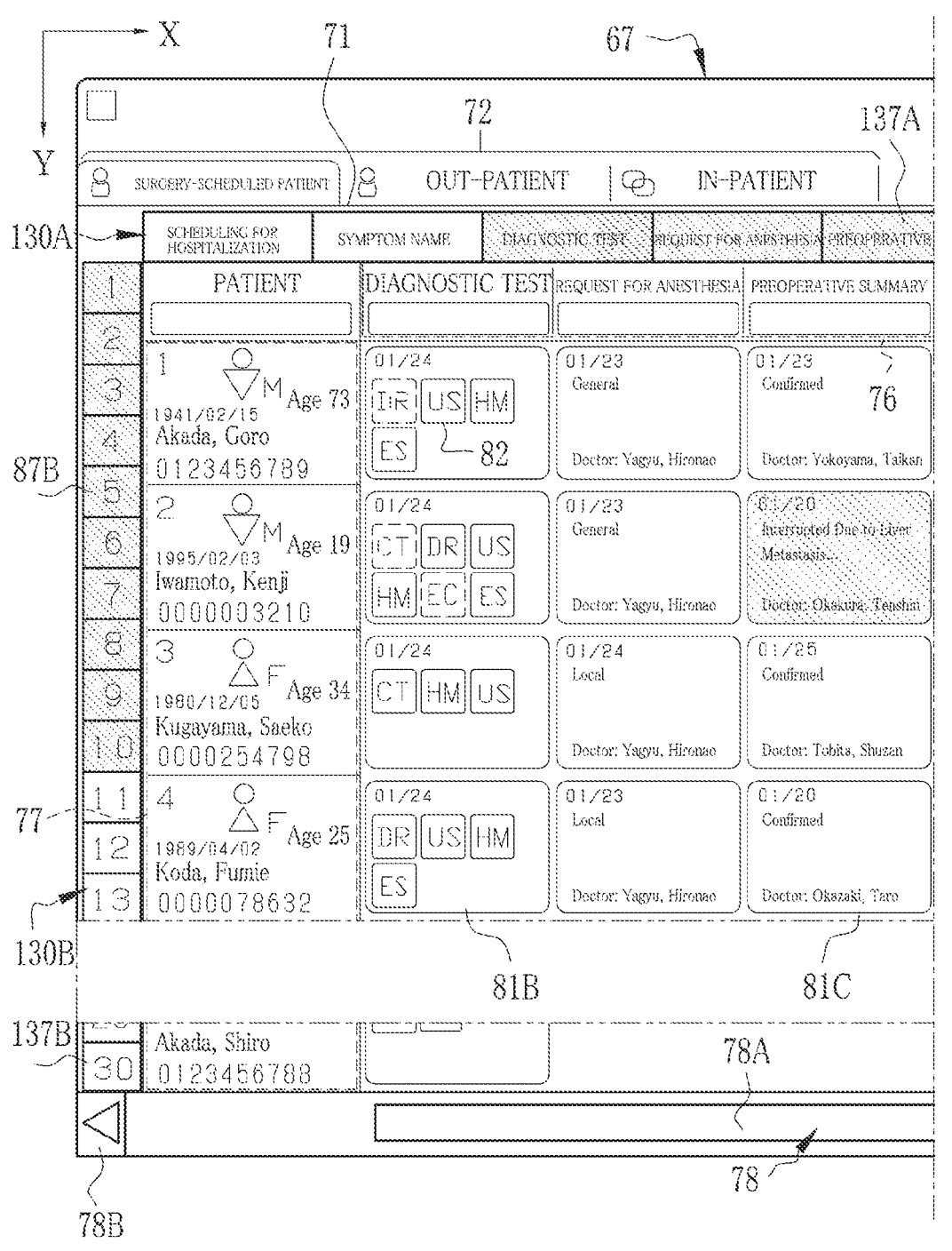
Figure 31B:
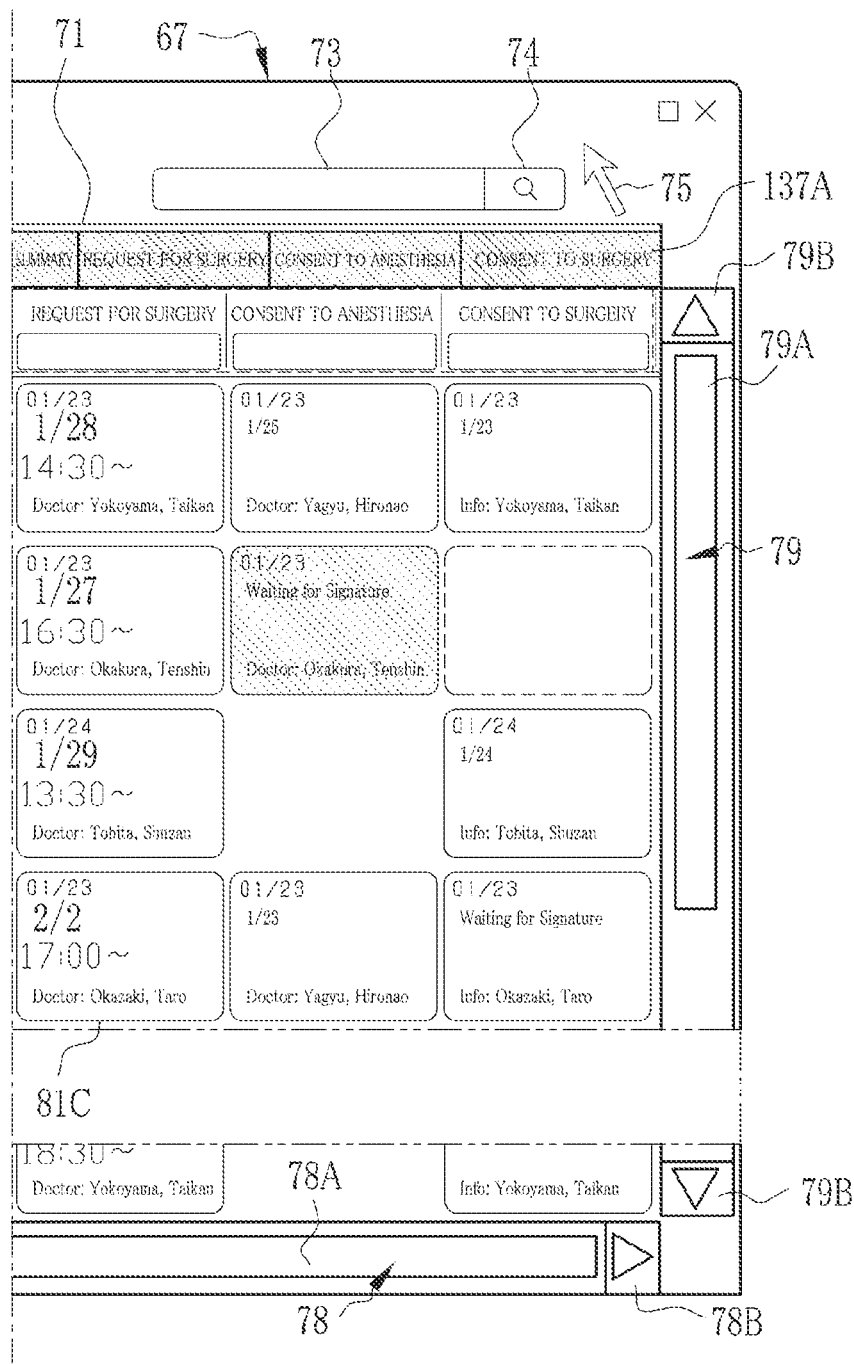

The undisplayed portion becomes displayed upon an input action for scroll, such as press of the sliders 78A and 79A and the arrow buttons 78B and 79B with the cursor 75, and rotation of a wheel button of a mouse. In FIGS. 31, 31A and 31B, the input action for scroll to the right is performed. Information items of the patient consent to the anesthesia and patient consent to the surgery in the undisplayed portion in FIGS. 28A and 28B and the icons 81 disposed with those become displayed in the first information page 15A. In contrast, the information items of the scheduling of the hospitalization and symptom name, and the icons 81 associated with those displayed in FIGS. 28A and 28B become undisplayed. Display positions of the information item field 76 and the patient field 77 are unchanged even upon occurrence of an action for scroll.

In case the input action for the scroll is performed, the first and second block cells 137A and 137B corresponding to the active display area and the first and second block cells 137A and 137B corresponding to the undisplayed portion are changed over to one another. In FIGS. 31A and 31B, the first block cells 137A in the first data list area 130A corresponding to the active display area are six information items on the right side, inclusive of the diagnostic test, request for anesthesia, preoperative summary, request for surgery, patient consent to anesthesia and patient consent to the surgery. The first block cells 137A corresponding to the undisplayed portion are two information items of the left side, inclusive of the scheduling of hospitalization and symptom name.

Figure 32:
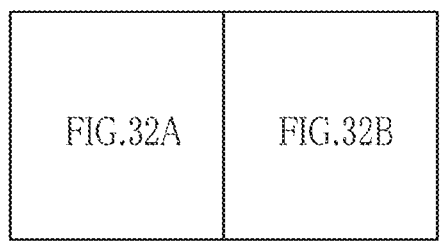
Figure 32A:
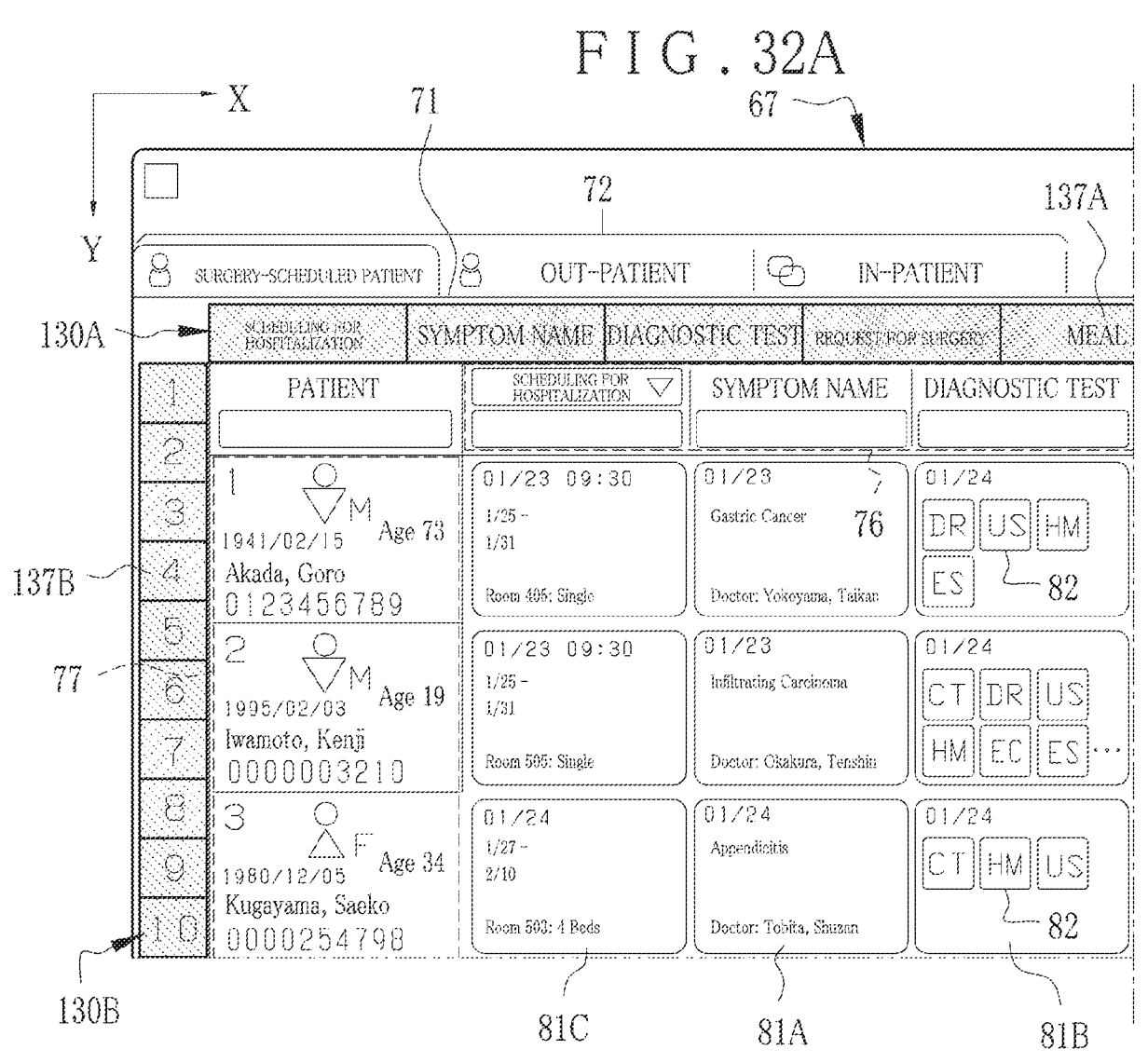

In FIGS. 32, 32A and 32B, the patient list 71 is illustrated, in which the professional type of the professional of whom the professional ID is input by use of the login page is a dietician, and the in-patient tab 72C in the menu tabs 72 is selected. The information item field 76 in the patient list 71 displays information items of the symptom name, meal, scheduling of the hospitalization, diagnostic test, request for the surgery, patient care plan, nutrition plan and follow-up plan, which are described in information items of the dietician for the "in-patient" as patient type in the type mapping table 84 in FIG. 16. In FIGS. 32A and 32B, the information items for the symptom name, meal, scheduling of the hospitalization, diagnostic test, request for the surgery and patient care plan are in the active display area. The information items for the nutrition plan and follow-up plan are in the undisplayed portion. See the display form of the first block cells 137A in the first data list area 130A.

As the first data list area 130A or the second data list area 130B is displayed in the patient list 71, a professional can grasp the data amount of the information items or personal information of the active display area and the undisplayed portion, and the data amount of the total of the information items or the total of the datasets of the personal information, according to the information items in the information item field 76 and the first block cells 137A of the first data list area 130A or according to the personal information in the patient field 77 and the second block cells 137B of the second data list area 130B. Therefore, the professional can view the patient list 71 with good visual perceptibility and good interface functionality as a result of solving the problem of the conventional construction, as user accessibility and time related to viewing the patient list 71 can be estimated easily.

The first data list area 130A is disposed on the upper side of the information item field 76 along the horizontal axis X. The second data list area 130B is disposed on the left side of the patient field 77 along the vertical axis Y. Thus, it is possible easily to grasp the data amount of the personal information or information items in the active display area and undisplayed portion, and the data amount of the total of the information items or total of the datasets of the personal information, as the data list areas 130A and 130B are arranged next to the display position of the information items or the personal information.

The first and second block cells 137A and 137B for the active display area and the first and second block cells 137A and 137B for the undisplayed portion are displayed in a recognizable manner. Thus, data amounts of the active display area and the undisplayed portion can be clarified for recognition. Also, alphanumeric information for information items is displayed in the first block cells 137A. The professional can be informed of content information of the information items in the undisplayed portion without scroll operation.

Third Embodiment

In the second preferred embodiment, the first and second block cells 137A and 137B of the undisplayed portion are visually distinct from those of the active display area. A feature of a third preferred embodiment is provided in addition to or in place of the second preferred embodiment. At least one of the first block cells 137A and the second block cells 137B can be displayed with emphasis, for example, with red color of conspicuousness, the first block cells 137A corresponding to information items in an alert condition (for which attention is required), the second block cells 137B corresponding to personal information of patients in an alert condition.

Figure 33:
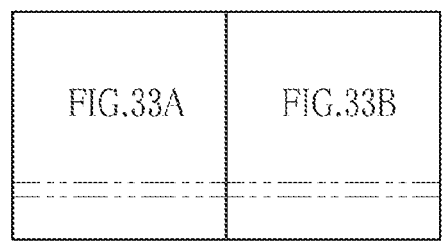
Figure 33B:
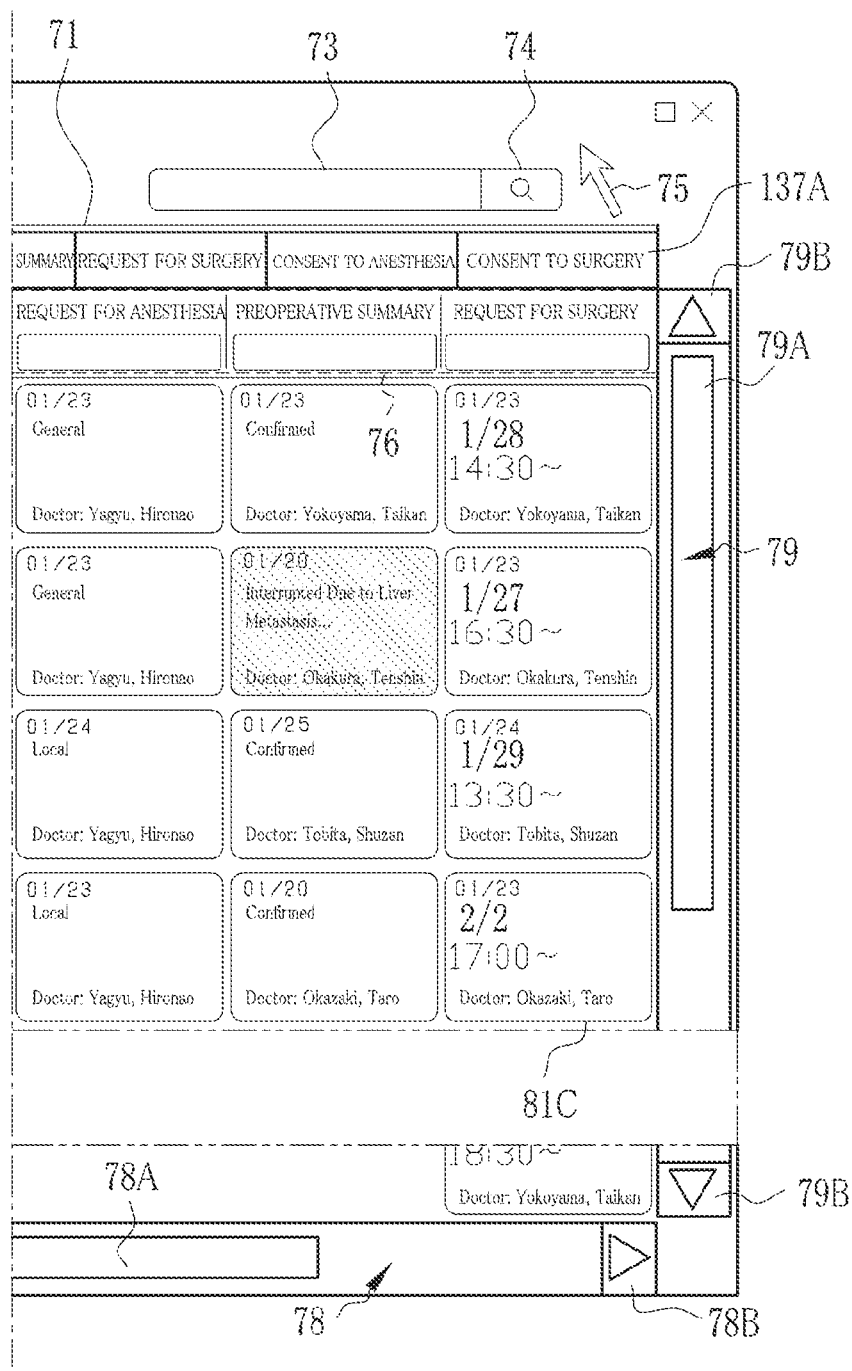

In FIGS. 33, 33A, 33B and 34, the second block cells 137B of the serial numbers 2, 4, 9 and the like according to the display sequence are displayed with an emphasis as indicated by the hatching to correspond to the personal information of the patients in an alert condition. Also, the personal information of the serial numbers 2, 4, 9 and the like according to the display sequence in association with the second block cells 137B is displayed with an emphasis as indicated by the hatching, among the datasets of the personal information arranged in the patient field 77. In FIGS. 33A and 33B, the personal information of the serial numbers 2 and 4 is illustrated.

Examples of patients in an alert condition are patients for whom a clinical process must be performed on the same day as login of a professional inputting his or her professional ID with the login page. An example of the clinical process to be performed is a diagnostic test of which a date of a request is the same day as the login or the day before the same day and of which the progress is the "non-tested" status, on a condition of a technician as a professional. An example of the clinical process to be performed is a patient consent to a surgery of which a date of the login is one week before the scheduled date of the surgery and of which the progress is in the "initial inactive" status and "incomplete" status, on a condition of a doctor as a professional. To this end, information of an alert condition (requirement of the attention) is set automatically by the data control unit 47 according to the progress of the clinical processes recorded as the progress information 50.

Thus, the second block cells 137B with information of the alert condition of a clinical process to be performed on the same date and the personal information corresponding to the second block cells 137B are indicated with emphasis, so that priority of the patient for whom the clinical process should be performed is clarified distinctly. Even while the personal information of the patient with the information of the alert condition is included in the undisplayed portion, it is possible to inform a professional of the information of the alert condition even for the patient with the personal information in the undisplayed portion. Missing the clinical process to be performed on the same date can be prevented reliably.

In FIGS. 33A and 33B, the second block cells 137B corresponding to the personal information of patients in the alert condition and personal information corresponding to the second block cells 137B are displayed with emphasis. However, the first block cells 137A corresponding to the information items in the alert condition can be indicated with emphasis. Among the information items arranged in the patient field 77, information items corresponding to the first block cells 137A indicated with emphasis can be displayed with emphasis. Also, it is possible for a professional to predetermine the information of the alert condition manually by use of the schedule area 65.

Examples of the patients in an alert condition include patients for whom performance of the clinical process is scheduled on the same date as the date of login, patients for whom the progress of the clinical process is the "initial inactive" status, "incomplete" status, "non-tested" status or "unconfirmed" status, patients for whom the progress of the clinical process has not become in the "completed" status or "confirmed" status even after lapse of the period of a predetermined term.

The data list areas 130A and 130B can be displayed at locations distant from the location of the information items or personal information. However, it is preferable to display the data list areas 130A and 130B at locations distant from the location of the information items or personal information, because it is possible easily to recognize the data amount of the information items or personal information in the active display area and undisplayed portion, and the data amount of the total of the information items and the total of the datasets of the personal information.

In the second and third embodiments, only the serial numbers are indicated in the second block cells 137B of the second data list area 130B. However, alphanumeric information can be indicated in the second block cells 137B for expressing the identification data of the patient such as his or her name and case ID, in the same manner as the first block cells 137A of the first data list area 130A.

Statuses of the progress indicated by the normal icons 81C are not limited to the "initial inactive" status, "incomplete" status and "completed" status. Statuses of the progress indicated by the small icons 82 are not limited to the "non-tested", "unconfirmed" and "confirmed" statuses. For example, examples of the "incomplete" status include unwanted interruption of the clinical process after discovery of an additional symptom in the information item of the preoperative summary of the case ID 0000003210 in FIG. 7, or interruption for time reasons, and waiting for signature (submission) of patient consent for surgery, or usual situation without particular problems. Therefore, examples of the status of the "incomplete" status can be two statuses including an "interrupted" status and "waiting" status, the "interrupted" status being for unwanted interruption with an anomaly or the like, the "waiting" status being for a usual situation of wait without particular problems.

Examples of the progress indicated by the small icons 82 can include a "started but incomplete" status for a period after confirming the request in the step S11 in FIG. 8 until uploading the report in the step S16, in addition to the "non-tested" status, "unconfirmed" status and "confirmed" status. Also, it is possible to predetermine a "tested but unreported" status for a period after uploading a result of a diagnostic test in the step S14 in FIG. 8 until uploading the report in the step S16, and an "uploaded but unconfirmed" status for a period after uploading the result of the diagnostic test in the step S14 in FIG. 8 until producing the report in the step S15.

Figure 35:
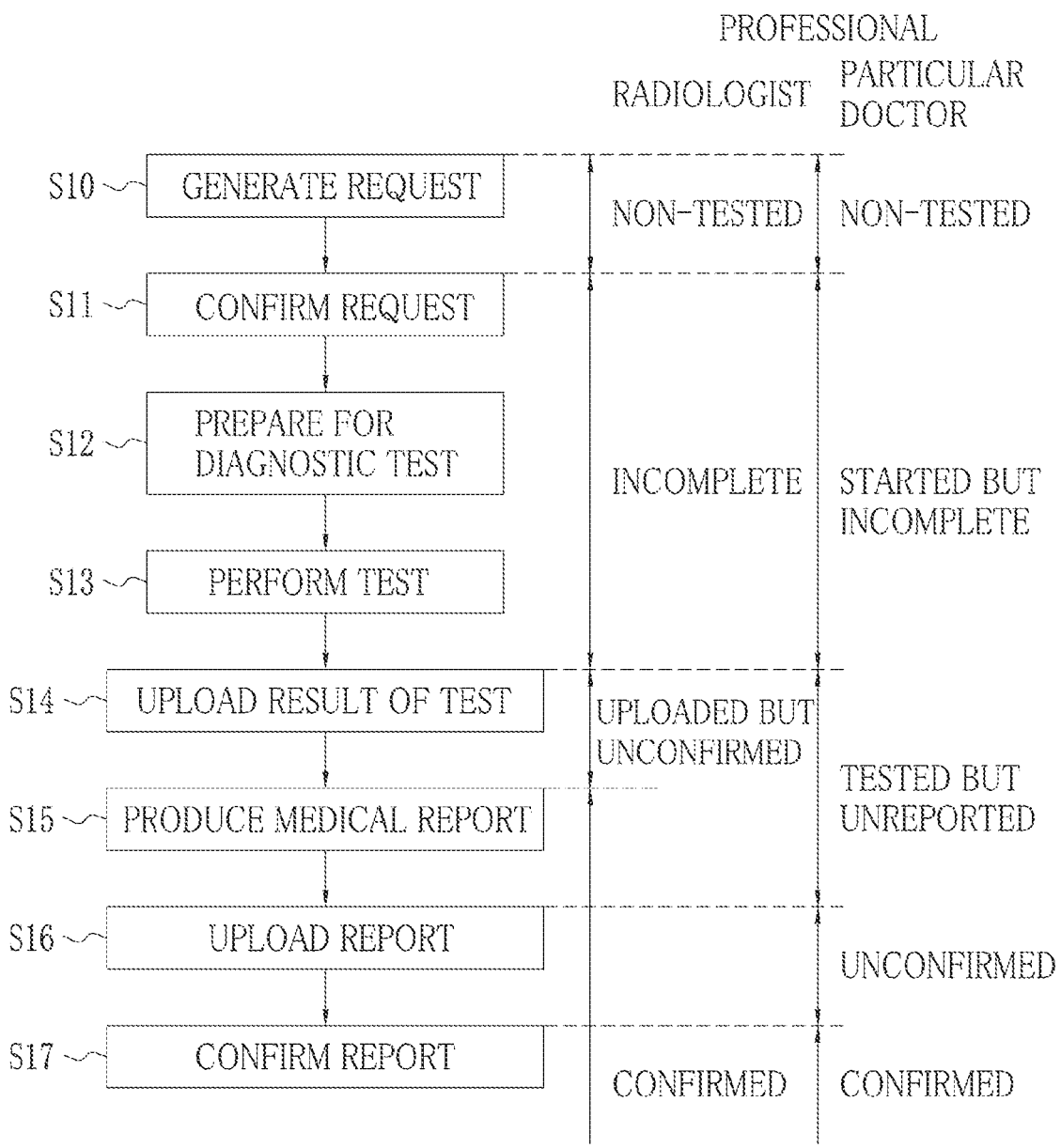
FIG. 35 is a flow chart illustrating an example in which the progress is changeable according to a professional type.

Also, it is possible to change a display form of the progress with the small icons 82 according to the types of the professionals, and to set the display form of the progress different between the professionals. In FIG. 35, examples of statuses of the progress for a particular doctor (patient's doctor) who issues a request are a "non-tested" status, "started but incomplete" status, "tested but unreported" status, "unconfirmed" status and "confirmed" status. The "non-tested" status is a status in a period after the step S10 or the generation of the request until the step S11 or confirmation of the request. The "started but incomplete" status is a status in a period after the step S11 or confirmation of the request until the step S14 or uploading of a result of the diagnostic test. The "tested but unreported" status is a status in a period after the step S14 or uploading of the result of the diagnostic test until the step S16 or uploading of the medical report. The "unconfirmed" status is a status in a period after the step S16 or uploading of the medical report until the step S17 or confirmation of the medical report. The "confirmed" status is a status in a period after the step S17 or confirmation of the medical report.

For the radiologist producing the medical reports 26, the "non-tested" status and "started but incomplete" status are the same as those for the particular doctor. An "uploaded but unconfirmed" status is determined for a period after uploading a result of the diagnostic test in the step S14 until producing the report in the step S15. A "confirmed" status is determined for a period after producing the report in the step S15. Thus, the progress can be indicated finely for professionals by changing the progress indicated with the small icons 82 according to the professional type. Also, the progress indicated by the normal icons 81C can be changed according to the professional type similarly.

In the above embodiments, the special icon 81B having the small icons 82 is used for expressing the progress of the clinical process of the same category of the diagnostic tests. However, a plurality of the small icons 82 contained in the special icon 81B are not necessarily related to the same category for the plural clinical processes. However, indication of the progress is not easily recognizable assuming that the small icons 82 are related to various categories, because there is no relevancy between the small icons 82. Thus, it is preferable for the small icons 82 included in the special icon 81B to express the progress of the clinical processes of the same category.

Other examples of clinical processes of the same category are processes of a patient consent to the anesthesia and patient consent to the surgery. Further examples of clinical processes are tasks of measuring plural vital signs, such as a heart rate, respiration rate, blood pressure, body temperature and the like of a patient.

In the above embodiments, the second information page 15B is displayed in case the personal information in the patient field 77 is selected by the cursor 75. However, it is possible to set the normal icons 81C or the small icons 82 selectable by use of the cursor 75, so as to display the second information page 15B in response to selection of the normal icons 81C or the small icons 82.

Examples of medical professionals in the invention can be a physical therapist for care of rehabilitation of a patient, pharmacist for preparation of drugs and guide of using drugs to a patient, and the like. It is possible as illustrated in FIG. 35 to classify doctors into particular doctors (patient's doctor) for direct care of patients and radiologists for producing the medical reports 26, and to classify technicians into radiology technicians and ultrasound technicians. In short, types of the professionals can be classified more finely for requirements.

In the above embodiments, the information items, personal information and progress in the patient list 71 are displayed differently for each of the patients and clinical processes in relation to each of the professionals. However, at least one of the information items, personal information and progress in the patient list 71 can be displayed differently. Also, the information items, personal information and progress in the patient list 71 are displayed differently for each of the patient types. However, at least one of the information items, personal information and progress in the patient list 71 can be displayed differently for the patient type.

Also, a diagnostic test of which the progress is indicated by the small icons 82 can be at least one of the imaging, sample test and physiological test in place of all of the imaging, sample test and physiological test. Furthermore, the examples of the patient types may additionally include an in-home patient who is cared by mobile staff (doctor or caregiver) at his or her home.

In the above embodiments, the patient list 71 has the icons 81 arranged regularly in the plural arrays. However, the patient list 71 of the invention can have alphanumeric information in relation to the clinical process instead of the icons 81.

In the above various embodiments, the medical support apparatus of the invention is the medical support server apparatus 11 for the information distribution of the first and second information pages 15A and 15B to the client terminal apparatus 12 in response to the request for the information distribution. However, a medical support apparatus can be constituted by the client terminal apparatus 12 as illustrated in FIG. 36. Elements similar to those of the above embodiments are designated with identical reference numerals.

There is a difference between structures of FIG. 36 and the above embodiments. The control program 45 is run in the CPU 32B of the client terminal apparatus 12 by use of the storage medium 30B of the client terminal apparatus 12 previously storing the control program 45, so that the CPU 32B functions with the data control unit 47 and the page editor 48. Also, the record information 16 is stored in the storage medium 30B.

To this end, the request generator 42 transmits plural requests for processing to the data control unit 47. The data control unit 47 performs direct access to the server cluster 13 to acquire medical care data, and updates the progress information 50 and the data address information 51 in the storage medium 30B according to the acquired medical care data.

The page editor 48 generates the first information page 15A according to the record information 16 in the storage medium 30B, and transfers the first information page 15A to the GUI controller 41. The GUI controller 41 causes the display panel 34B to display the first information page 15A. The page editor 48 edits the first and second information pages 15A and 15B according to the request for editing issued by the request generator 42. Thus, a medical support apparatus can be constituted by the client terminal apparatus 12 of FIG. 36 without being limited to the medical support server apparatus 11 of the above embodiments.

In the above embodiments, the data control unit 47 acquires medical care data from the server cluster 13. However, the invention is not limited. For example, the data control unit 47 can generate a request for acquiring medical care data in synchronism with creating and editing the first and second information pages 15A and 15B. In this structure, the record database 11A is unnecessary for the medical support server apparatus 11. The medical support server apparatus 11 creates the data address information 51 and the progress information 50 of the record information 16 at each time of acquiring the medical care data from the server cluster 13. Furthermore, updated medical care data can be automatically transmitted from the server cluster 13 to the data control unit 47 at the time of updating the medical care data, instead of generating a request for the acquisition from the data control unit 47.

Furthermore, a partial function in the medical support apparatus can be provided in the medical support server apparatus 11, and another partial function in the medical support apparatus can be provided in the client terminal apparatus 12. For example, the medical support server apparatus 11 can create the first information page 15A, which can be edited in the client terminal apparatus 12. In short, a computer system constituted by the client terminal apparatus 12 and the medical support server apparatus 11 is a medical support system of the invention. In conclusion, the medical support apparatus and the medical support system of the invention can be constructed in various forms.

Also, hardware construction in each computer of the medical support server apparatus 11, the client terminal apparatus 12 and the like can be modified in various forms. For example, the medical support server apparatus 11 can be constituted by a plurality of server computers discrete from one another as hardware for the purpose of high performance of processing and high reliability. Various changes related to the hardware of the computers are possible suitably for the performance, safety, reliability and the like to meet the requirements of the entire system.

Furthermore, it is possible to duplicate the control program 45 as an application program for the purpose of ensuring safety and reliability in addition to the hardware. Two or more storage media can be used in combination for storing the control program 45 for the similar purpose.

In the above embodiments, the medical support server apparatus 11 and the client terminal apparatus 12 are used in a single hospital facility. However, the client terminal apparatus 12 can be used remotely in relation to the medical support server apparatus 11. For example, the medical support server apparatus 11 can be disposed in a data center located outside a site of the hospital facility. Application services, such as data distribution services, from the medical support server apparatus 11 can be usable at the client terminal apparatuses 12 in a plurality of hospital facilities.

To this end, the medical support server apparatus 11 is connected with the client terminal apparatus 12 in each of plural hospital facilities in a communicable manner by use of the Internet, public communication network or other system of the WAN (Wide Area Network). The medical support server apparatus 11 receives a request for processing from the client terminal apparatus 12 of the plural hospital facilities, and performs information distribution of the first information page 15A to each client terminal apparatus by use of the application service.

The data center and a service provider for installation and management of the medical support server apparatus 11 can be any one of the plural hospital facilities and can be a service company or the like discrete from the hospital facilities. Also, it is possible in utilizing the WAN as a network to establish VPN (Virtual Private Network) for information security, and to utilize communication protocol with a high security level, such as HTTPS (Hypertext Transfer Protocol Secure).

The present invention is not limited to the above embodiments. Various features of the embodiments and variants of the invention can be combined with each other suitably. Also, the computer-executable program and a storage medium for storing the computer-executable program are included in the scope of the present invention.

According to one embodiment mode of the invention, a non-transitory computer readable medium for storing a computer-executable program is provided, the computer-executable program enabling execution of computer instructions to perform operations for medical support. The operations include generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. The operations include changing over an undisplayed portion to a display state for view in response to an input action for scroll assuming that at least one of a partial information item among the plural information items and partial identification data among the plural identification data is in the undisplayed portion hidden from the information page. The operations include displaying at least one of first and second number data in the information page, the first number data being a number of the partial information item, the second number data being a number of the partial identification data.

According to another preferred embodiment mode of the invention, a medical support apparatus includes a page generator for generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. A display processor is operable in response to an input action for scroll, for display processing to change over an undisplayed portion to a display state for view assuming that at least one of part of the plural information items and at least one of the identification data is in an active display area in the information page, and assuming that at least one of remaining part of the plural information items and at least remaining one of the identification data is the undisplayed portion hidden from the information page. The display processor performs display processing of at least one of first and second data list areas in the information page, the first data list area has an array of first block cells of which a number is equal to a total of the information items included in an active display area and the undisplayed portion, and the second data list area has an array of second block cells of which a number is equal to a total of the identification data included in the active display area and the undisplayed portion.

Also, a medical support method includes a step of generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. An undisplayed portion is changed over to a display state for view assuming that at least one of part of the plural information items and at least one of the identification data is in an active display area in the information page, and assuming that at least one of remaining part of the plural information items and at least remaining one of the identification data is the undisplayed portion hidden from the information page. At least one of first and second data list areas is displayed in the information page, the first data list area has an array of first block cells of which a number is equal to a total of the information items included in an active display area and the undisplayed portion, and the second data list area has an array of second block cells of which a number is equal to the identification data included in the active display area and the undisplayed portion.

Also, a medical support system including a medical support apparatus, and a client terminal apparatus connected with the medical support apparatus communicably by network connection, is provided. A page generator generates an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. A display processor is operable in response to an input action for scroll, for display processing to change over an undisplayed portion to a display state for view assuming that at least one of part of the plural information items and at least one of the identification data is in an active display area in the information page, and assuming that at least one of remaining part of the plural information items and at least remaining one of the identification data is the undisplayed portion hidden from the information page. The display processor performs display processing of at least one of first and second data list areas in the information page, the first data list area has an array of first block cells of which a number is equal to a total of the information items included in an active display area and the undisplayed portion, and the second data list area has an array of second block cells of which a number is equal to a total of the identification data included in the active display area and the undisplayed portion.

Also, a non-transitory computer readable medium for storing a computer-executable program is provided, the computer-executable program enabling execution of computer instructions to perform operations for medical support. The operations include generating an information page having a patient list for indicating plural information items by patient bodies, wherein the patient list is in a two-dimensional form defined by use of a first axis along which the plural information items are arranged in relation to medical care of the patient bodies, and a second axis along which identification data are arranged for identifying the patient bodies. The operations include changing over an undisplayed portion to a display state for view assuming that at least one of part of the plural information items and at least one of the identification data is in an active display area in the information page, and assuming that at least one of remaining part of the plural information items and at least remaining one of the identification data is the undisplayed portion hidden from the information page. The operations include displaying at least one of first and second data list areas in the information page, the first data list area has an array of first block cells of which a number is equal to a total of the information items included in an active display area and the undisplayed portion, and the second data list area has an array of second block cells of which a number is equal to a total of the identification data included in the active display area and the undisplayed portion.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A medical support apparatus comprising:
   a processor configured to:
   generate an information page having a patient list for indicating plural information items by patient bodies, wherein said patient list is in a two-dimensional form defined by use of a first axis along which said plural information items are arranged in relation to medical care of said patient bodies, and a second axis along which plural identification data are arranged for identifying said patient bodies, and the plural information items include at least one first information item having a plurality of elements which relate to diagnostic tests;

control a display, in response to an input action for scroll, to control the display to change over an undisplayed portion to a display state for view assuming that at least one of a partial information item among said plural information items and partial identification data among said plural identification data is in said undisplayed portion hidden from said information page;

and further control the display to change a display form of corresponding ones of the plurality of elements in the first information item according to changes in progress of the diagnostic tests, wherein the plural information items are icons having an equal size and arranged regularly, and wherein said processor is further configured to control the display to display at least one of a first and second number data, wherein the first number data is a number of said partial information item, and the second number data is a number of said partial identification data, and wherein the first or second number data is indicated in a translucent form in said patient list, and wherein the first or second number data is deleted from said information page upon occurrence of an action for scroll, wherein said patient list is generated for each one of plural medical professionals, and at least one of said information items, said identification data and said progress is different between said professionals in relation to said plural patient bodies and said clinical process, wherein said patient list is generated according to one of plural patient types of said patient bodies, and at least one of said information items, said identification data and said progress is different between said patient types, and wherein the first or second number data is displayed in a floating window that is displayed on the patient list and displays a simplified form of the undisplayed portion and an active display area of the patient list.

2. A medical support apparatus as defined in claim 1, wherein said first or second number data is displayed in a number window area for indicating a hidden form of said undisplayed portion.

3. A medical support apparatus as defined in claim 2, wherein said number window area is shaped to project in one direction, and points a direction associated with said undisplayed portion.

4. A medical support apparatus as defined in claim 1, wherein said information items include an information item of a clinical process performed by a medical professional for said patient bodies.

5. A medical support apparatus as defined in claim 4, wherein at least one icon portion is displayed in said patient list;
said icon portion is arranged in one or more arrays, displayed in relation to said clinical process of which a schedule is registered, for expressing said information item graphically.

6. A medical support apparatus as defined in claim 5, wherein said icon portion expresses progress of said clinical process, and has a display form changeable with a change in said progress.

7. A medical support apparatus as defined in claim 1, wherein said patient type is a selected one of a surgery-scheduled patient for whom a surgery is scheduled, an out-patient and an in-patient.

8. A medical support method comprising steps of:
generating an information page having a patient list for indicating plural information items by patient bodies, wherein said patient list is in a two-dimensional form defined by use of a first axis along which said plural information items are arranged in relation to medical care of said patient bodies, and a second axis along which plural identification data are arranged for identifying said patient bodies, and the plural information items include at least one first information item having a plurality of elements which relate to diagnostic tests;

controlling a display to change over an undisplayed portion to a display state for view, in response to an input action for scroll, assuming that at least one of a partial information item among said plural information items and partial identification data among said plural identification data is in said undisplayed portion hidden from said information page; and controlling the display to change a display form of corresponding ones of the plurality of elements in the first information item according to changes in progress of the diagnostic tests, wherein the plural information items are icons having an equal size and arranged regularly;

controlling the display to display at least one of a first and second number data, wherein the first number data is a number of said partial information item, and the second number data is a number of said partial identification data, and wherein the first or second number data is indicated in a translucent form in said patient list, and wherein the first or second number data is deleted from said information page upon occurrence of an action for scroll, wherein said patient list is generated for each one of plural medical professionals, and at least one of said information items, said identification data and said progress is different between said professionals in relation to said plural patient bodies and said clinical process, wherein said patient list is generated according to one of plural patient types of said patient bodies, and at least one of said information items, said identification data and said progress is different between said patient types, and wherein the first or second number data is displayed in a floating window that is displayed on the patient list and displays a simplified form of the undisplayed portion and an active display area of the patient list.

9. A medical support system including a medical support apparatus, and a client terminal apparatus connected with said medical support apparatus communicably by network connection, comprising:
at least one processor configured to:
generate an information page having a patient list for indicating plural information items by patient bodies, wherein said patient list is in a two-dimensional form defined by use of a first axis along which said plural information items are arranged in relation to medical care of said patient bodies, and a second axis along which plural identification data are arranged for identifying said patient bodies, and the plural information items include at least one first information item having a plurality of elements which relate to diagnostic tests;

control a display, in response to an input action for scroll, to control the display to change over an undisplayed portion to a display state for view assuming that at least one of a partial information item among said plural information items and partial identification data among said plural identification data is in said undisplayed portion hidden from said information page; and further control the display to change a display form of corresponding ones of the plurality of elements in the first information item according to changes in progress of the diagnostic tests, wherein the plural information items are icons having an equal size and arranged regularly, control the display to display at least one of a first and second number data, wherein the first number data is a number of said partial information item, and the second number data is a number of said partial identification data, and wherein the first or second number data is indicated in a translucent form in said patient list, and wherein the first or second number data is deleted from said information page upon occurrence of an action for scroll, wherein said patient list is generated for each one of plural medical professionals, and at least one of said information items, said identification data and said progress is different between said professionals in relation to said plural patient bodies and said clinical process, wherein said patient list is generated according to one of plural patient types of said patient bodies, and at least one of said information items, said identification data and said progress is different between said patient types, and wherein the first or second number data is displayed in a floating window that is displayed on the patient list and displays a simplified form of the undisplayed portion and an active display area of the patient list.

* * * * *